(12) United States Patent
Suzuki

(10) Patent No.: US 6,262,237 B1
(45) Date of Patent: Jul. 17, 2001

(54) METHODS OF ANTAGONIZING THE BINDING OF PROTOCADHERIN-42

(75) Inventor: Shintaro Suzuki, Torrance, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 09/099,639

(22) Filed: Jun. 18, 1998

Related U.S. Application Data

(60) Division of application No. 08/268,161, filed on Jun. 27, 1994, now Pat. No. 5,798,224, which is a continuation-in-part of application No. PCT/US93/12588, filed on Dec. 23, 1993, which is a continuation-in-part of application No. 07/998,003, filed on Dec. 29, 1992, now Pat. No. 5,643,781.

(51) Int. Cl.$^7$ .......................... C07K 16/28; C07K 14/46; C12P 21/00; G01N 33/53

(52) U.S. Cl. .................. 530/387.1; 530/350; 435/7.1; 435/69.1

(58) Field of Search .................. 435/7.1, 69.1; 530/350, 387.1

(56) References Cited

FOREIGN PATENT DOCUMENTS

WO 91/04745   4/1991  (WO).
WO 92/08731   5/1992  (WO).

OTHER PUBLICATIONS

Amagai et al., "Autoantibodies against a Novel Epithelial Cadherin in *Pemphigus Vulgaris,* a Disease of Cell Adhesion", *Cell,* 67: 869–877 (Nov. 29, 1991).
Angerer et al., "Demonstration of Tissue–Specific Gene Expression by in Situ Hybridization", *Methods in Enzymology,* 152: 649–660, (1987).
Ausubel et al., Eds., *Current Protocols in Molecular Biology,* Sections 6.1.1 to 6.1.4 and 6.2.1 to 6.2.3, John Wiley & Sons, New York (1987).
Burt, "Morphologic Abnormalities in the Postnatal Differentiation of CA1 Pyramidal Cells and Granule Cells in the Hippocampal Formation of the Ataxic Mouse", *Anat. Rec.* 196: 61–69 (1980).
Chen et al., "Cell–Cell Contacts Mediated by E–Cadherin (Uvomorulin) Restrict Invasive Behavior of L–Cells:, *J. Cell, Biol.,* 114(2): 319–327 (Jul. 1991).
Civitelli et al., "Connexin43 Mediates Direct Intercellular Communication in Human Osteoblastic Cell Networks", *J. Clin. Invest.,* 91: 1888–1896 (1993).
Detrick et al., "The Effects of N–Cadherin Misexpression on Morphogenesis in Xenopus Embryos", *Neuron,* 4: 493–506 (Apr. 1990).
Donalies et al., "Expression of M–cadherin, a Member of the Cadherin Multigene Family, Correlates with Differentiation of Skeletal Muscle Cells", *Proc. Natl. Acad. Sci. USA,* 88: 8024–8028 (Sep. 1991).

Frixen et al., "E–Cadherin–Mediated Cell–Cell Adhesion Prevents Invasiveness of Human Carcinoma Cells", *J. Cell. Biol.,* 113(1): 173–185 (Apr. 1991).
Fujimori et al., "Ectopic Expression of N–cadherin Perturbs Histogenesis in Xenopus Embryos", *Development,* 110: 97–104 (1990).
Gallin et al., "Sequence Analysis of a cDNA Clone Encoding the Liver Cell Adhesion Molecule, L–CAM", *Proc. Natl. Acad. Sci. USA,* 84: 2808–2812 (May 1987).
Goodwin et al., "Desmoglein Shows Extensive Homology to the Cadherin Family of Cell Adhesion Molecules", *Biochem. Biophsy. Res. Commun.,* 173(3): 1224–1230 (Dec. 31, 1990).
Hatta et al., "Cloning and Expression of cDNA Encoding a Neural Calcium–dependent Cell Adhesion Molecule: Its Identity in the Cadherin Gene Family", *J. Cell. Biol.,* 106: 873–881 (Mar. 1998).
Holton et al., "Desmosomal Glycoproteins 2 and 3 (desmocollins) Show N– terminal Similarity to Calcium–Dependent Cell–Cell Adhesion Molecules", *J. Cell. Science,* 97: 239–246 (1990).
Hynes et al., "Contact and Adhesive Specificities in the Associations, Migrations, and Targeting of Cells and Axons", *Cell,* 68: 303–322, (Jan. 24, 1992).
Inuzuka et al., "R–Cadherin: A Novel $Ca^{2+}$–Dependent Cell–Cell Adhesion Molecule Expressed in the Retina", *Neuron,* 7: 69–79 (1991).
Kennett, "Cell Fusion", *Methods in Enzymol.,* 58: 345–359 (1979).
Kikuchi et al., "The Defective Organ of Corti in Shaker–1 Mice", *Acta Oto–Laryng.,* 60: 287–303 (1965).
Kintner, "Regulation of Embryonic Cell Adhesion by the Cadherin Cytoplasmic Domain", *Cell,* 69: 225–236 (Apr. 17, 1992).
Koch et al., "Identification of Desmoglein, a Constitutive Desmosomal Glycoprotein, as a Member of the Cadherin Family of Cell Adhesion Molecules", *Eur. J. Cell Biol.,* 53: 1–12 (1990).
Liaw et al., "Identification and Cloning of Two Species of Cadherins in Bovine Endothelial Cells", *EMBO J.,* 9(9): 2701–2708 (1990).
Lord et al., Shaker, A New Mutation of the House Mouse (*Mus Musculus*) *Am. Nat.,* 63: 453–442 (1929).
Lyon, M., "Twirler: A Mutant Affecting the Inner Ear of the House Mouse", *J. Embryol. Exp. Morphol.,* 6: 105–116 (1958).

(List continued on next page.)

*Primary Examiner*—David Romeo
(74) *Attorney, Agent, or Firm*—Marshall, O'Toole, Gerstein, Murray & Borun

(57) ABSTRACT

Polynucleotide sequences encoding novel cadherin-like polypeptides, designated protocadherins, and variants thereof are provided by the invention as well as methods and materials for the recombinant production of the same. Antibody substances specific for protocadherins are also disclosed as useful for modulating the natural binding and/or regulatory activities of the protocadherins.

1 Claim, 3 Drawing Sheets

OTHER PUBLICATIONS

Lyon, M., "Ataxia—A New Recessive Mutant of the House Mouse", *J. Hered.,* 46: 77–80 (1955).

Mahoney et al., "The fat Tumor Suppressor Gene in Drosophila Encodes a Novel Member of the Cadherin Gene Superfamily", *Cell,* 67: 853–868 (Nov. 29, 1991).

Maniatis et al., pp. 196 in *Molecular Cloning: A Laboratory Manual,* Cold Spring Harbor, New York: Cold Spring Harbor Laboratory (1982).

Maruyama et al., "Detection of Calcium Binding Proteins by $^{45}$Ca Autoradiography on Nitrocellulose Membrane after Sodium Dodecyl Sulfate Gel Electrophoresis[1]", *J. Biochem.,* 95: 511–519 (1984).

Matsunaga et al., "Guidance of Optic Nerve Fibers by N–cadherin Adhesion Molecules", *Nature,* 334: 62–64 (Jul. 1988).

Miyatani et al., "Neural Cadherin: Role in Selective Cell–Cell Adhesion", *Science,* 245: 631–635 (Aug. 1989).

Nagafuchi et al., "Transformation of Cell Adhesion Properties by Exogenously Introduced E–cadherin cDNA", *Nature,* 329: 341–343 (Sep. 1987).

Napolitano, et al., "Molecular Cloning and Characterization of B–Cadherin, a Novel Chick Cadherin", *Cell. Biol.,* 113(4): 893–905 (May 1991).

Nose et al., "Isolation of Placental Cadherin cDNA: Identification of a Novel gene Family of Cell–Cell Adhesion Molecules", *EMBO J.,* 6(12): 3655–3661 (1987).

Porter et al., "Dystrophin Colocalizes with β–Spectrin in Distinct Subsarcolemmal Domains in Mammalian Skeletal Muscle", *J. Cell. Biol.,* 117(5): 997–1005 (Jun. 1992).

Pytela et al., "Polymerase Chain Reaction Cloning with Degenerate Primers: Homology–Based Identification of Adhesion Molecules", *Methods in Enzymology,* Erkki Ruoslahti and Eva Engvall, Eds., 245:420–451, Academic Press, (1994).

Ranscht et al., "T–Cadherin, a Novel Cadherin Cell Adhesion Mol. in the Nervous System Lacks the Conserved Cytoplasmic Region", *Neuron,* 7: 391–402 (Sep. 1991).

Ringwald et al., "The Structure of Cell Adhesion Molecule Uvomorulin. Insights into the Molecular Mechanism of $Ca^{2+}$–Dependent Cell Adhesion", *EMBO J.,* 6(12): 3647–3653 (1987).

Sano et al. "Protocadherins: A Large Family of Cadherin–Related Molecules in Central Nervous System", *The EMBO Journal,* 12(6): 2249–2256 (1993).

Seldon et al., "Genetic Analysis of Autoimmune gld Mice", *J. Exp. Med.,* 167: 688–693 (1988).

Shimoyama et al., "Molecular Cloning of a Human $Ca^{2+}$–Dependent Cell–Cell Adhesion Molecule Homologous to Mouse Placental Cadherin: Its Low Expression in Human Placental Tissues", *J. Cell. Biol.,* 109: 1787–1794 (Oct. 1989).

Suzuki et al., "Diversity of the Cadherin Family: Evidence for Eight New Cadherins in Nervous Tissue", *Cell Regulation,* 2: 261–270 (Apr. 1991).

Suzuki et al., "Evidence for Cadherin Superfamily" *Cell Struc. Func.,* 16: 605 (Nov. 23, 1991).

Suzuki et al., "Evidence for Cadherin Superfamily" *J. Cell. Biol.,* 115: 72(a) (Abstract 416) (Dec. 9, 1991).

Takeichi, Cadherin Cell Adhesion Receptors as a Morphogenetic Regulator:, *Science,* 251: 1451–1455 (Mar. 1991).

Takeichi, "Cadherins: A Molecular Family Important in Selective Cell–Cell Adhesion:, *Annu. Rev. Biochem.,* 59: 237–252 (1990).

Thomas, "Hybridization of Denatured RNA and Small DNA Fragments Transferred to Nitrocellulose", *Proc. Natl. Acad. Sci. USA,* 77(9): 5201–5205 (Sep. 1980).

Towbin et al., "Electrophoretic Transfer of Proteins from Polyacrylamide Gels to Nitrocellulose Sheets: Procedure and Some Applications:, *PNAS* 76: 4350–4354, (Sep. 1979).

Urushihara et al., "Immunological Detection of Cell Surface Components Related with Aggregation of Chinese Hamster and Chick Embryonic Cells", *Dev. Biol.,* 70: 206–216 (1979).

Vandenbark et al., "Experimental Allergic Encephalomyelitis and Cellular Immunity in the Lewis Rat", *Cell. Immunol.,* 12: 85–93 (1974).

Vleminckx et al., "Genetic Manipulation of E–Cadherin Expression by Epithelial Tumor Cells Reveals an Invasion Suppressor Role", *Cell,* 66: 107–119 (Jul. 12, 1991).

```
PC43  EC 1   ASTVIHYEIPEEREK-------GFAVGNVVANL--GLDLGSLSA--
      EC 2   PTQEMKLEISEAVAP-------GTRFPLESAH---DPDLGSNSL--
      EC 3   NQSLYRARVPGGCTS-------GTRVVQVLAT---DLDEGPNGE--
      EC 4   TVTSVYSPVPEDAS--------GTVIALLSVT---DLDAGENGL--
      EC 5   SQSSYDVYIEENNLP-------GAPILNLSVW---DPDAPQNAR--
      EC 6   LYPRPGGSSVEMLPRGTSA-GHLVSRVVGW---DADAGHNAW--

PC42  EC 1   VPEEQPPNTLI-----------GSL----------AADYGFPDVG-
      EC 2   ASPVITLAIPENTNI-------GSLFPIPLAS---DRDAGPNGV--
      EC 3   ERPSYEAELSENSPI-------GHSVIQVKAN---DSDQGANAE--
      EC 4   EIRGIGLVTHQDGMANISEDVAEETAVALVQVSDRDEGENAA--
      EC 5   TQSVTEVAFPENNKP-------GEVIAEITAS---DADSGSNAE--
      EC 6   MLSGYNFSVMENMPA-------LSPVGMVTVI---DGDKGENAQ--
      EC 7   TAPSNTSHKLLTPQTRL-----GETVSQVAAE---DFDSGVNAE--

FAT   EC18   EDTVYSFDIPENAQR-------GYQVGQIVAR---DADLGQNAQ--

N-CAD EC 1   DWVIPPINLPENSRG-------PFPQELVRIRS--DRDKNLSLRYT
      EC 2   LHQVWNGTVPEGSKP-------GTYVMTVTAI---DADDPNALNGM
      EC 3   TAMTFYGEVPENRVD-------IIVANLTVT----DKDQPHTPAWN
      EC 4   APNPKIIRQEEGLHA-------GTMLTTFTAG---DPDRYMQON--
      EC 5   LPQEAETCETPDPNSINITTAL-------------DYDIDPNAGP--

MOTIF        *****o*****v*En****--------Gt*v***v*A*----D*D*g*N**--
```

FIGURE 1A

```
PC43  EC 1    RRFPVVSGASRR--------FFEVNRET----GEMFVNDR-------
      EC 2    QTYELSRNEY----------FALRVQTREDSTKYAELVLERA----
      EC 3    IIYSFGSHNRAGVRQL----FALDLVT-----GMLTIKGR------
      EC 4    VTCEVPPGLP----------FSLTSSLKNYFTLKTSAD--------
      EC 5    LSFFLLEQGAETGLVGRYFTINRDN-------GIVSSLVP------
      EC 6    LSYSLFGSPNQSL-------FAIGLHT-----GQISTARPV-----

PC42  EC 1    HLYKLEVGAP----------YLRVDGKT----GDIFTETS------
      EC 2    ASYELQVAED----------QEEKQPQLIVMGN-------------
      EC 3    IEYTFHQAPEVVRRL-----LRLDRNT-----GLITVQGP------
      EC 4    VTCVVAGDVP----------FQLRQASETGSDSKKKYFLQTTTP
      EC 5    LVYSLEPEPAAKGL------FTISPET-----GEIQVKTS------
      EC 6    VQLSVEQDNGD---------FVIQNGT-----GTILSSLS------
      EC 7    LIYSIAGGNPYGL-------FQIGSHS-----GAITLEKE------

FAT   EC18    LSYGVVSDWANDV-------FSLNPQT-----GMLTLTAR------

N-CAD EC 1    VTGPGADQPPTGI-------FIINPIS-----GQLSVTKP------
      EC 2    LRYRIVSQAPSTPSPNM-FTINNET-----GDIITVAAG-------
      EC 3    AVYRISGGDPTGR-------FAIQTDPNSND-GLVTVVKP------
      EC 4    IRYTKLSDPAN---------WLKIDPVN----GQITTIAV------
      EC 5    FAFDLPLSPVTIKRN-----WTITRLN-----GDFAQLNLK-----

MOTIF          I*O*I***********O*I***T------G*I*T***-----
```

FIGURE 1B

```
PC43  EC 1  LDRLELCGTLPSCTVTLELVVENP------------------LELFSVEVVIQDINDNNPAF
      EC 2  LDREREPSLQLVLTALDGGTPAL-------------------SASLPIHIKVLDANDNAPVF
      EC 3  LDFEDTKLHEIYIQAKDKGANPE-------------------GAHCKVLVEVVDVNDNAPEI
      EC 4  LDRETVPEYNLSITARDAGTPSL-------------------SALTIVRVQVSDINDNPPQS
      EC 5  LDYEDRREFELTAHISDGGTPVL-------------------ATNISVNIFVTDRNDNAPQV
      EC 6  QDTDSPRQTLTVL-IKDNGEPSLSTTATLTVSVTEDSPEARAEFPSGSAPREQKKN

PC42  EC 1  IDREGLRECQNQLPGDPCILEFEVSITDLVQNAS--PRLLEGQIEVQDINDNTPNF
      EC 2  LDRERWDSYDLTIKVQDGGSPPR-------------------ATSALLRVTVLDTNDNAPKF
      EC 3  VDREDLSTLRFSVLAKDRGTNPK-------------------SARAQVVVTVKDMNDNAPTI
      EC 4  LDYEKVKDYTIEIVAVDSGNPPL-------------------SSTNSLKVQVVDVNDNAPVF
      EC 5  LDREQRESYELKVVAADRGSPSL-------------------QGTATVLVNVLDCNDNDPKF
      EC 6  FDREQQSTYTFQLKAVDGGVPPR-------------------SAYVGVTINVLDENDNAPYI
      EC 7  IERRHHGLHRLVVKVSDRGKPPRYGTALVHLYVNETLANRTLLETLLGHSLDTPLD
                                                  IDIAGDPEYERSKQRGN

FAT   EC18  LDYEEVQHYILIVQAQDNGQPSL-------------------STTITVYCNVLDLNDNAPIF

N-CAD EC 1  LDREQIARFHLRAHAVDINGNQV-------------------ENPIDIVINVIDMNDNRPEF
      EC 2  LDRENVQQYTLIIQATDMEGIPTYGL----------------SNTATAVITVTDVNDNPPEF
      EC 3  IDFETNRMFVLTVAAENQVPLAKGIQHPP-------------QSTATVSVTVIDVNE-NPYF
      EC 4  LDRESPNVKNNIYNATFLASDNGIPPM---------------SGTGTLQIYLLDINDNAPQV
      EC 5  IKFLEAGIYEVPIIITDSGNPPKSNIS---------------ILRVRVCQCDFNGDCTDVDR

MOTIF       LDRE****o*L*v*A*D*G*P**-------------------**T*TV*v*V*D*NDNAP*F
```

FIGURE 1C

METHODS OF ANTAGONIZING THE BINDING OF PROTOCADHERIN-42

This is division of U.S. application Ser. No. 08/268,161, filed Jun. 27, 1994, now U.S. Pat. No. 5,798,224.

This application is a continuation-in-part of International Patent Application No. PCT/US93/12588 filed Dec. 23, 1993 which is in turn a continuation-in-part of U.S. patent application Ser. No. 07/998,003 which was filed on Dec. 29, 1992, now U.S. Pat. No. 5,643,781.

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasation, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through catenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59: 237–252 (1990) and Takeichi, *Science*, 251: 1451–1455 (1991).

The first cadherins to be described (Edherin in mouse epithelial cells, L-CAM in avian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et al., *Nature*, 329: 341–343 (1987)], N-cadherin [Hatta et al., *J. Cell. Biol*, 106: 873–881 (1988)], and P-cadherin [Nose et al., *EMBO J.*, 6: 3655–3661 (1987)] provided structural evidence that the cadherins comprised a family of cell adhesion molecules. Cloning of L-CAM [Gallin et al., *Proc. Natl. Acad., Sci. USA*, 84: 2808–2812 (1987)] and uvomorulin [Ringwald et al., *EMBO J.*, 6: 3647–3653 (1986)] revealed that they were identical to E-cadherin. Comparisons of the amino acid sequences of E-, N-, and P-cadherins showed a level of amino acid similarity of about 45%–58% among the three subclasses. Liaw et al., *EMBO J.*, 9: 2701–2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., *Cell Regulation*, 2: 261–270 (1991). Subsequently, several other cadherins were described including R-cadherin [Inuzuka et al., *Neuron*, 7: 69–79 (1991)], M-cadherin [Donalies, *Proc. Natl. Acad. Sci. USA*, 88: 8024–8028 (1991)], B-cadherin [Napolitano, *J. Cell. Biol.*, 113: 893–905 (1991)] and T-cadherin [Ranscht, *Neuron*, 7: 391–402 (1991)].

Additionally, proteins distantly related to cadherins such as desmoglein [Goodwin et al., *Biochem. Biophys. Res. Commun.*, 173: 1224–1230 (1990) and Koch et al., *Eur. J. Cell Biol.*, 53: 1–12 (1990)] and the desmocollins [Holton et al., *J. Cell Science*, 97: 239–246 (1990)] have been described. The extracellular domains of these molecules are structurally related to the extracellular domains of typical cadherins, but each has a unique cytoplasmic domain. Mahoney et al., *Cell*, 67: 853–868 (1991) describes a tumor suppressor gene of Drosophila, called fat, that also encodes a cadherin-related protein. The fat tumor suppressor comprises 34 cadherin-like subdomains followed by four EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins, also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., *Neuron*, 4: 493–506 (1990); Fujimori et al., *Development*, 110: 97–104 (1990); Kintner, *Cell*, 69: 225–236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with *pemphigus vulgaris*, an autoimmune skin disease characterized by blister formation caused by loss of cell adhesion, react with a cadherin-related protein offering direct support for adhesion function of cadherins in vivo [Amagai et al., *Cell,* 67: 869–877 (1991)]. Studies have also suggested that cadherins and cadherin-related proteins may have regulatory functions in addition to adhesive activity. Matsunaga et al., *Nature,* 334: 62–64 (1988) reports that N-cadherin has neurite outgrowth promoting activity. The Drosophila fat tumor supressor gene appears to regulate cell growth and supress tumor invasion as does mammalian E-cadherin [see Mahoney et al., supra; Frixen et al., *J. Cell. Biol.,* 113:173–185 (1991); Chen et al., *J. Cell, Biol.,* 114:319–327 (1991); and Vleminckx et al., *Cell,* 66:107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/antiligand binding reactions in which the proteins are involved.

SUMMARY OF THE INVENTION

The present invention provides cadherin-related materials and methods that are relevant to cell-cell adhesion. In one of its aspects, the present invention provides purified and isolated polynucleotides (e.g., DNA and RNA, both sense and antisense strands) encoding the novel cell adhesion molecules designated herein as protocadherins, including protocadhein-42, protocadherin-43, protocadherin pc3, protocadherin pc4 and protocadherin pc5. Preferred polynucleotide sequences of the invention include genomic and cDNA sequences as well as wholly or partially synthesized DNA sequences, and biological replicas thereof (i.e., copies of the sequences made in vitro). Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parkiawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by standard DNA/DNA hybridization or PCR techniques of full length cDNA or genomic DNA sequences that encode the protein (or variants thereof) and, in the case of genomic DNA sequences, that specify protocadherin-specific regulatory sequences such as promoters, enhancers and the like. Alternatively, DNA sequences of the present invention may be chemically synthesized by conventional techniques. Hybridization and PCR techiques also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of protocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly de-glycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function. Also contemplated by the present invention are antibody substances (e.g., monoclonal and polyclonal antibodies, chimeric and humanized antibodies, antibody domains including Fab, Fab', F(ab')$_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 38I2C which was deposited with the ATCC on Dec. 2, 1992 and was assigned ATCC Accession No. HB 11207.

Numerous other aspects and advantages of the present invention will be apparent upon consideration of the following detailed description, reference being made to the drawing wherein FIGS. 1A–C is an alignment of protocadherin amino acid sequences of the invention with the amino acid sequences of N-cadherin and of the Drosophila fat tumor suppressor.

BRIEF DESCRIPTION OF THE DRAWING

FIGS. 1A–1C presents an alignment of the amino acid sequences of the deduced extracellular subdomains of PC42 (EC-1 through EC-7) (amino acids 42–818)of SEQ ID NO: 95), PC43 (EC-1 through EC-6), (amino acids 29–688 of SEQ ID NO: 97), mouse N-cadherin (EC-1 through EC-5) (amino acids 1–557 of SEQ ID NO: 98) and drosophila fat EC-18 (SEQ ID NO: 99). A sequence on a line in FIG. 1A continues on the same line in FIGS. 1B and 1C.

DETAILED DESCRIPTION

The present invention is illustrated by the following examples wherein Examples 1, 2 and 3 describe the isolation by PCR of protocadherin polynucleotide sequences. Example 3 also describes the chromosome localization of several protocadherin genes of the invention. Example 4 describes the isolation by DNA/DNA hybridization of additional protocadherin polynucleotide sequences of the present invention. Example 5 presents the construction of expression plasmids including polynucleotides encoding protocadherin-42 or protocadherin-43 and the transfection of L cells with the plasmids. The generation of antibodies to protocadherin-42 and protocadherin-43 is described in Example 6. Example 7 presents the results of immunoassays of transfected L cells for the expression of protocadherin-42 or protocadherin-43. Example 8 describes the cell aggregation properties of L cells transfected with protocadherin-42, protocadherin-43 or a chimeric protocadherin-43/E-cadherin molecule. The calcium-binding properties of pc43 are described in Example 9. The results of assays of various tissues and cell lines for the expression of protocadherin-42 and protocadherin-43 by Northern blot, Western blot and in situ hybridization are respectively presented in Examples 10, 11 and 12. Example 13 describes immunoprecipitation experiments identifying a 120 kDa protein that coprecipitates with protocadherin-43.

EXAMPLE 1

The polymerase chain reaction (PCR) was used to isolate novel rat cDNA fragments encoding cadherin-related polypeptides.

Design of PCR Primers

Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., *Science*, 245:631–635 (1989)] and human P-cadherin [Shimoyama et al., *J. Cell. Biol.*, 109:1787–1794 (1989)], and the corresponding degenerate oligonucleotides respectively set out below in IUPAC-IUB Biochemical nomenclature were designed for use as PCR primers.

```
Primer 1 (SEQ ID NO: 1)
5' AARSSNNTNGAYTRYGA 3'

Primer 2 (SEQ ID NO: 2)
3' TTRCTRTTRCGNGGNNN 5'
```

The degenerate oligonucleotides were synthesized using an Applied Biosystems model 380B DNA synthesizer (Foster City, Calif.).

Cloning of cDNA Sequences by PCR

PCR was carried out in a manner similar to that described in Suzuki et al., *Cell Regulation*, 2: 261–270 (1991) on a rat brain cDNA preparation. Total RNA was prepared from rat brain by the guanidium isothiocyanate/cesium chloride method described in Maniatis et al., pp. 196 in *Molecular Cloning: A Laboratory Manual,* Cold Spring Harbor, N.Y.: Cold Spring Harbor Laboratory (1982). Brain poly(A)$^+$ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 $\mu$g of each primer, after which 35 reaction cycles of denaturation at 94° C. for 1.5 minutes, annealing at 45° C. for 2 minutes, and polymerization at 72° C. for 3 minutes were carried out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 polynucleotide kinase and subcloned by a blunt-end ligation into the Sma I site of M13mp18 (Boehringer Mannheim Biochemicals) in a blunt end ligation for sequence analysis. Sequencing of the fragments was carried out by the dideoxynucleotide chain termination method using a Sequenase kit (United States Biochemicals, Cleveland, Ohio). DNA and amino acid sequence were analyzed using the Beckman Microgenie program (Fullerton, Calif.).

Analysis of cDNA Sequences

Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F instead of D-X-N-E-X-P-X-F or D-X-D-E-X-P-X-F, at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from Drosophila and *C. elegans* whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN-42 (SEQ ID NOs: 62 and 63), HUMAN43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and C. Elegans-41 (SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of Full-length Human cDNAs

A human fetal brain cDNA library (Stratagene, La Jolla, Calif.) in the λZapII vector was screened by the plaque hybridization method [described in Ausubel et al., Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

A description of the cloning of protocadherin sequences of the invention was published in Sano et al., *The EMBO Journal*, 12(6): 2249–2256 (1993) after filing of the priority application hereto. The deduced amino acid sequence of pc43 was previously presented at the Dec. 9, 1991 meeting of the American Society for Cell Biology. An abstract of the presentation is published as Suzuki et al., *J. Cell. Biol.*, 115: 72a (Abstract 416) (Dec. 9, 1991).

Analysis of Full-length Human Clones

Comparison of the full length cDNA sequences of pc42 and pc43 to the sequences of the various DNA fragments originally obtained by PCR reveals that MOUSE-326 and HUMAN-42 correspond to a portion of the fourth extracellular subdomain (EC-4) of pc42, and RAT-314, MOUSE-321, and HUMAN-11 correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but the new molecules also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of Drosophila fat tumor suppressor (EC-18, SEQ ID NO: 99) (the eighteenth extracellular subdomain of fat is a prototypical fat subdomain) are presented in Table 1 below, wherein, for example, "N-EC-1×pc42" indicates that the first extracellular subdomain of N-cadherin was compared to the extracellular subdomain of pc42 indicated on the horizontal axis.

TABLE 1

|   | EC-1 | EC-2 | EC-3 | EC-4 | EC-5 | EC-6 | EC-7 |
|---|---|---|---|---|---|---|---|
| N-EC-1 × pc42 | 20 | 27 | 26 | 26 | 31 | 29 | 17 |
| N-EC-1 × pc43 | 31 | 23 | 23 | 26 | 31 | 24 |   |
| N-EC-2 × pc42 | 28 | 30 | 32 | 30 | 37 | 31 | 19 |
| N-EC-2 × pc43 | 30 | 28 | 30 | 36 | 29 | 30 |   |
| N-EC-3 × pc42 | 21 | 26 | 30 | 29 | 31 | 30 | 22 |
| N-EC-3 × pc43 | 25 | 18 | 26 | 28 | 28 | 25 |   |
| N-EC-4 × pc42 | 28 | 28 | 26 | 25 | 29 | 27 | 17 |
| N-EC-4 × pc43 | 21 | 25 | 28 | 28 | 29 | 24 |   |
| N-EC-5 × pc42 | 24 | 21 | 25 | 24 | 24 | 19 | 12 |
| N-EC-5 × pc43 | 15 | 21 | 20 | 20 | 25 | 16 |   |
| fat EC-18 × pc42 | 22 | 35 | 32 | 34 | 42 | 35 | 19 |
| fat EC-18 × pc43 | 32 | 30 | 36 | 36 | 33 | 29 |   |

The amino acid identity values between the extracellular subdomains of pc42 and pc43, and N-cadherin EC-1 through EC-5 and Drosophila fat EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

|  | pc42 | | | | | | |
|---|---|---|---|---|---|---|---|
| pc43 | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |

TABLE 2-continued pc42

| pc43 | EC-1 | EC-2 | EC-3 | EC-4 | EC-5 | EC-6 | EC-7 |
|---|---|---|---|---|---|---|---|
| EC-3 | 26 | 32 | 41 | 30 | 32 | 31 | 22 |
| EC-4 | 25 | 34 | 30 | 41 | 39 | 31 | 18 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIGS. 1A–C presents an alignment of the deduced amino acid sequences of the extracellular subdomains of pc42 (EC-1 through EC-7) (amino acids 42–818 of SEQ ID NO: 95), pc43 (EC-1 through EC-6) (amino acids 29–688 of SEQ ID NO: 97), mouse N-cadherin (EC-1 through EC-5) (amino acids 1–557 of SEQ ID NO: 98) and Drosophila fat EC-18 (SEQ ID NO: 99). A sequence on a line in FIG. 1A continues on the same line in FIGS. 1B and 1C. Gaps were introduced to maximize homology.

In FIGS. 1A–1C, the position at which an amino acid appears in a SEQ ID NO is indicated in parenthesis. For example, in FIG. 1A the first amino acid of EC1 of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97. The amino acid residues described by capital letters in the "motif" line are present in more than half of the subdomains of N-cadherin, pc42, pc43 and Drosophila fat. The amino acid residues described by small letters in the motif line are less well conserved in human pc42, pc43, and Drosophila fat. FIGS. 1A–C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique features in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible Alternative Splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

Chromosome Localization

The chromosomal location of the protocadherin 413 gene (SEQ ID NO: 37) and of the pc42 and pc43 genes was determined by conventional methods.

Briefly, C3H/HeJ-gld and *Mus spretus* (Spain) mice and [(C3H/HeJ-gld×*Mus spretus*) F$_1$×C3H/HeJ-gld] interspecies backcross mice were bred and maintained as previously described in Seldin, et al., *J. Exp. Med.*, 167: 688–693 (1988). *Mus spretus* was chosen as the second parent in the cross because of the relative ease of detection of informative restriction fragment length variants (RFLVs) in comparison with crosses using conventional inbred laboratory strains. Gene linkage was determined by segregation analysis.

Genomic DNA isolated from mouse organs by standard techniques was digested with restriction endonucleases and 10 μg samples were electrophoresed in 0.9% agarose gels. DNA was transferred to Nytran membranes (Schleicher & Schull, Inc., Keene, N.H.), hybridized with the appropriate probe at 65° C. and washed under stringent conditions, all as previously described in Maniatis et al., supra). To localize the pc42 gene, a mouse sequence probe corresponding to nucleotides 1419 to 1906 of SEQ ID NO: 94 was used and for pc43 a rat sequence probe corresponding to nucleotides 1060 to 1811 of SEQ ID NO: 96 was used. To localize the procadherin 413 gene, a probe including the sequence set out in SEQ ID NO: 37 was used. Other clones used as probes in the current study and RFLVs used to detect anonymous DNA loci were all previously described [Chromosome 7, DNA segment, Washington 12 (D7Was12); the parathyroid hormone (Pth); calcitonin (Calc); hemoglobin, β chain (Hbb); metallothionein-I (Mt-1); adenine phosphoribosyl-transferase (Aprt); growth hormone receptor (Ghr); prostaglandin E receptor EP2 subtype (Ptgerep2); dihydrofolate reductase-2 (Dhfr2); fibroblast growth factor a (Fgfa); and glucocorticoid receptor-1 (Grl-1)].

Comparison of the haplotype distribution of protocadherin genes with those determined for loci throughout the mouse genome allowed each to be mapped to specific regions of mouse chromosomes. The probability for linkage was >99% and indicated assignment of both the pc42 gene and the pc43 gene was chromosome 18. The assignment of the protocadherin 413 gene was chromosome 7. The region of chromosome 18 to which the pc42 and pc43 genes were mapped corresponds to the ataxia (ax) loci [Burt, *Anat. Rec.*, 196: 61–69 (1980) and Lyon, *J. Hered.*, 46: 77–80 (1955)] and twirler (Tw) loci [Lyon, *J. Embryol. Exp. Morphol.*, 6: 105–116 (1958)], while the region of chromosome 7 to which the protocadherin 413 gene was mapped corresponds to the shaker (sh-1) locus [Kikchi et al., *Acta Oto-Laryngol.*, 60: 287–303 (1965) and Lord et al., *Am. Nat.*, 63: 453–442 (1929)]. These loci have been implicated as involved in hereditary neural disease in the mouse. This result is consistent with in situ hybridization results (see Example 12) showing that pc42 and pc43 are strongly expressed in the brain and particularly in the cerebellum.

EXAMPLE 4

Two additional novel human protocadherin cDNAs and one additional novel rat protocadherin cDNA were isolated using rat protocadherin fragments described in Example 1 as probes.

Initially, the rat clone RAT-214 (SEQ ID NO: 7) was used as a probe to screen a rat brain cDNA library (Stratagene, La Jolla, Calif.). The final washing step was performed twice at 50° C. in 0.1×SSC with 0.1% SDS for 15 minutes. Various clones were identified which contained partial cDNA inserts encoding related protocadherin amino acid sequences. The nucleotide sequence of one novel rat clone designated #6-2 is set out in SEQ ID NO: 108. The first fifteen nucleotides of SEQ ID NO: 108 are the sequence of a linker and are not part of the rat #6-2 clone.

A human fetal brain cDNA library obtained from Stratagene was screened with the 0.7 kbp PstI fragment of clone #6-2. The fragment appears to encode the EC-2 and EC-3 of the rat protocadherin. After screening about 2×10⁶ phages, eleven positive clones were isolated. Sequencing of the clones idenitifled a novel full length human protocadherin cDNA designated human pc3. The nucleotide and deduced amino acid sequence of human pc3 are set out in SEQ ID NOs: 109 and 110.

The 0.7 kbp PstI fragment of rat clone #6-2 was also used to rescreen the Stratagene rat brain cDNA library for full length rat cDNA clones. A clone containing an insert encoding a full length novel protocadherin cDNA was isolated. The DNA and deduced amino acid sequence of the insert are set out in SEQ ID NO: 111 and 112. The fill length rat cDNA was named pc5 because it does not appear to be the homolog of the human pc3 clone based upon a comparison of the sequences.

Concurrently, the 0.8 kbp Eco RI-Pst I fragment of partial rat cDNA designated #43 (SEQ ID NO: 113), which was obtained by screening the Stratagene rat brain cDNA library with a probe corresponding to the human pc43 cytoplasmic domain, was used to probe the Stratagene human cDNA library for full length human protocadherin cDNAs. The fragment appears to encode EC-3 through the beginning of EC-6 of clone #43. One partial clone identified encodes a novel human protocadherin named human pc4. The nucleotide sequence and deduced amino acid sequences of the human pc4 clone are set out in SEQ ID NOs: 114 and 115. The amino acid sequence encoded by the pc4 clone appears to begin in the middle of EC-2 of pc4 and continues through the cytoplasmic tail of the protocadherin.

EXAMPLE 5

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pc43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 6

Rabbit polyclonal antibodies specific for pc42 and pc43 were generated as well as a mouse monoclonal antibody specific for pc43.

Preparation of Polyclonal Antibodies Specific for pc42 and pc43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Biolabs, Beverly, Mass.) which contains sequences encoding maltose binding protein immediately upstream of the multicloning site. The resulting plasmids were then introduced into *E. coli* NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 μg of purified fusion protein in Freund's complete adjuvant. Subsequent immunizations with 100 μg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purifim fusion protein with CNBr Sepharose (Pharmacia). Reactivity of the polyclonal sera with purified pc42 fusion protein and pc42 transfected cell extracts (described in Example 5) was confirmed.

Preparation of Monoclonal Antibodies Specific for pc43

The pc43 fusion protein (containing the EC-3 through EC-5 subdomains of pc43) was used to generate monoclonal antibodies in mice according to the method of Kennett, *Methods in Enzyumol.*, 58:345–359 (1978). Briefly, mice were immunized with the pc43 fusion protein (100 μg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc3 extracellular domains were subcloned. The hybridoma cell line designated 3812C (ATCC HB 11207) produced a IgG₁ subtype monoclonal antibody specific for pc43. Reactivity of the monoclonal antibody produced by hybridoma cell line 38I2C to pc43 was confirmed by immunoblotting the pc43 L cell transfectants described in Example 5. The 38I2C monoclonal antibody is specific for human pc43.

EXAMPLE 7

L cells transfected with DNA sequences encoding pc42 and pc43 as prepared in Example 5 were assayed for expression of the protocadherins by immunoblot and by immunofluorescence microscopy.

Immunoblot Analysis

Cell extracts of pc42 and pc43 transfectants were subjected to SDS-PAGE and then blotted electrophoretically onto a PVDF membrane (Minwipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (38I2C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence Microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1% BSA for 30 minutes and then with anti-pc42 polyclonal antibody or anti-pc43 monoclonal antibody in TBS containing 1% BSA for 1 hour at room temperature. Cover slips were then washed with TBS containing 0.01% BSA and respectively incubated with FITC-conjugated anti-rabbit antibody or anti-mouse antibody (Cappel, Durham, N.C.) for 60 minutes at room temperature. The cells were washed again with TBS containing 0.01% BSA and subjected to fluorescence microscopy. Both pc42-specific and pc43-specific polyclonal antibodies stained the cell periphery of transfected cells expressing the protocadherin proteins, mainly at the cell-cell contact sites. The antibodies did not stain the parent L cells, nor did rabbit preimmune sera stain the pc42 and pc43 transfectants.

EXAMPLE 8

The cell aggregation properties of the transfected L cells expressing protocadherin proteins were examined. Transfected L cells were cultured in Dulbecco's Modified Eagles Medium (DMEM) (Gibco, Grand Island, N.Y.) supplemented with 10% fetal bovine serum at 37° C. in 5% $CO_2$. Cells grown near confluence were treated with 0.01% trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., *Dev. Biol.*, 70: 206–216 (1979)] was performed by incubating the resuspended cells in a 1:1 mixture of DMEM and HBS containing 1% BSA, 2 mM $CaCl_2$ and 20 μg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested. When pc43 transfectants labelled with DiO (Molecular Probes, Eugene, Oreg.) were incubated with unlabelled pc42 transfectants in the cell aggregation assay, aggregation of labelled and unlabelled cells was almost mutually exclusive indicating that protocadherin binding is homophilic.

In view of the fact that the protocadherin cytoplasmic domains exhibit no apparent homology to cadherin domains, experiments were performed to determine if the difference in cytoplasmic domains could account for the difference in cell aggregation activity observed in cadherin and protocadherin transfectants. The cytoplasmic domain of pc43 was replaced with the cytoplasmic domain of E-cadherin and aggregation of cells transfected with the chimeric construct was analyzed.

The Bluescript SK(+) clone described in Example 2 which contained the entire coding sequence for pc43 was digested with EcoRV and then partially digested with XbaI to remove the sequence corresponding to the cytoplasmic domain, and the plasmid DNA was purified by agarose gel electrophoresis. The cDNA corresponding to the cytoplasmic domain of mouse E-cadherin was synthesized by PCR using mouse cDNA made from mouse lung mRNA as a template and specific primers corresponding to a region near the N-terminus of the cytoplasmic domain sequence or the region containing the stop codon of mouse E-cadherin (Nagafuchi et al., supra). A XbaI sequence was included to the 5' end of the upstream primer. The E-cadherin cytoplasmic domain cDNA was then subcloned into the linearized pc43 Bluescript clone. The DNA containing the entire resulting chimeric sequence was cut out with SpeI and EcoRV and was subcloned into the SpeI-blunted XbaI site of the expression vector pRc/RSV vector. Finally, L cells were transfected with the resultant construct by a calcium phosphate method. After screening with G418 for about 10 days, the transfectants were stained with FITC-labeled 38I2C anti-pc43 antibody and subjected to FACS analysis. A portion of highly labeled cells were isolated and cloned. Transfectants showed a morphology similar to that of parental L cells and the expressed protein was localized at the cell periphery using pc43 antibody for immunofluorescence microscopy.

Cell aggregation activity of the chimeric transfectants was analyzed as follows. The chimeric pc43 transfectants were labeled with DiO for 20 minutes at room temperature. The resultant cells were trypsinized in the presence of 1 mM EGTA and single cell suspension was made. Then, the cells were mixed with unlabeled other type of transfectants and incubated on a rotary shaker for two hours. The results were examined with a fluorescence and a phase contrast microscope apparatus. Antibody inhibition of cell aggregation was examined by incubation of the transfectants in the presence of polyclonal anti-pc43 antibody (100 ng/ml) in the standard assay medium.

In the cell aggregation assay, the chimeric pc43 transfectants showed clear $Ca^{2+}$-dependent cell aggregation within forty minutes of incubation. Cell aggregation was inhibited by the addition of pc43-specific polyclonal antibody.

EXAMPLE 9

The procedures of Maruyama et al., *J. Biochem.*, 95: 511–519 (1984) were used to determine the calcium binding properties of pc43 by Western blot analysis in the presence or absence of calcium-45. The pc43 fusion protein described in Example 6 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2\pm}$ binding motifs found in E-cadherin. [See, Ringwald et al., *EMBO J.*, 6: 3647–3653 (1987).]

EXAMPLE 10

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, *Proc. Natl. Acad. Sci. USA*, 77: 5201–5205 (1980). The final wash was in 0.2×standard saline citrate containing 0.1% sodium dodecyl sulfate at 65° C. for 10 minutes.

Protocadherin mRNA Expression in Adult Rat Tissues

Total mRNA preparations of rat tissues including brain, heart, liver, lung, skin, kidney and muscle were separated electrophoretically under denaturing conditions (10 μg mRNA/lane) and transferred onto nitrocellulose filters. The filters were hybridized with $^{32}$P-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental Expression of Protocadherin mRNA in Rat Brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with mactin expression.

Protocadherin mRNA Expression in Human Cell Lines

Several neuronal and glial cell lines (including human SK-N-SH neuroblastoma, human U251 glioma, and mouse Neuro-2a neuroblastoma cell lines) were assayed by Northern blot using ⁻P-labelled for expression of pc42 and pc43 mRNA. Human cell lines were probed with HUMAN-742 (which corresponds to EC-4 of human pc42) and HUMAN-43 (which corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 11

Expression of pc43 protein in various tissues, extracts and cells was assayed by Western blot and immunofluorescence microscopy.

Expression in Rat Cardiac Muscle Extracts

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_2$] and microfuging for 15 minutes. Samples were separated by SDS/PAGE and electrophoretically transferred to nitrocellulose (Towbin et al., *PNAS* 76: 4350–4354, 1979). Two pc43 protein bands with molecular weights of 150 KDa and 140 KDa were detected with rabbit polyclonal antibodies to pc43 by the immunoblot method described in Example 7.

Expression in Tissue Sections and Cells

To determine the localization of the protocadherins in various tissues, human and rat adult tissues were removed, incubated in 30% sucrose in PBS for 30 minutes at 4° C., embedded in OCT compound (Cissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in −20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0.1% BSA and incubated with a biotinylated anti-rabbit (Vector Laboratories, Burlingame, Calif.) in 1% BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

A. Muscle

Immunolocalization of pc43 in rat cardiac muscle shows that pc43 is localized in a repeating pattern which is consistent with pc43 being associated with the sarcomeres. Sarcomeres are repetitive contractile units between the fascia adherens in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the fascia adherens junctions at sites of myocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., *J. Cell. Biol,* 117:997–1005 (1992)]. The sarcolemma is connected to the contractile apparatus at the M and Z lines where pc43 is localized.

B. Brain

Reactivity of anti-pc43 polyclonal antibody and monoclonal antibody 38I2C on frozen sections of rat and human cerebellum, respectively, shows that the major sites of pc43 expression are located in Purkinje cells and the granule cell layer which contains numerous small neurons.

C. Placenta

Strong reactivity of monoclonal antibody 38I2C with human syncytiotrophoblasts was also observed in development of the placenta at an early state (5–7 weeks of gestation). Expression appeared to gradually decrease as the stage progressed indicating that pc43 may be involved in the implantation of fertilized eggs into the placenta.

D. Neuroblastoma and Astrocytoma Cells

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the microfilaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

E. Osteoblasts

Immunocytochemical localization of pc43 using monoclonal antibody 38I2C in tow human ostogenic sarcoma cell lines [SaOS (ATCC RTB 85) and MG-63 (ATCC CRL 1427)] and in cultures of normal human trabecular osteoblasts [culture system described in Civitelli et al., *J. Clin. Invest.*, 91: 1888–1896 (1993)] showed that pc43 is expressed in osteoblasts in a pattern similar to that seen in UW28 astrocytoma cells. At sites of cell-cell contact, pc43 is organized in a series of parallel lines that appear to correspond to the actin stress fibers. In addition, in some cells, pc43 appears to localize at the tips of contacting cell processes. Northern blot analysis provides additional evidence that pc43 is expressed in normal human trabecular osteoblasts. A pc43 specific DNA probe hybridized to a major band of 5 kb in samples of poly-A mRNA isolated from normal human trabecular osteoblasts.

EXAMPLE 12

In situ hybridization experiments using protocadherin specific RNA probes were performed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound (Tissue-Tek) in cryomolds and quickly frozen in a bath of 95% ethanol/dry ice. The frozen blocks were stored at −80° C. until cut. Six micron tissue sections were cut using a cryostat (Reichert-Jung, Model #2800 Frigocut N, Leica, Inc., Gilroy, Calif.). Cut tissue sections were stored at −80° C.

The in situ protocol used was a variation of that described by Angerer et al., *Methods in Enzymology*, 152: 649–660, (1987). All solutions were treated with diethylpyrocarbonate (DEPC, Sigma, St. Louis, Mo.) to remove RNase contamination. The tissue sections were first fixed in 4% paraformaldehyde at 4° C. for 20 minutes. To remove excess paraformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at room temperature for 10 minutes. To denature all RNA in the tissue, the sections were placed in a solution of 70% formamide/2×SSC (0.15 M NaCl/0.3 M Na citrate, pH 7.0) at 70° C. for 2 minutes after which they were rinsed in chilled 2×SSC, dehydrated in a graded series of alcohols and then dried. Once dried, the sections were prehybridized in hybridization buffer [50% formamide/50 mM DTT (dithiothrietol)/0.3M NaCl/20 mM Tris, pH 8.0/5 mM EDTA/1×Denhardt's (0.02% Ficoll Type 400/0.02% polyvinylpyrrolidone/0.02% BSA)/10% Dextran Sulfate] at the final hybridization temperature for approximately 4 hours. After prehybridization, approximately $1\times10^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4×SSC to remove the bulk of the hybridization solution and probe. Next a 15 minute wash in 4×SSC/50 mM DTT was carried out at room temperature. Washes at increased stringencies were also utilized. A 40 minute wash in 50% formamide/2×SSC/50 mM DTT was performed at 60° C. Four final room temperature washes were carried out for 10 minutes each: two in 2×SSC and two in 0.1×SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in dH$_2$O. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brian was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was analyzed in brains and spinal chords from rats having EAE (experimental allergic encephalomyelitis) [Vandenbark et al., *Cell. Immunol.*, 12: 85–93 (1974)], the same structures as described above were found to be positive. In addition, expression of pc42 was observed in the leukocytic infiltrates in the EAE tissues. Expression of pc42 in leukocytes was confirmed by in situ hybridization analysis of two leukocytic cell lines, RBL-1 and y3.

Expression of both protocadherin-42 and -43 was observed in the developing brain of rat embryos at all embryological days tested (E15–E19). In addition protocadherin-43 was observed in the developing rat heart at all embryological days tested (E13–E19). This finding is consistent with the immunohistochemistry results showing protocadherin-43 expression in adult heart.

To determine possible roles of protocadherins in the development of the nervous system, expression profiles of protocadherin members in developing rat brain and adult rat brain were also examined by in situ hybridization. A series of coronal, sagittal and horizontal sections of rat brains at postnatal days 0, 6, 14, 30 (P0 through P30) and at 3 months (young adult) were hybridized with labelled cRNA probes corresponding to various protocadherins of the invention including pc42, pc43, RAT-212, RAT-411, and RAT-418. In developing brain, RAT-411 was expressed at high levels in neurons of the olfactory bulb, i.e., mitral cells and periglomerular cells. The expression of RAT-411 mRNA was transient; expression appeared at P0, peaked at P6, diminished by P14, and was undetectable at P30 and in adult brain. In the adult, pc43 mRNA was found to be expressed predominantly in Purkinje cells in the cerebellum. The expression of pc43 mRNA in Purkinje cells was observed from the beginning of Purkinje cell differentiation at around P6. Other protocadherin members were expressed at very low levels in various areas of developing and adult brains. These results indicate that protocadherin members are differentially expressed during the development of the central nervous system, and suggest that RAT-411 and pc43 have specific roles during the development of olfactory bulb neurons and Purkinje cells, respectively.

EXAMPLE 13

Conventional immunoprecipitations using pc43-specific polyclonal antibodies and monoclonal antibody 38I2C were performed to identify proteins that interacted with pc43 in L cell transfectants.

The pc43 and chimeric pc43 transfectants were metabolically labeled by incubating the cells in Dulbecco's modified Eagle's medium containing [$^{35}$S] methionine (50 uCi/ml) overnight. After washing, the transfectants were lysed with PBS containing Tritonx100 and incubated with anti-pc43 antibody. The immunocomplexes were then collected using protein A-Sepharose beads. The resulting beads were washed five times with a washing buffer (50 mM Tris-HCl, pH 8.0, containing 0.5M NaCl, 0.1% ovalbumin, 0.5% NP-40, 0.5% Tritonx100 and 1 mM EDTA) at room temperature. Protein was separated by SDS-PAGE and subjected to autoradiography.

The chimeric pc43 co-precipitated with 105 kDa and a 95 kDa bands that are likely to correspond to α- and β-catenins, respectively, because anti-α-catenin and anti-β-catenin antibodies stained comparable bands. Pc43, on the other hand, co-precipitated with a 120 kDa band.

While the present invention has been described in terms of specific methods and compositions, it is understood that variations and modifications will occur to those skilled in the art. Therefore, only such limitations as appear in the claims should be placed on the invention.

What is claimed is:

1. A method for antagonizing the homophilic binding activity of protocadherin-42 comprising the amino acid sequence set out in SEQ ID NO: 95, wherein said method comprises contacting said protocadherin with an antibody substance specific for said protocadherin thereby antagonizing the homophilic binding of said protocadherin.

* * * * *

UNITED STATES PATENT AND TRADEMARK OFFICE
CERTIFICATE OF CORRECTION

PATENT NO. : 6,262,237 B1
DATED : July 17, 2001
INVENTOR(S) : Shintaro Suzuki

It is certified that error appears in the above-identified patent and that said Letters Patent is hereby corrected as shown below:

Title page,
Item [56], References Cited, Hatta et al., replace "(March 1998)" with
-- (March 1988) --.
Item [56], References Cited, Lord et al., replace "453-442" with -- 435-442 --.

Column 1,
Line 49, replace "an cytoplasmic" with -- a cytoplasmic --.

Column 3,
Line 52, replace "Pariawn Drive" with -- Parklawn Drive --.

Column 4,
Line 58, replace "(amino acids 42-818) of SEQ ID NO: 95)," with -- (amino acids 42-818 of SEQ ID NO: 95), --.

Column 7,
Line 11, replace "Human43" with -- Human-43 --.

Column 12,
Line 29, replace "purifim" with -- purified --.
Line 37, replace "Enzyumol" with -- Enzymol --.
Line 44, replace "pc3" with -- pc43 --.
Line 45, replace "3812C" with -- 38I2C --.
Line 61, replace "Minwipore, Bedford" with -- Millipore, Bedford --.

Column 15,
Line 57, replace "mactin expression" with -- B-actin expression --.
Line 62, replace "= P-labeled" with -- 32 P-labeled --.
Line 63, replace "Human-742" with -- Human-42 --.

UNITED STATES PATENT AND TRADEMARK OFFICE
CERTIFICATE OF CORRECTION

PATENT NO. : 6,262,237 B1
DATED : July 17, 2001
INVENTOR(S) : Shintaro Suzuki

It is certified that error appears in the above-identified patent and that said Letters Patent is hereby corrected as shown below:

Column 16,
Line 27, replace "(Cissue-Tek)" with -- (Tissue-Tek) --.

Column 17,
Line 35, replace "(ATCC RTB 85)" with -- ATCC HTB 85) --.

Signed and Sealed this

Sixth Day of August, 2002

Attest:

Attesting Officer

JAMES E. ROGAN
Director of the United States Patent and Trademark Office

```
                           SEQUENCE LISTING (1) GENERAL INFORMATION:

(iii) NUMBER OF SEQUENCES: 115

(2) INFORMATION FOR SEQ ID NO: 1:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO: 1:

AARSSNNTNG AYTRYGA                                                      17

(2) INFORMATION FOR SEQ ID NO: 2:

(i) SEQUENCE CHARACTERISTICS:
           (A) LENGTH: 17 base pairs
           (B) TYPE: nucleic acid
           (C) STRANDEDNESS: single
           (D) TOPOLOGY: linear
```

(ii) MOLECULE TYPE: DNA (xi) SEQUENCE DESCRIPTION: SEQ ID NO: 2:

TTRCTRTTRC GNGGNNN                                                      17

(2) INFORMATION FOR SEQ ID NO: 3:

(i) SEQUENCE CHARACTERISTICS:
            (A) LENGTH: 131 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

AAGGGAGTGG ACTTTGAGGA GCAGCCTGAG CTTAGTCTCA TCCTCACGGC TTTGGATGGA        60

GGGACTCCAT CCAGGTCTGG GACTGCATTG GTTCAAGTGG AAGTCATAGA TGCCAATGAC       120

AACGCACCGT A                                                            131

(2) INFORMATION FOR SEQ ID NO: 4:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 4:

Lys Gly Val Asp Phe Glu Glu Gln Pro Glu Leu Ser Leu Ile Leu Thr
1               5                  10                  15

Ala Leu Asp Gly Gly Thr Pro Ser Arg Ser Gly Thr Ala Leu Val Gln
            20                  25                  30

Val Glu Val Ile Asp Ala Asn Asp Asn Ala Pro
        35                  40

(2) INFORMATION FOR SEQ ID NO: 5:

(i) SEQUENCE CHARACTERISTICS:
            (A) LENGTH: 131 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

AAACGCATGG ATTTCGAGGA GTCTTCCTCC TACCAGATCT ATGTGCAAGC TACTGACCGG        60

GGACCAGTAC CCATGGCGGG TCATTGCAAG GTGTTGGTGG ACATTATAGA TGTGAACGAC       120

AACGCACCTA A                                                            131

(2) INFORMATION FOR SEQ ID NO: 6:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 6:

```
Lys Ala Met Asp Phe Glu Glu Ser Ser Tyr Gln Ile Tyr Val Gln
 1               5                  10                  15

Ala Thr Asp Arg Gly Pro Val Pro Met Ala Gly His Cys Lys Val Leu
                20                  25                  30

Val Asp Ile Ile Asp Val Asn Asp Asn Ala Pro
            35                  40
```

(2) INFORMATION FOR SEQ ID NO: 7:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
AAGCGACTGG ACTTTGAGAC CCTGCAGACC TTCGAGTTCA GCGTGGGTGC CACAGACCAT      60

GGCTCCCCCT CGCTCCGCAG TCAGGCTCTG GTGCGCGTGG TGGTGCTGGA CCACAATGAC     120

AATGCCCCCA A                                                          131
```

(2) INFORMATION FOR SEQ ID NO: 8:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Lys Arg Leu Asp Phe Glu Thr Leu Gln Thr Phe Glu Phe Ser Val Gly
 1               5                  10                  15

Ala Thr Asp His Gly Ser Pro Ser Leu Arg Ser Gln Ala Leu Val Arg
                20                  25                  30

Val Val Val Leu Asp His Asn Asp Asn Ala Pro
            35                  40
```

(2) INFORMATION FOR SEQ ID NO: 9:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
AAGGGCCTGG ATTACGAGGC ACTGCAGTCC TTCGAGTTCT ACGTGGGCGC TACAGATGGA      60

GGCTCACCCG CGCTCAGCAG CCAGACTCTG GTGCGGATGG TGGTGCTGGA TGACAACGAC     120

AACGCCCCTA A                                                          131
```

(2) INFORMATION FOR SEQ ID NO: 10:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Lys Gly Leu Asp Tyr Glu Ala Leu Gln Ser Phe Glu Phe Tyr Val Gly
1               5                   10                  15

Ala Thr Asp Gly Gly Ser Pro Ala Leu Ser Ser Gln Thr Leu Val Arg
            20                  25                  30

Met Val Val Leu Asp Asp Asn Asp Asn Ala Pro
        35                  40

(2) INFORMATION FOR SEQ ID NO: 11:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

AAGGCGTTTG ATTTTGAGGA TCAGAGAGAG TTCCAGCTAA CCGCTCATAT AAACGACGGA      60

GGTACCCCGG TTTTGGCCAC CAACATCAGC GTGAACATAT TTGTTACTGA CCGCAATGAC    120

AACGCCCCGC A                                                         131

(2) INFORMATION FOR SEQ ID NO: 12:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Lys Ala Phe Asp Phe Glu Asp Gln Arg Glu Phe Gln Leu Thr Ala His
1               5                   10                  15

Ile Asn Asp Gly Gly Thr Pro Val Leu Ala Thr Asn Ile Ser Val Asn
            20                  25                  30

Ile Phe Val Thr Asp Arg Asn Asp Asn Ala Pro
        35                  40

(2) INFORMATION FOR SEQ ID NO: 13:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

AAGGCGGTGG ATTACGAAAT CACCAAGTCC TATGAGATAG ATGTTCAAGC CCAAGATCTG      60

GGTCCCAATT CTATTCCTGC TCATTGCAAA ATTATAATTA AGGTCGTGGA TGTCAACGAC    120

AACGCTCCCA A                                                         131

(2) INFORMATION FOR SEQ ID NO: 14:

(i) SEQUENCE CHARACTERISTICS:
        (A) LENGTH: 43 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO: 14:

Lys Ala Val Asp Tyr Glu Ile Thr Lys Ser Tyr Glu Ile Asp Val Gln
1               5                   10                  15

Ala Gln Asp Leu Gly Pro Asn Ser Ile Pro Ala His Cys Lys Ile Ile
            20                  25                  30

Ile Lys Val Val Asp Val Asn Asp Asn Ala Pro
        35                  40

(2) INFORMATION FOR SEQ ID NO: 15:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TATGACCATG ATTACGAGAC AACCAAAGAA TATACACTGC GGATCCGGGC CCAGGATGGT      60

GGCCGGACTC CACTTTCCAA CGTCTCCGGT CTAGTAACCG TGCAGGTCCT AGACATCAAC     120

GACAATGCCC CCCCA                                                      135

(2) INFORMATION FOR SEQ ID NO: 16:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Tyr Asp His Asp Tyr Glu Thr Thr Lys Glu Tyr Thr Leu Arg Ile Arg
1               5                   10                  15

Ala Gln Asp Gly Gly Arg Thr Pro Leu Ser Asn Val Ser Gly Leu Val
            20                  25                  30

Thr Val Gln Val Leu Asp Ile Asn Asp Asn Ala Pro
        35                  40

(2) INFORMATION FOR SEQ ID NO: 17:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GGGGGGTCGA TTACGAGGAG AACGGCATGT TAGAGATCGA CGTGCAGGCC AGAGACCTAG      60

GACCTAACCC AATTCCAGCC CATTGCAAGG TCACAGTCAA GCTCATCGAC CGCAATGATA     120

ACGCCCCCA                                                             129

(2) INFORMATION FOR SEQ ID NO: 18:

(i) SEQUENCE CHARACTERISTICS:

(A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

Arg Gly Val Asp Tyr Glu Glu Asn Gly Met Leu Glu Ile Asp Val Gln
1               5                   10                  15

Ala Arg Asp Leu Gly Pro Asn Pro Ile Pro Ala His Cys Lys Val Thr
            20                  25                  30

Val Lys Leu Ile Asp Arg Asn Asp Asn Ala Pro
        35                  40

(2) INFORMATION FOR SEQ ID NO: 19:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

AAGGGGTTGG ACTACGAAGA CACCAAACTC CATGAGATTT ACATCCAGGC CAAAGACAAA        60

GGTGCCAATC CGGAAGGAGC GCATTGCAAA GTACTGGTAG AGGTTGTGGA CGTTAACGAC       120

AATGCCCCTC A                                                            131

(2) INFORMATION FOR SEQ ID NO: 20:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Lys Gly Leu Asp Tyr Glu Asp Thr Lys Leu His Glu Ile Tyr Ile Gln
1               5                   10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
        35                  40

(2) INFORMATION FOR SEQ ID NO: 21:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

AAGGGTTTGG ACTTTGAGCA AGTAGATGTC TACAAAATCC GCGTTGACGC GACGGACAAA        60

GGACACCCTC CGATGGCAGG CCATTGCACT GTTTTAGTGA GGGTATTGGA TGAAAACGAC       120

AATGCGCCTC T                                                            131

(2) INFORMATION FOR SEQ ID NO: 22:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

```
Lys Gly Leu Asp Phe Glu Gln Val Asp Val Tyr Lys Ile Arg Val Asp
1               5                   10                  15

Ala Thr Asp Lys Gly His Pro Pro Met Ala Gly His Cys Thr Val Leu
            20                  25                  30

Val Arg Val Leu Asp Glu Asn Asp Asn Ala Pro
        35                  40
```

(2) INFORMATION FOR SEQ ID NO: 23:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

```
AAGGGTATAG ACTTCGAGCA GATCAAGGAC TTCAGCTTTC AAGTGGAAGC CCGGGACGCC      60

GGCAGTCCCC AGGCGCTGTC CGGCAACTGC ACTGTCAACA TCTTGATAGT GGATCAGAAC     120

GACAACGCCC CTAA                                                      134
```

(2) INFORMATION FOR SEQ ID NO: 24:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 24:

```
Lys Gly Ile Asp Phe Glu Gln Ile Lys Asp Phe Ser Phe Gln Val Glu
1               5                   10                  15

Ala Arg Asp Ala Gly Ser Pro Gln Ala Leu Ala Gly Asn Thr Thr Val
            20                  25                  30

Asn Ile Leu Ile Val Asp Gln Asn Asp Asn Ala Pro
        35                  40
```

(2) INFORMATION FOR SEQ ID NO: 25:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
AAGCCGTTCG ACTATGAGCA AACCGCCAAC ACGCTGGCAC AGATTGACGC CGTGCTGGAA      60

AAACAGGGCA GCAATAAATC GAGCATTCTG GATGCCACCA TTTTCCTGGC CGATAAAAAC     120
```

GACAATGCGC CAGA                                                                  134

(2) INFORMATION FOR SEQ ID NO: 26:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Lys Pro Phe Asp Tyr Glu Gln Thr Ala Asn Thr Leu Ala Gln Ile Asp
1               5                   10                  15

Ala Val Leu Glu Lys Gln Gly Ser Asn Lys Ser Ser Ile Leu Asp Ala
            20                  25                  30

Thr Ile Phe Leu Ala Asp Lys Asn Asp Asn Ala Pro
        35                  40

(2) INFORMATION FOR SEQ ID NO: 27:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

AAGCGGCTGG ATTTCGAACA GTTCCAGCAG CACAAGCTGC TCGTAAGGGC TGTTGATGGA        60

GGAATGCCGC CACTGAGCAG CGATGTGGTC GTCACTGTGG ATGTCACCGA CCTCAACGAT       120

AACGCGCCCT A                                                            131

(2) INFORMATION FOR SEQ ID NO: 28:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 28:

Lys Arg Leu Asp Phe Glu Gln Phe Gln Gln His Lys Leu Leu Val Arg
1               5                   10                  15

Ala Val Asp Gly Gly Met Pro Pro Leu Ser Ser Asp Val Val Thr
            20                  25                  30

Val Asp Val Thr Asp Leu Asn Asp Asn Ala Pro
        35                  40

(2) INFORMATION FOR SEQ ID NO: 29:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

AAGGGGATAG ACTTTGAGAG TGAGAATTAC TATGAATTTG ATGTGCGGGC TCGCGATGGG        60

```
GGTTCTCCAG CCATGGAGCA ACATTGCAGC CTTCGAGTGG ATCTGCTGGA CGTAAATGAC      120

AACGCCCCAC T                                                           131
```

(2) INFORMATION FOR SEQ ID NO: 30:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:

```
Lys Gly Ile Asp Phe Glu Ser Glu Asn Tyr Tyr Glu Phe Asp Val Arg
 1               5                  10                  15

Ala Arg Asp Gly Gly Ser Pro Ala Met Glu Gln His Cys Ser Leu Arg
            20                  25                  30

Val Asp Leu Leu Asp Val Asn Asp Asn Ala Pro
            35                  40
```

(2) INFORMATION FOR SEQ ID NO: 31:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

```
AAGGCATTGG ACTTTGAGGC CCGGCGACTG TATTCGCTGA CAGTTCAGGC CACGGACCGA       60

GGCGTGCCCT CGCTCACCGG GCGTGCCGAA GCGCTTATCC AGCTGCTAGA TGTCAACGAC      120

AACGCACCCA T                                                           131
```

(2) INFORMATION FOR SEQ ID NO: 32:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

```
Lys Ala Leu Asp Phe Glu Ala Arg Arg Leu Tyr Ser Leu Thr Val Gln
 1               5                  10                  15

Ala Thr Asp Arg Gly Val Pro Ser Leu Thr Gly Arg Ala Glu Ala Leu
            20                  25                  30

Ile Gln Leu Leu Asp Val Asn Asp Asn Ala Pro
            35                  40
```

(2) INFORMATION FOR SEQ ID NO: 33:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

```
AAGCCAATTG ATTACGAGGC AACTCCATAC TATAACATGG AAATTGTAGC CACAGACAGC      60

GGAGGTCTTT CGGGAAAATG CACTGTGTCT ATACAGGTGG TGGATGTGAA CGACAACGCC     120

CCCAA                                                                 125
```

(2) INFORMATION FOR SEQ ID NO: 34:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

```
Lys Pro Ile Asp Tyr Glu Ala Thr Pro Tyr Tyr Asn Met Glu Ile Val
1               5                   10                  15

Ala Thr Asp Ser Gly Gly Leu Ser Gly Lys Cys Thr Val Ser Ile Gln
                20                  25                  30

Val Val Asp Val Asn Asp Asn Ala Pro
                35                  40
```

(2) INFORMATION FOR SEQ ID NO: 35:

(i) SEQUENCE CHARACTERISTICS:
        (A) LENGTH: 446 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
AAGCGGGTAG ACTTCGAAAT GTGCAAAAGA TTTTACCTTG TGGTGGAAGC TAAAGACGGA      60

GGCACCCCAG CCCTCAGCAC GGCAGCCACT GTCAGCATCG ACCTCACAGA TGTGAATGAT     120

AACCCTCCTC GGTTCAGCCA AGATGTCTAC AGTGCTGTCA TCAGTGAGGA TGCCTTAGAG     180

GGGGACTCTG TCATTCTGCT GATAGCAGAA GATGTGGATA GCAAGCCTAA TGGACAGATT     240

CGGTTTTCCA TCGTGGGTGG AGATAGGGAC AATGAATTTG CTGTCGATCC AATCTTGGGA     300

CTTGTGAAAG TTAAGAAGAA ACTGGACCGG GAGCGGGTGT CAGGATACTC CCTGCTCATC     360

CAGGCAGTAG ATAGTGGCAT TCCTGCAATG TCCTCAACGA CAACTGTCAA CATTGATATT     420

TCTGATGTGA ACGACAACGC CCCCCT                                         446
```

(2) INFORMATION FOR SEQ ID NO: 36:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

```
Lys Arg Val Asp Phe Glu Met Cys Lys Arg Phe Tyr Leu Val Val Glu
1               5                   10                  15

Ala Lys Asp Gly Gly Thr Pro Ala Leu Ser Thr Ala Ala Thr Val Ser
                20                  25                  30

Ile Asp Leu Thr Asp Val Asn Asp Asn Pro Pro Arg Phe Ser Gln Asp
```

|     |     |     |     | 35  |     |     |     | 40  |     |     |     | 45  |     |     |
| --- | --- | --- | --- | --- | --- | --- | --- | --- | --- | --- | --- | --- | --- | --- |
| Val | Tyr | Asp | Ala | Val | Ile | Ser | Glu | Asp | Ala | Leu | Glu | Gly | Asp | Ser | Val |
|     |     |     |     | 50  |     |     |     | 55  |     |     |     | 60  |     |     |     |

Ile Leu Leu Ile Ala Glu Asp Val Asp Ser Lys Pro Asn Gly Gln Ile
65                  70                  75                  80

Arg Phe Ser Ile Val Gly Gly Asp Arg Asp Asn Glu Phe Ala Val Asp
                85                  90                  95

Pro Ile Leu Gly Leu Val Lys Val Lys Lys Leu Asp Arg Glu Arg
                100                 105                 110

Val Ser Gly Tyr Ser Leu Leu Ile Gln Ala Val Asp Ser Gly Ile Pro
                115                 120                 125

Ala Met Ser Ser Thr Thr Thr Val Asn Ile Asp Ile Ser Asp Val Asn
            130                 135                 140

Asp Asn Ala Pro
145

(2) INFORMATION FOR SEQ ID NO: 37:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

```
AAGGGGGTTG ATTATGAGAC AAACCCACGG CTACGACTGG TGCTACAGGC AGAGAGTGGA      60
GGAGCCTTTG CTTTCTCGGT GCTGACCCTG ACCCTTCAAG ATGCCAATGA CAATGCTCCC     120
CGTTTCCTGC AGCCTCACTA CGTGGCTTTC CTGCCAGAGT CCCGACCCTT GGAAGGGCCC     180
CTGCTGCAGG TGGAAGCAGA CGACCTGGAT CAAGGCTCTG GAGGACAGAT CTCCTACAGT     240
CTGGCTGCAT CCCAGCCAGC ACGGGGCTTG TTCCATGTAG ACCCAGCCAC AGGCACTATC     300
ACTACCACAG CCATCCTGGA CCGGGAAATC TGGGCTGAAA CACGGCTGGT ACTGATGGCC     360
ACAGACAGAG GAAGCCCAGC ATTGGTGGGC TCAGCTACCC TGACAGTGAT GGTCATCGAT     420
ACCAACGACA ATGCTCCCCT                                                 440
```

(2) INFORMATION FOR SEQ ID NO: 38:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 38:

Lys Gly Val Asp Tyr Glu Thr Asn Pro Arg Leu Arg Leu Val Leu Gln
1               5                   10                  15

Ala Glu Ser Gly Gly Ala Phe Ala Phe Ser Val Leu Thr Leu Thr Leu
                20                  25                  30

Gln Asp Ala Asn Asp Asn Ala Pro Arg Phe Leu Gln Pro His Tyr Val
                35                  40                  45

Ala Phe Leu Pro Glu Ser Arg Pro Leu Glu Gly Pro Leu Leu Gln Val
                50                  55                  60

Glu Ala Asn Asp Leu Asp Gln Gly Ser Gly Gly Gln Ile Ser Tyr Ser
65                  70                  75                  80

Leu Ala Ala Ser Gln Pro Ala Arg Gly Leu Phe His Val Asp Pro Ala
                85                  90                  95

Thr Gly Thr Ile Thr Thr Thr Ala Ile Leu Asp Arg Glu Ile Trp Ala
            100                 105                 110

Glu Thr Arg Leu Val Leu Met Ala Thr Asp Arg Gly Ser Pro Ala Leu
            115                 120                 125

Val Gly Ser Ala Thr Leu Thr Val Met Val Ile Asp Thr Asn Asp Asn
        130                 135                 140

Ala Pro
145

(2) INFORMATION FOR SEQ ID NO: 39:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

AAGGTCTCGA TTATGAGGCA ACTCCATATT ATAACGTGGA AATTGTAGCC ACAGATGGTG      60

GGGGCCTTTC AGGAAAATGC ACTGTGGCTA TAGAAGTGGT GGATGTGAAC GACGGCGCTC    120

CAAT                                                                 124

(2) INFORMATION FOR SEQ ID NO: 40:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 40:

Lys Gly Leu Asp Tyr Glu Ala Thr Pro Tyr Tyr Asn Val Glu Ile Val
1               5                   10                  15

Ala Thr Asp Gly Gly Ala Phe Asp Glu Asn Cys Thr Val Ala Ile Glu
            20                  25                  30

Val Val Asp Val Asn Asp Asn Ala Pro
        35                  40

(2) INFORMATION FOR SEQ ID NO: 41:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: DNA (xi) SEQUENCE DESCRIPTION: SEQ ID NO: 41:

Asp Xaa Asn Glu Xaa Pro Xaa Phe
1               5

(2) INFORMATION FOR SEQ ID NO: 42:

(i) SEQUENCE CHARACTERISTICS:
        (A) LENGTH: 8 amino acids
        (B) TYPE: amino acid (C) STRANDEDNESS: single
        (D) TOPOLOGY: linear (ii) MOLECULE TYPE: DNA (xi) SEQUENCE DESCRIPTION: SEQ ID NO: 42:

Asp Xaa Asp Glu Xaa Pro Xaa Phe
1               5

(2) INFORMATION FOR SEQ ID NO: 43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: DNA (xi) SEQUENCE DESCRIPTION: SEQ ID NO: 43:

Asp Xaa Asn Asp Asn Xaa Pro Xaa Phe
1               5

(2) INFORMATION FOR SEQ ID NO: 44:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

AAGCGGATGG ATTTTGAAGA CACCAAACTC CATGAGATTT ACATCCAGGC CAAAGACAAA      60

GGTGCCAATC CCGAAGGAGC GCATTGCAAA GTACTTGTAG AGGTTGTAGA CGTAAACGAC     120

AACGCCCCAG T                                                         131

(2) INFORMATION FOR SEQ ID NO: 45:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 45:

Leu Arg Met Asp Phe Glu Asp Thr Lys Leu His Glu Ile Tyr Ile Gln
1               5                   10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
            35                  40

(2) INFORMATION FOR SEQ ID NO: 46:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

AAGGCTTTGG ATTACGAGGA TCAGAGAGAG TTCCAACTAA CAGCTCATAT AAACGACGGA    60

GGTACCCCAG TCTTAGCCAC CAACATCAGC GTGAACGTAT TTGTTACTGA CCGCAATGAT   120

AACGCCCCCT A    131

(2) INFORMATION FOR SEQ ID NO: 47:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:

```
Lys Ala Leu Asp Tyr Glu Asp Gln Arg Glu Phe Gln Leu Thr Ala His
1               5                   10                  15

Ile Asn Asp Gly Gly Thr Pro Val Leu Ala Thr Asn Ile Ser Val Asn
                20                  25                  30

Val Phe Val Thr Asp Arg Asn Asp Asn Ala Pro
                35                  40
```

(2) INFORMATION FOR SEQ ID NO: 48:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

AAGCGCTTGG ACTACGAGGA GAGTAACAAT TATGAAATTC ACGTGGATGC TACAGATAAA    60

GGATACCCAC CTATGGTTGC TCACTGCACC GTACTCGTGG AATCTTGGA TGAAAATGAC   120

AACGCACCCA T    131

(2) INFORMATION FOR SEQ ID NO: 49:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 49:

```
Lys Arg Leu Asp Tyr Glu Glu Ser Asn Asn Tyr Glu Ile His Val Asp
1               5                   10                  15

Ala Thr Asp Lys Gly Tyr Pro Pro Met Val Ala His Cys Thr Val Leu
                20                  25                  30

Val Gly Ile Leu Asp Glu Asn Asp Asn Ala Pro
                35                  40
```

(2) INFORMATION FOR SEQ ID NO: 50:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

AAACCGGTGG ACTACGAGAA AGTCAAAGAC TATACCATCG AGATCGTGGC TGTGGATTCC     60

GGCAACCCTC CACTCTCTAG CACCAACTCC CTCAAGGTGC AGGTGGTAGA CGTCAACGAT    120

AACGCCCCTC T                                                         131

(2) INFORMATION FOR SEQ ID NO: 51:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 51:

Lys Pro Val Asp Tyr Glu Lys Val Lys Asp Tyr Thr Ile Glu Ile Val
1               5                  10                  15

Ala Val Asp Ser Gly Asn Pro Pro Leu Ser Ser Thr Asn Ser Leu Lys
            20                  25                  30

Val Gln Val Val Asp Val Asn Asp Asn Ala Pro
        35                  40

(2) INFORMATION FOR SEQ ID NO: 52:

(i) SEQUENCE CHARACTERISTICS:
            (A) LENGTH: 131 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 52:

AAGCCTTTTG ATTTCGAGGA CACCAAACTC CATGAGATTT ACATCCAGGC CAAAGACAAG     60

GGCGCCAATC CCGAAGGAGC ACATTGCAAA GTGTTGGTGG AGGTTGTGGA TGTGAACGAC    120

AATGCCCCTC A                                                         131

(2) INFORMATION FOR SEQ ID NO: 53:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 53:

Lys Pro Phe Asp Phe Glu Asp Thr Lys Leu His Glu Ile Tyr Ile Gln
1               5                  10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
        35                  40

(2) INFORMATION FOR SEQ ID NO: 54:

(i) SEQUENCE CHARACTERISTICS:
            (A) LENGTH: 122 base pairs
            (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO: 54:

```
AAAGGTGTCG ATTACGAGGT GAGTCCACGG CTGCGACTGG TGCTGCAGGC AGAGAGTCGA      60

GGAGCCTTTG CCTTCACTGT GCTGACCCTG ACCCTGCAAG ATGCCAACGA CAACGCCCCG     120

AG                                                                    122
```

(2) INFORMATION FOR SEQ ID NO: 55:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 55:

```
Lys Gly Val Asp Tyr Glu Val Ser Pro Arg Leu Arg Leu Val Leu Gln
1               5                   10                  15

Ala Glu Ser Arg Gly Ala Phe Ala Phe Thr Val Leu Thr Leu Thr Leu
            20                  25                  30

Gln Asp Ala Asn Asp Asn Ala Pro
        35                  40
```

(2) INFORMATION FOR SEQ ID NO: 56:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

```
AAAGGGATTG ATTACGAGCA GTTGAGAGAC CTACAGCTGT GGGTGACAGC CAGCGACAGC      60

GGGGACCCGC CTCTTAGCAG CAACGTGTCA CTGAGCCTGT TTGTGCTGGA CCAGAACGAC     120

AACGCCCCCC T                                                          131
```

(2) INFORMATION FOR SEQ ID NO: 57:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 57:

```
Lys Gly Ile Asp Tyr Glu Gln Leu Arg Asp Leu Gln Leu Trp Val Thr
1               5                   10                  15

Ala Ser Asp Ser Gly Asp Pro Pro Leu Ser Ser Asn Val Ser Leu Ser
            20                  25                  30

Leu Phe Val Leu Asp Gln Asn Asp Asn Ala Pro
        35                  40
```

(2) INFORMATION FOR SEQ ID NO: 58:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 58:

AAGGCGGTCG ATTTTGAGCG CACATCCTCT TATCAACTCA TCATTCAGGC CACCAATATG        60

GCAGGAATGG CTTCCAATGC TACAGTCAAT ATTCAGATTG TTGATGAAAA CGACAACGCC       120

CCCCA                                                                   125

(2) INFORMATION FOR SEQ ID NO: 59:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 59:

Lys Ala Val Asp Phe Glu Arg Thr Ser Ser Tyr Gln Leu Ile Ile Gln
1               5                  10                  15

Ala Thr Asn Met Ala Gly Met Ala Ser Asn Ala Thr Val Asn Ile Gln
            20                  25                  30

Ile Val Asp Glu Asn Asp Asn Ala Pro
        35                  40

(2) INFORMATION FOR SEQ ID NO: 60:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 60:

AAACGGCTAG ACTTTGAAAA GATACAAAAA TATGTTGTAT GGATAGAGGC CAGAGATGGT        60

GGTTTCCCTC CTTTCTCCTC TTACGAGAAA CTTGATATAA CAGTATTAGA TGTCAACGAT       120

AACGCGCCTA A                                                            131

(2) INFORMATION FOR SEQ ID NO: 61:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 61:

Lys Arg Leu Asp Phe Glu Lys Ile Gln Lys Tyr Val Val Trp Ile Glu
1               5                  10                  15

Ala Arg Asp Gly Gly Phe Pro Pro Phe Ser Ser Tyr Glu Lys Leu Asp
            20                  25                  30

Ile Thr Val Leu Asp Val Asn Asp Asn Ala Pro
        35                  40

(2) INFORMATION FOR SEQ ID NO: 62:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

```
AAGGGGATCG ATTATGAGAA GGTCAAAGAC TACACCATTG AGATTGTGGC TGTGGACTCT      60

GGCAACCCCC CACTCTCCAG CACTAACTCC CTCAAGGTGC AGGTGGTGGA CGTCAATGAC     120

AACGCACCGT G                                                         131
```

(2) INFORMATION FOR SEQ ID NO: 63:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 63:

```
Lys Gly Ile Asp Tyr Glu Lys Val Lys Asp Tyr Thr Ile Glu Ile Val
1               5                   10                  15

Ala Val Asp Ser Gly Asn Pro Pro Leu Ser Ser Thr Asn Ser Leu Lys
            20                  25                  30

Val Gln Val Val Asp Val Asn Asp Asn Ala Pro
        35                  40
```

(2) INFORMATION FOR SEQ ID NO: 64:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

```
AAGGGACTCG ACTACGAGGA TCGGCGGGAA TTTGAATTAA CAGCTCATAT CAGCGATGGG      60

GGCACCCCGG TCCTAGCCAC CAACATCAGC GTGAACATAT TTGTCACTGA TCGCAACGAT     120

AATGCCCCCG T                                                         131
```

(2) INFORMATION FOR SEQ ID NO: 65:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 65:

```
Lys Gly Leu Asp Tyr Glu Asp Arg Arg Glu Phe Glu Leu Thr Ala His
1               5                   10                  15

Ile Ser Asp Gly Gly Thr Pro Val Leu Ala Thr Asn Ile Ser Val Asn
            20                  25                  30
```

Ile Phe Val Thr Asp Arg Asn Asp Asn Ala Pro
          35                  40

(2) INFORMATION FOR SEQ ID NO: 66:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

```
AAGGGTTTGG ACTACGAGAC CACACAGGCC TACCAGCTCA CGGTCAACGC CACAGATCAA      60

GACAACACCA GGCCTCTGTC CACCCTGGCC AACTTGGCCA TCATCATCAC AGATGTCCAG     120

GACATGGACC CCATCTTCAT CAACCTGCCT TACAGCACCA ACATCTACGA GCATTCTCCT     180

CCGGGCACGA CGGTGCGCAT CATCACCGCC ATAGACCAGG ATCAAGGACG TCCCCGGGGC     240

ATTGGCTACA CCATCGTTTC AGGGAATACC AACAGCATCT TTGCCCTGGA CTACATCAGC     300

GGAGTGCTGA CCTTGAATGG CCTGCTGGAC CGGGAGAACC CCCTGTACAG CCATGGCTTC     360

ATCCTGACTG TGAAGGGCAC GGAGCTGAAC GATGACCGCA CCCCATCTGA CGCTACAGTC     420

ACCACGACCT TCAATATCCT GGTTATTGAC ATCAACGACA ACGCCCCACT              470
```

(2) INFORMATION FOR SEQ ID NO: 67:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 67:

Lys Gly Leu Asp Tyr Glu Thr Thr Gln Ala Tyr Gln Leu Thr Val Asn
1               5                   10                  15

Ala Thr Asp Gln Asp Asn Thr Arg Pro Leu Ser Thr Leu Ala Asn Leu
            20                  25                  30

Ala Ile Ile Ile Thr Asp Val Gln Asp Met Asp Pro Ile Phe Ile Asn
        35                  40                  45

Leu Pro Tyr Ser Thr Asn Ile Tyr Glu His Ser Pro Gly Thr Thr
    50                  55                  60

Val Arg Ile Ile Thr Ala Ile Asp Gln Asp Gln Gly Arg Pro Arg Gly
65                  70                  75                  80

Ile Gly Tyr Thr Ile Val Ser Gly Asn Thr Asn Ser Ile Phe Ala Leu
                85                  90                  95

Asp Tyr Ile Ser Gly Val Leu Thr Leu Asn Gly Leu Leu Asp Arg Glu
            100                 105                 110

Asn Pro Leu Tyr Ser Gly Gly Phe Ile Leu Thr Val Lys Gly Thr Glu
        115                 120                 125

Leu Asn Asp Asp Arg Thr Pro Ser Asp Ala Thr Val Thr Thr Thr Phe
    130                 135                 140

Asn Ile Leu Val Ile Asp Ile Asn Asp Asn Ala Pro
145                 150                 155

(2) INFORMATION FOR SEQ ID NO: 68:

(i) SEQUENCE CHARACTERISTICS:

(A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 68:

AAGGGGGTCG ATTACGAGGT ACTACAGGCC TTTGAGTTCC ACGTGAGCGC CACAGACCGA     60

GGCTCACCGG GGCTCAGCAG CCAGGCTCTG GTGCGCGTGG TGGTGCTGGA CGACAATGAC    120

AACGCTCCCG T                                                        131

(2) INFORMATION FOR SEQ ID NO: 69:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 69:

Lys Gly Val Asp Tyr Glu Val Leu Gln Ala Phe Glu Phe His Val Ser
1               5                   10                  15

Ala Thr Asp Arg Gly Ser Pro Gly Leu Ser Ser Gln Ala Leu Val Arg
                20                  25                  30

Val Val Val Leu Asp Asp Asn Asp Asn Ala Pro
            35                  40

(2) INFORMATION FOR SEQ ID NO: 70:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

AAGGGGCTGG ATTATGAGCA GTTCCAGACC CTACAACTGG GAGTGACCGC TAGTGACAGT     60

GGAAACCCAC CATTAAGAAG CAATATTTCA CTGACCCTTT TCGTGCTGGA CCAGAATGAT    120

AACGCCCCAA A                                                        131

(2) INFORMATION FOR SEQ ID NO: 71:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 71:

Lys Gly Leu Asp Tyr Glu Gln Phe Gln Thr Leu Gln Leu Gly Val Thr
1               5                   10                  15

Ala Ser Asp Ser Gly Asn Pro Pro Leu Arg Ser Asn Ile Ser Leu Thr
                20                  25                  30

Leu Phe Val Leu Asp Gln Asn Asp Asn Ala Pro
            35                  40

(2) INFORMATION FOR SEQ ID NO: 72:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 72:

```
AAGCGGGTTG ATTACGAGGA TGTCCAGAAA TACTCGCTGA GCATTAAGGC CCAGGATGGG     60

CGGCCCCCGC TCATCAATTC TTCAGGGGTG GTGTCTGTGC AGGTGCTGGA TGTCAACGAC    120

AATGCCCCGG A                                                         131
```

(2) INFORMATION FOR SEQ ID NO: 73:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 73:

```
Lys Arg Val Asp Tyr Glu Asp Val Gln Lys Tyr Ser Leu Ser Ile Lys
1               5                   10                  15

Ala Gln Asp Gly Arg Pro Pro Leu Ile Asn Ser Ser Gly Val Val Ser
            20                  25                  30

Val Gln Val Leu Asp Val Asn Asp Asn Ala Pro
        35                  40
```

(2) INFORMATION FOR SEQ ID NO: 74:

(i) SEQUENCE CHARACTERISTICS:
       (A) LENGTH: 125 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 74:

```
AAACCGGTAG ACTTTGAGCT ACAGCAGTTC TATGAAGTAG CTGTGGTGGC TTGGAACTCT     60

GAGGGATTTC ATGTCAAAAG GGTCATTAAA GTGCAACTTT TAGATGACAA CGACAATGCC    120

CCGAT                                                                125
```

(2) INFORMATION FOR SEQ ID NO: 75:

(i) SEQUENCE CHARACTERISTICS:
       (A) LENGTH: 41 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 75:

```
Lys Pro Val Asp Phe Glu Leu Gln Gln Phe Tyr Glu Val Ala Val Val
1               5                   10                  15

Ala Trp Asn Ser Glu Gly Phe His Val Lys Arg Val Ile Lys Val Gln
            20                  25                  30

Leu Leu Asp Asp Asn Asp Asn Ala Pro
```

(2) INFORMATION FOR SEQ ID NO: 76:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 76:

```
AAGGGATTAG ATTTTGAAAC TTTGCCCATT TACACATTGA TAATACAAGG AACTAACATG    60
GCTGGTTTGT CCACTAATAC AACGGTTCTA GTTCACTTGC AGGATGAGAA TGATAACGCC   120
CCAAA                                                               125
```

(2) INFORMATION FOR SEQ ID NO: 77:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 77:

```
Lys Gly Leu Asp Phe Glu Thr Leu Pro Ile Tyr Thr Leu Ile Ile Gln
 1               5                  10                  15
Gly Thr Asn Met Ala Gly Leu Ser Thr Asn Thr Thr Val Leu Val His
            20                  25                  30
Leu Gln Asp Glu Asn Asp Asn Ala Pro
        35                  40
```

(2) INFORMATION FOR SEQ ID NO: 78:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

```
AAGCGGGCGG ATTTCGAGGC GATCCGGGAG TACAGTCTGA GGATCAAAGC GCAGGACGGG    60
GGGCGGCCTC CCCTCAGCAA CACCACGGGC ATGGTCACAG TGCAGGTCGT GGACGTCAAT   120
GACAACGCAC CCCT                                                    134
```

(2) INFORMATION FOR SEQ ID NO: 79:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 79:

```
Lys Arg Ala Asp Phe Glu Ala Ile Arg Glu Tyr Ser Leu Arg Ile Lys
 1               5                  10                  15
Ala Gln Asp Gly Gly Arg Pro Pro Leu Ser Asn Thr Thr Gly Met Val
```

```
            20                  25                  30
Thr Val Gln Val Val Asp Val Asn Asp Asn Ala Pro
            35                  40

(2) INFORMATION FOR SEQ ID NO: 80:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 80:

AAGCGGTTGG ATTACGAAAA GGCATCGGAA TATGAAATCT ATGTTCAAGC CGCTGACAAA        60

GGCGCTGTCC CTATGGCTGG CCATTGCAAA GTGTTGCTGG AGATCGTGGA TGTCAACGAC       120

AACGCCCCCT T                                                            131

(2) INFORMATION FOR SEQ ID NO: 81:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 81:

Lys Arg Leu Asp Tyr Glu Lys Ala Ser Glu Tyr Glu Ile Tyr Val Gln
1               5                   10                  15

Ala Ala Asp Lys Gly Ala Val Pro Met Ala Gly His Cys Lys Val Leu
            20                  25                  30

Leu Glu Ile Val Asp Val Asn Asp Asn Ala Pro
            35                  40

(2) INFORMATION FOR SEQ ID NO: 82:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 82:

AAGGGGATCG ATTATGAGGA TCAGGTCTCT TACACATTAG CAGTAACAGC ACATGACTAT        60

GGCATCCCTC AAAAATCAGA CACTACCTAT TTGGAAATCT TAGTAATTGA TGTTAACGAC       120

AACGCGCCCC A                                                            131

(2) INFORMATION FOR SEQ ID NO: 83:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 83:

Lys Gly Ile Asp Tyr Glu Asp Gln Val Ser Tyr Thr Leu Ala Val Thr
```

```
1               5                    10                       15
Ala His Asp Tyr Gly Ile Pro Gln Lys Ser Asp Thr Thr Tyr Leu Glu
                20                  25                30

Ile Leu Val Ile Asp Val Asn Asp Asn Ala Pro
        35                  40
```

(2) INFORMATION FOR SEQ ID NO: 84:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 84:

```
AAAGGGTTAG ATTTCGAGGG CACTAAAGAT TCAGCGTTTA AAATAGTGGC AGCTGACACA      60

GGGAAGCCCA GCCTCAACCA GACAGCCCTG GTGAGAGTAG AGCTGGAGGA TGAGAACGAC     120

AACGCCCCAA T                                                          131
```

(2) INFORMATION FOR SEQ ID NO: 85:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 85:

```
Lys Gly Leu Asp Phe Glu Gly Thr Lys Asp Ser Ala Phe Lys Ile Val
1               5                   10                  15

Ala Ala Asp Thr Gly Lys Pro Ser Leu Asn Gln Thr Ala Leu Val Arg
                20                  25                  30

Val Glu Leu Glu Asp Glu Asn Asp Asn Ala Pro
        35                  40
```

(2) INFORMATION FOR SEQ ID NO: 86:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

```
AAGGGTGTGG ATTTTGAAAG TGTGCGTAGC TACAGGCTGG TTATTCGTGC TCAAGATGGA      60

GGCAGCCCCT CCAGAAGTAA CACCACCCAG CTCTTGGTCA ACGTCATCGA TCGAATGACA     120

ATGCGCCGCT                                                            130
```

(2) INFORMATION FOR SEQ ID NO: 87:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 87:

Lys Gly Val Asp Phe Glu Ser Val Arg Ser Tyr Arg Leu Val Ile Arg
1               5                   10                  15

Ala Gln Asp Gly Gly Ser Pro Ser Arg Ser Asn Thr Thr Gln Leu Leu
            20                  25                  30

Val Asn Val Ile Asp Val Asn Asp Asn Ala Pro
        35                  40

(2) INFORMATION FOR SEQ ID NO: 88:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 88:

```
AAGGGTGTGG ACTTCGAGCT GACACATCTG TATGAGATTT GGATTGAGGC TGCCGATGGA    60

GACACGCCAA GTCTGCGTAG TGTAACTCTT ATAACGCTCA ACGTAACGGA TGCCAATGAC   120

AATGCTCCCA A                                                        131
```

(2) INFORMATION FOR SEQ ID NO: 89:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 89:

Lys Gly Val Asp Phe Glu Leu Thr His Leu Tyr Glu Ile Trp Ile Glu
1               5                   10                  15

Ala Ala Asp Gly Asp Thr Pro Ser Leu Arg Ser Val Thr Leu Ile Thr
            20                  25                  30

Leu Asn Val Thr Asp Ala Asn Asp Asn Ala Pro
        35                  40

(2) INFORMATION FOR SEQ ID NO: 90:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 90:

```
CAAGGCGTTT GATTTTGAAG AGACAAGTAG ATATGTGTTG AGTGTGGAAG CTAAGGATGG    60

AGGAGTACAC ACAGCTCACT GTAATGTTCA AATAGAAATT GTTGACGAGA ATGACAATGC   120

CCCAGAGGTG ACATTCATGT CCTTCTCTAA CCAGATTCCA GAGGATTCAG ACCTTGGAAC   180

TGTAATAGCC CTCATAAAAG TGCGAGACAA GGATTCTGGG CAAAATGGCA TGGTGACATG   240

CTATACTCAG GAAGAAGTTC CTTTCAAATT AGAATCCACC TCGAAGAATT ATTACAAGCT   300

GGTGATTGCT GGAGCCCTAA ACCGGGAGCA GACAGCAGAC TACAACGTCA CAATCATAGC   360

CACCGACAAG GGCAAACCAG CCCTTTCCTC CAGGACAAGC ATCACCCTGC ACATCTCCGA   420
```

CATCAACGAT AATGCCCCCG T                                                              441

(2) INFORMATION FOR SEQ ID NO: 91:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 91:

Lys Ala Phe Asp Phe Glu Glu Thr Ser Arg Tyr Val Leu Ser Val Glu
1               5                   10                  15

Ala Lys Asp Gly Gly Val His Thr Ala His Cys Asn Val Gln Ile Glu
            20                  25                  30

Ile Val Asp Glu Asn Asp Asn Ala Pro Glu Val Thr Phe Met Ser Phe
        35                  40                  45

Ser Asn Gln Ile Pro Glu Asp Ser Asp Leu Gly Thr Val Ile Ala Leu
    50                  55                  60

Ile Lys Val Arg Asp Lys Asp Ser Gly Gln Asn Gly Met Val Thr Cys
65              70                  75                  80

Tyr Thr Gln Glu Glu Val Pro Phe Lys Leu Glu Ser Thr Ser Lys Asn
                85                  90                  95

Tyr Tyr Lys Leu Val Ile Ala Gly Ala Leu Asn Arg Glu Gln Thr Ala
            100                 105                 110

Asp Tyr Asn Val Thr Ile Ile Ala Thr Asp Lys Gly Lys Pro Ala Leu
            115                 120                 125

Ser Ser Arg Thr Ser Ile Thr Leu His Ile Ser Asp Ile Asn Asp Asn
    130                 135                 140

Ala Pro
145

(2) INFORMATION FOR SEQ ID NO: 92:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 92:

AAGCGAGTGG ATTACGAGGC CACTCGGAAT TATAAGCTGA GAGTTAAGGC TACTGATCTT      60

GGGATTCCAC CGAGATCTTC TAACATGACA CTGTTCATTC ATGTCCTTGA TGTTAACGAC     120

AACGCTCCCT T                                                         131

(2) INFORMATION FOR SEQ ID NO: 93:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 93:

Lys Arg Val Asp Tyr Glu Ala Thr Arg Asn Tyr Lys Leu Arg Val Lys
1               5                   10                  15

```
Ala Thr Asp Leu Gly Ile Pro Pro Arg Ser Ser Asn Met Thr Leu Phe
         20                  25                  30

Ile His Val Leu Asp Val Asn Asp Asn Ala Pro
         35                  40

(2) INFORMATION FOR SEQ ID NO: 94:

(i) SEQUENCE CHARACTERISTICS:
        (A) LENGTH: 4104 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 495..3572

(xi) SEQUENCE DESCRIPTION: SEQ ID NO: 94:

CCTCTATTCG ACATTCTCTT TGGATTGTTT TGCTATAACT TGAAATTTGG GATGTCACAA      60

ACGAAACTGT CATCTGTTTC CGCCAAACTG TGGTTCTGCT AATCTCCCAG GCTGGCAGCA     120

TTGGAGACTT GCTGACTTCT TTCATCCCCC ACTCTTTTCA CCTGAAATTC CTTTCCTTGG     180

TTTTGCTCTA AGTCCTATGC TTCAGTCAGG GGCCAACCAA ATCTCACTGC CTCCTTTTTA     240

TCATGAAGCC TTTGATCACT GATAGTTCTT TTTATATCTT GAAAAATCAC CCTTCCCAGT     300

ACAGTTAATA TTTAGTATCT CTACTCATCT TGGCACTTAC TCACAGCTCC ATAATTCAGT     360

CGTTTTCGTA CCTCTTCATG GTGATGGGGA GCCCTTTGGA GGTGGTGACT GTGCTTTATA     420

CTCCTCATGA TGCTTCACAT GTGGCAGGCG TGGAGTGCCC GGAGGCGGCC CTCCTGATTC     480

TGGGGCCTCC CAGG ATG GAG CCC CTG AGG CAC AGC CCA GGC CCT GGG GGG       530
              Met Glu Pro Leu Arg His Ser Pro Gly Pro Gly Gly
                1               5                  10

CAA CGG CTA CTG CTG CCC TCC ATG CTG CTA GCA CTG CTG CTC CTG CTG       578
Gln Arg Leu Leu Leu Pro Ser Met Leu Leu Ala Leu Leu Leu Leu Leu
         15                  20                  25

GCT CCA TCC CCA GGC CAC GCC ACT CGG GTA GTG TAC AAG GTG CCG GAG       626
Ala Pro Ser Pro Gly His Ala Thr Arg Val Val Tyr Lys Val Pro Glu
         30                  35                  40

GAA CAG CCA CCC AAC ACC CTC ATT GGG AGC CTC GCA GCC GAC TAT GGT       674
Glu Gln Pro Pro Asn Thr Leu Ile Gly Ser Leu Ala Ala Asp Tyr Gly
 45                  50                  55                  60

TTT CCA GAT GTG GGG CAC CTG TAC AAG CTA GAG GTG GGT GCC CCG TAC       722
Phe Pro Asp Val Gly His Leu Tyr Lys Leu Glu Val Gly Ala Pro Tyr
                 65                  70                  75

CTT CGC GTG GAT GGC AAG ACA GGT GAC ATT TTC ACC ACC GAG ACC TCC       770
Leu Arg Val Asp Gly Lys Thr Gly Asp Ile Phe Thr Thr Glu Thr Ser
             80                  85                  90

ATC GAC CGT GAG GGG CTC CGT GAA TGC CAG AAC CAG CTC CCT GGT GAT       818
Ile Asp Arg Glu Gly Leu Arg Glu Cys Gln Asn Gln Leu Pro Gly Asp
         95                 100                 105

CCC TGC ATC CTG GAG TTT GAG GTA TCT ATC ACA GAC CTC GTG CAG AAT       866
Pro Cys Ile Leu Glu Phe Glu Val Ser Ile Thr Asp Leu Val Gln Asn
     110                 115                 120

GCG AGC CCC CGG CTG CTA GAG GGC CAG ATA GAA GTA CAA GAC ATC AAT       914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT       962
Asp Asn Thr Pro Asn Phe Ala Ser Pro Val Ile Thr Leu Ala Ile Pro
                145                 150                 155
```

```
GAG AAC ACC AAC ATC GGC TCA CTC TTC CCC ATC CCG CTG GCT TCA GAC      1010
Glu Asn Thr Asn Ile Gly Ser Leu Phe Pro Ile Pro Leu Ala Ser Asp
            160                 165                 170

CGT GAT GCT GGT CCC AAC GGT GTG GCA TCC TAT GAG CTG CAG GTG GCA      1058
Arg Asp Ala Gly Pro Asn Gly Val Ala Ser Tyr Glu Leu Gln Val Ala
            175                 180                 185

GAG GAC CAG GAG GAG AAG CAA CCA CAG CTC ATT GTG ATG GGC AAC CTG      1106
Glu Asp Gln Glu Glu Lys Gln Pro Gln Leu Ile Val Met Gly Asn Leu
            190                 195                 200

GAC CGT GAG CGC TGG GAC TCC TAT GAC CTC ACC ATC AAG GTG CAG GAT      1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG      1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG      1250
Leu Asp Thr Asn Asp Asn Ala Pro Lys Phe Glu Arg Pro Ser Tyr Glu
            240                 245                 250

GCC GAA CTA TCT GAG AAT AGC CCC ATA GGC CAC TCG GTC ATC CAG GTG      1298
Ala Glu Leu Ser Glu Asn Ser Pro Ile Gly His Ser Val Ile Gln Val
            255                 260                 265

AAG GCC AAT GAC TCA GAC CAA GGT GCC AAT GCA GAA ATC GAA TAC ACA      1346
Lys Ala Asn Asp Ser Asp Gln Gly Ala Asn Ala Glu Ile Glu Tyr Thr
270                 275                 280

TTC CAC CAG GCG CCC GAA GTT GTG AGG CGT CTT CTT CGA CTG GAC AGG      1394
Phe His Gln Ala Pro Glu Val Val Arg Arg Leu Leu Arg Leu Asp Arg
285                 290                 295                 300

AAC ACT GGA CTT ATC ACT GTT CAG GGC CCG GTG GAC CGT GAG GAC CTA      1442
Asn Thr Gly Leu Ile Thr Val Gln Gly Pro Val Asp Arg Glu Asp Leu
                305                 310                 315

AGC ACC CTG CGC TTC TCA GTG CTT GCT AAG GAC CGA GGC ACC AAC CCC      1490
Ser Thr Leu Arg Phe Ser Val Leu Ala Lys Asp Arg Gly Thr Asn Pro
            320                 325                 330

AAG AGT GCC CGT GCC CAG GTG GTT GTG ACC GTG AAG GAC ATG AAT GAC      1538
Lys Ser Ala Arg Ala Gln Val Val Val Thr Val Lys Asp Met Asn Asp
            335                 340                 345

AAT GCC CCC ACC ATT GAG ATC CGG GGC ATA GGG CTA GTG ACT CAT CAA      1586
Asn Ala Pro Thr Ile Glu Ile Arg Gly Ile Gly Leu Val Thr His Gln
350                 355                 360

GAT GGG ATG GCT AAC ATC TCA GAG GAT GTG GCA GAG GAG ACA GCT GTG      1634
Asp Gly Met Ala Asn Ile Ser Glu Asp Val Ala Glu Glu Thr Ala Val
365                 370                 375                 380

GCC CTG GTG CAG GTG TCT GAC CGA GAT GAG GGA GAG AAT GCA GCT GTC      1682
Ala Leu Val Gln Val Ser Asp Arg Asp Glu Gly Glu Asn Ala Ala Val
                385                 390                 395

ACC TGT GTG GTG GCA GGT GAT GTG CCC TTC CAG CTG CGC CAG GCC AGT      1730
Thr Cys Val Val Ala Gly Asp Val Pro Phe Gln Leu Arg Gln Ala Ser
            400                 405                 410

GAG ACA GGC AGT GAC AGC AAG AAG AAG TAT TTC CTG CAG ACT ACC ACC      1778
Glu Thr Gly Ser Asp Ser Lys Lys Lys Tyr Phe Leu Gln Thr Thr Thr
            415                 420                 425

CCG CTA GAC TAC GAG AAG GTC AAA GAC TAC ACC ATT GAG ATT GTG GCT      1826
Pro Leu Asp Tyr Glu Lys Val Lys Asp Tyr Thr Ile Glu Ile Val Ala
430                 435                 440

GTG GAC TCT GGC AAC CCC CCA CTC TCC AGC ACT AAC TCC CTC AAG GTG      1874
Val Asp Ser Gly Asn Pro Pro Leu Ser Ser Thr Asn Ser Leu Lys Val
445                 450                 455                 460

CAG GTG GTG GAC GTC AAT GAC AAC GCA CCT GTC TTC ACT CAG AGT GTC      1922
Gln Val Val Asp Val Asn Asp Asn Ala Pro Val Phe Thr Gln Ser Val
```

|  |  |  |  |  |  |  |  |  |  |  |  |  |  |  |
|---|---|---|---|---|---|---|---|---|---|---|---|---|---|---|
|  |  |  | 465 |  |  |  |  | 470 |  |  |  |  | 475 |  |
| ACT | GAG | GTC | GCC | TTC | CCG | GAA | AAC | AAC | AAG | CCT | GGT | GAA | GTG | ATT | GCT | 1970
| Thr | Glu | Val | Ala | Phe | Pro | Glu | Asn | Asn | Lys | Pro | Gly | Glu | Val | Ile | Ala |
|  |  |  | 480 |  |  |  | 485 |  |  |  |  | 490 |  |  |

GAG ATC ACT GCC AGT GAT GCT GAC TCT GGC TCT AAT GCT GAG CTG GTT   2018
Glu Ile Thr Ala Ser Asp Ala Asp Ser Gly Ser Asn Ala Glu Leu Val
            495             500             505

TAC TCT CTG GAG CCT GAG CCG GCT GCT AAG GGC CTC TTC ACC ATC TCA   2066
Tyr Ser Leu Glu Pro Glu Pro Ala Ala Lys Gly Leu Phe Thr Ile Ser
        510             515             520

CCC GAG ACT GGA GAG ATC CAG GTG AAG ACA TCT CTG GAT CGG GAA CAG   2114
Pro Glu Thr Gly Glu Ile Gln Val Lys Thr Ser Leu Asp Arg Glu Gln
525             530             535             540

CGG GAG AGC TAT GAG TTG AAG GTG GTG GCA GCT GAC CGG GGC AGT CCT   2162
Arg Glu Ser Tyr Glu Leu Lys Val Val Ala Ala Asp Arg Gly Ser Pro
            545             550             555

AGC CTC CAG GGC ACA GCC ACT GTC CTT GTC AAT GTG CTG GAC TGC AAT   2210
Ser Leu Gln Gly Thr Ala Thr Val Leu Val Asn Val Leu Asp Cys Asn
        560             565             570

GAC AAT GAC CCC AAA TTT ATG CTG AGT GGC TAC AAC TTC TCA GTG ATG   2258
Asp Asn Asp Pro Lys Phe Met Leu Ser Gly Tyr Asn Phe Ser Val Met
    575             580             585

GAG AAC ATG CCA GCA CTG AGT CCA GTG GGC ATG GTG ACT GTC ATT GAT   2306
Glu Asn Met Pro Ala Leu Ser Pro Val Gly Met Val Thr Val Ile Asp
    590             595             600

GGA GAC AAG GGG GAG AAT GCC CAG GTG CAG CTC TCA GTG GAG CAG GAC   2354
Gly Asp Lys Gly Glu Asn Ala Gln Val Gln Leu Ser Val Glu Gln Asp
605             610             615             620

AAC GGT GAC TTT GTT ATC CAG AAT GGC ACA GGC ACC ATC CTA TCC AGC   2402
Asn Gly Asp Phe Val Ile Gln Asn Gly Thr Gly Thr Ile Leu Ser Ser
            625             630             635

CTG AGC TTT GAT CGA GAG CAA CAA AGC ACC TAC ACC TTC CAG CTG AAG   2450
Leu Ser Phe Asp Arg Glu Gln Gln Ser Thr Tyr Thr Phe Gln Leu Lys
        640             645             650

GCA GTG GAT GGT GGC GTC CCA CCT CGC TCA GCT TAC GTT GGT GTC ACC   2498
Ala Val Asp Gly Gly Val Pro Pro Arg Ser Ala Tyr Val Gly Val Thr
    655             660             665

ATC AAT GTG CTG GAC GAG AAT GAC AAC GCA CCC TAT ATC ACT GCC CCT   2546
Ile Asn Val Leu Asp Glu Asn Asp Asn Ala Pro Tyr Ile Thr Ala Pro
    670             675             680

TCT AAC ACC TCT CAC AAG CTG CTG ACC CCC CAG ACA CGT CTT GGT GAG   2594
Ser Asn Thr Ser His Lys Leu Leu Thr Pro Gln Thr Arg Leu Gly Glu
685             690             695             700

ACG GTC AGC CAG GTG GCA GCC GAG GAC TTT GAC TCT GGT GTC AAT GCC   2642
Thr Val Ser Gln Val Ala Ala Glu Asp Phe Asp Ser Gly Val Asn Ala
            705             710             715

GAG CTG ATC TAC AGC ATT GCA GGT GGC AAC CCT TAT GGA CTC TTC CAG   2690
Glu Leu Ile Tyr Ser Ile Ala Gly Gly Asn Pro Tyr Gly Leu Phe Gln
        720             725             730

ATT GGG TCA CAT TCA GGT GCC ATC ACC CTG GAG AAG GAG ATT GAG CGG   2738
Ile Gly Ser His Ser Gly Ala Ile Thr Leu Glu Lys Glu Ile Glu Arg
    735             740             745

CGC CAC CAT GGG CTA CAC CGC CTG GTG GTG AAG GTC AGT GAC CGC GGC   2786
Arg His His Gly Leu His Arg Leu Val Val Lys Val Ser Asp Arg Gly
    750             755             760

AAG CCC CCA CGC TAT GGC ACA GCC TTG GTC CAT CTT TAT GTC AAT GAG   2834
Lys Pro Pro Arg Tyr Gly Thr Ala Leu Val His Leu Tyr Val Asn Glu
765             770             775             780

ACT CTG GCC AAC CGC ACG CTG CTG GAG ACC CTC CTG GGC CAC AGC CTG   2882

```
                                                                    -continued Thr Leu Ala Asn Arg Thr Leu Leu Glu Thr Leu Leu Gly His Ser Leu
            785                 790                 795

GAC ACG CCG CTG GAT ATT GAC ATT GCT GGG GAT CCA GAA TAT GAG CGC       2930
Asp Thr Pro Leu Asp Ile Asp Ile Ala Gly Asp Pro Glu Tyr Glu Arg
            800                 805                 810

TCC AAG CAG CGT GGC AAC ATT CTC TTT GGT GTG GTG GCT GGT GTG GTG       2978
Ser Lys Gln Arg Gly Asn Ile Leu Phe Gly Val Val Ala Gly Val Val
            815                 820                 825

GCC GTG GCC TTG CTC ATC GCC CTG GCG GTT CTT GTG CGC TAC TGC AGA       3026
Ala Val Ala Leu Leu Ile Ala Leu Ala Val Leu Val Arg Tyr Cys Arg
            830                 835                 840

CAG CGG GAG GCC AAA AGT GGT TAC CAG GCT GGT AAG AAG GAG ACC AAG       3074
Gln Arg Glu Ala Lys Ser Gly Tyr Gln Ala Gly Lys Lys Glu Thr Lys
845                 850                 855                 860

GAC CTG TAT GCC CCC AAG CCC AGT GGC AAG GCC TCC AAG GGA AAC AAA       3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG       3170
Ser Lys Gly Lys Lys Ser Lys Ser Pro Lys Pro Val Lys Pro Val Glu
            880                 885                 890

GAC GAG GAT GAG GCC GGG CTG CAG AAG TCC CTC AAG TTC AAC CTG ATG       3218
Asp Glu Asp Glu Ala Gly Leu Gln Lys Ser Leu Lys Phe Asn Leu Met
            895                 900                 905

AGC GAT GCC CCT GGG GAC AGT CCC CGC ATC CAC CTG CCC CTC AAC TAC       3266
Ser Asp Ala Pro Gly Asp Ser Pro Arg Ile His Leu Pro Leu Asn Tyr
910                 915                 920

CCA CCA GGC AGC CCT GAC CTG GGC CGC CAC TAT CGC TCT AAC TCC CCA       3314
Pro Pro Gly Ser Pro Asp Leu Gly Arg His Tyr Arg Ser Asn Ser Pro
925                 930                 935                 940

CTG CCT TCC ATC CAG CTG CAG CCC CAG TCA CCC TCA GCC TCC AAG AAG       3362
Leu Pro Ser Ile Gln Leu Gln Pro Gln Ser Pro Ser Ala Ser Lys Lys
                945                 950                 955

CAC CAG GTG GTA CAG GAC CTG CCA CCT GCA AAC ACA TTC GTG GGC ACC       3410
His Gln Val Val Gln Asp Leu Pro Pro Ala Asn Thr Phe Val Gly Thr
            960                 965                 970

GGG GAC ACC ACG TCC ACG GGC TCT GAG CAG TAC TCC GAC TAC AGC TAC       3458
Gly Asp Thr Thr Ser Thr Gly Ser Glu Gln Tyr Ser Asp Tyr Ser Tyr
            975                 980                 985

CGC ACC AAC CCC CCC AAA TAC CCC AGC AAG CAG GTA GGC CAG CCC TTT       3506
Arg Thr Asn Pro Pro Lys Tyr Pro Ser Lys Gln Val Gly Gln Pro Phe
            990                 995                 1000

CAG CTC AGC ACA CCC CAG CCC CTA CCC CAC CCC TAC CAC GGA GCC ATC       3554
Gln Leu Ser Thr Pro Gln Pro Leu Pro His Pro Tyr His Gly Ala Ile
1005                1010                1015                1020

TGG ACC GAG GTG TGG GAG TGATGGAGCA GGTTTACTGT GCCTGCCCGT              3602
Trp Thr Glu Val Trp Glu
                1025

GTTGGGGGCC AGCCTGAGCC AGCAGTGGGA GGTGGGGCCT TAGTGCCTCA CCGGGCACAC     3662

GGATTAGGCT GAGTGAAGAT TAAGGGAGGG TGTGCTCTGT GGTCTCCTCC CTGCCCTCTC     3722

CCCACTGGGG AGAGACCTGT GATTTGCCAA GTCCCTGGAC CCTGGACCAG CTACTGGGCC     3782

TTATGGGTTG GGGGTGGTAG GCAGGTGAGC GTAAGTGGGG AGGGAAATGG GTAAGAAGTC     3842

TACTCCAAAC CTAGGTCTCT ATGTCAGACC AGACCTAGGT GCTTCTCTAG GAGGGAAACA     3902

GGGAGACCTG GGGTCCTGTG GATAACTGAG TGGGGAGTCT GCCAGGGGAG GGCACCTTCC     3962

CATTGTGCCT TCTGTGTGTA TTGTGCATTA ACCTCTTCCT CACCACTAGG CTTCTGGGGC     4022

TGGGTCCCAC ATGCCCTTGA CCCTGACAAT AAAGTTCTCT ATTTTTGGAA AAAAAAAAA     4082
```

AAAAAAAAAA AAAAAAAAAA AA                                              4104

(2) INFORMATION FOR SEQ ID NO: 95:

(i) SEQUENCE CHARACTERISTICS:
        (A) LENGTH: 1026 amino acids
        (B) TYPE: amino acid
        (D) TOPOLOGY: linear (ii) MOLECULE TYPE: protein (xi) SEQUENCE DESCRIPTION: SEQ ID NO: 95:

Met Glu Pro Leu Arg His Ser Pro Gly Pro Gly Gln Arg Leu Leu
 1               5                  10                  15

Leu Pro Ser Met Leu Leu Ala Leu Leu Leu Leu Ala Pro Ser Pro
                20                  25                  30

Gly His Ala Thr Arg Val Val Tyr Lys Val Pro Glu Glu Gln Pro
                35                  40                  45

Asn Thr Leu Ile Gly Ser Leu Ala Ala Asp Tyr Gly Phe Pro Asp
             50                  55                  60

Gly His Leu Tyr Lys Leu Glu Val Gly Ala Pro Tyr Leu Arg Val Asp
 65                  70                  75                  80

Gly Lys Thr Gly Asp Ile Phe Thr Thr Glu Thr Ser Ile Asp Arg Glu
                85                  90                  95

Gly Leu Arg Glu Cys Gln Asn Gln Leu Pro Gly Asp Pro Cys Ile Leu
                100                 105                 110

Glu Phe Glu Val Ser Ile Thr Asp Leu Val Gln Asn Ala Ser Pro Arg
                115                 120                 125

Leu Leu Glu Gly Gln Ile Glu Val Gln Asp Ile Asn Asp Asn Thr Pro
130                 135                 140

Asn Phe Ala Ser Pro Val Ile Thr Leu Ala Ile Pro Glu Asn Thr Asn
145                 150                 155                 160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
                180                 185                 190

Glu Lys Gln Pro Gln Leu Ile Val Met Gly Asn Leu Asp Arg Glu Arg
                195                 200                 205

Trp Asp Ser Tyr Asp Leu Thr Ile Lys Val Gln Asp Gly Gly Ser Pro
210                 215                 220

Pro Arg Ala Thr Ser Ala Leu Leu Arg Val Thr Val Leu Asp Thr Asn
225                 230                 235                 240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
                260                 265                 270

Ser Asp Gln Gly Ala Asn Ala Glu Ile Glu Tyr Thr Phe His Gln Ala
        275                 280                 285

Pro Glu Val Val Arg Arg Leu Leu Arg Leu Asp Arg Asn Thr Gly Leu
        290                 295                 300

Ile Thr Val Gln Gly Pro Val Asp Arg Glu Asp Leu Ser Thr Leu Arg
305                 310                 315                 320

Phe Ser Val Leu Ala Lys Asp Arg Gly Thr Asn Pro Lys Ser Ala Arg
                325                 330                 335

Ala Gln Val Val Val Thr Val Lys Asp Met Asn Asp Asn Ala Pro Thr
                340                 345                 350

```
Ile Glu Ile Arg Gly Ile Gly Leu Val Thr His Gln Asp Gly Met Ala
        355                 360                 365
Asn Ile Ser Glu Asp Val Ala Glu Thr Ala Val Ala Leu Val Gln
    370                 375                 380
Val Ser Asp Arg Asp Glu Gly Glu Asn Ala Ala Val Thr Cys Val Val
385                 390                 395                 400
Ala Gly Asp Val Pro Phe Gln Leu Arg Gln Ala Ser Glu Thr Gly Ser
                405                 410                 415
Asp Ser Lys Lys Lys Tyr Phe Leu Gln Thr Thr Thr Pro Leu Asp Tyr
            420                 425                 430
Glu Lys Val Lys Asp Tyr Thr Ile Glu Ile Val Ala Val Asp Ser Gly
        435                 440                 445
Asn Pro Pro Leu Ser Ser Thr Asn Ser Leu Lys Val Gln Val Val Asp
    450                 455                 460
Val Asn Asp Asn Ala Pro Val Phe Thr Gln Ser Val Thr Glu Val Ala
465                 470                 475                 480
Phe Pro Glu Asn Asn Lys Pro Gly Glu Val Ile Ala Glu Ile Thr Ala
                485                 490                 495
Ser Asp Ala Asp Ser Gly Ser Asn Ala Glu Leu Val Tyr Ser Leu Glu
            500                 505                 510
Pro Glu Pro Ala Ala Lys Gly Leu Phe Thr Ile Ser Pro Glu Thr Gly
        515                 520                 525
Glu Ile Gln Val Lys Thr Ser Leu Asp Arg Glu Gln Arg Glu Ser Tyr
    530                 535                 540
Glu Leu Lys Val Val Ala Ala Asp Arg Gly Ser Pro Ser Leu Gln Gly
545                 550                 555                 560
Thr Ala Thr Val Leu Val Asn Val Leu Asp Cys Asn Asp Asn Asp Pro
                565                 570                 575
Lys Phe Met Leu Ser Gly Tyr Asn Phe Ser Val Met Glu Asn Met Pro
            580                 585                 590
Ala Leu Ser Pro Val Gly Met Val Thr Val Ile Asp Gly Asp Lys Gly
        595                 600                 605
Glu Asn Ala Gln Val Gln Leu Ser Val Glu Gln Asp Asn Gly Asp Phe
    610                 615                 620
Val Ile Gln Asn Gly Thr Gly Thr Ile Leu Ser Ser Leu Ser Phe Asp
625                 630                 635                 640
Arg Glu Gln Gln Ser Thr Tyr Thr Phe Gln Leu Lys Ala Val Asp Gly
                645                 650                 655
Gly Val Pro Pro Arg Ser Ala Tyr Val Gly Val Thr Ile Asn Val Leu
            660                 665                 670
Asp Glu Asn Asp Asn Ala Pro Tyr Ile Thr Ala Pro Ser Asn Thr Ser
        675                 680                 685
His Lys Leu Leu Thr Pro Gln Thr Arg Leu Gly Thr Val Ser Gln
    690                 695                 700
Val Ala Ala Glu Asp Phe Asp Ser Gly Val Asn Ala Glu Leu Ile Tyr
705                 710                 715                 720
Ser Ile Ala Gly Gly Asn Pro Tyr Gly Leu Phe Gln Ile Gly Ser His
                725                 730                 735
Ser Gly Ala Ile Thr Leu Glu Lys Glu Ile Glu Arg Arg His His Gly
            740                 745                 750
Leu His Arg Leu Val Val Lys Val Ser Asp Arg Gly Lys Pro Pro Arg
        755                 760                 765
```

```
Tyr Gly Thr Ala Leu Val His Leu Tyr Val Asn Glu Thr Leu Ala Asn
    770             775             780
Arg Thr Leu Leu Glu Thr Leu Leu Gly His Ser Leu Asp Thr Pro Leu
785             790             795             800
Asp Ile Asp Ile Ala Gly Asp Pro Glu Tyr Glu Arg Ser Lys Gln Arg
            805             810             815
Gly Asn Ile Leu Phe Gly Val Val Ala Gly Val Val Ala Val Ala Leu
            820             825             830
Leu Ile Ala Leu Ala Val Leu Val Arg Tyr Cys Arg Gln Arg Glu Ala
            835             840             845
Lys Ser Gly Tyr Gln Ala Gly Lys Lys Glu Thr Lys Asp Leu Tyr Ala
850             855             860
Pro Lys Pro Ser Gly Lys Ala Ser Lys Gly Asn Lys Ser Lys Gly Lys
865             870             875             880
Lys Ser Lys Ser Pro Lys Pro Val Lys Pro Val Glu Asp Glu Asp Glu
            885             890             895
Ala Gly Leu Gln Lys Ser Leu Lys Phe Asn Leu Met Ser Asp Ala Pro
            900             905             910
Gly Asp Ser Pro Arg Ile His Leu Pro Leu Asn Tyr Pro Pro Gly Ser
            915             920             925
Pro Asp Leu Gly Arg His Tyr Arg Ser Asn Ser Pro Leu Pro Ser Ile
    930             935             940
Gln Leu Gln Pro Gln Ser Pro Ser Ala Ser Lys Lys His Gln Val Val
945             950             955             960
Gln Asp Leu Pro Pro Ala Asn Thr Phe Val Gly Thr Gly Asp Thr Thr
            965             970             975
Ser Thr Gly Ser Glu Gln Tyr Ser Asp Tyr Ser Tyr Arg Thr Asn Pro
            980             985             990
Pro Lys Tyr Pro Ser Lys Gln Val Gly Gln Pro Phe Gln Leu Ser Thr
    995             1000            1005
Pro Gln Pro Leu Pro His Pro Tyr His Gly Ala Ile Trp Thr Glu Val
    1010            1015            1020
Trp Glu
1025

(2) INFORMATION FOR SEQ ID NO: 96:

(i) SEQUENCE CHARACTERISTICS:
        (A) LENGTH: 4705 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..2827

(xi) SEQUENCE DESCRIPTION: SEQ ID NO: 96:

CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG        117
                                                              Met
                                                               1

GTC CCA GAG GCC TGG AGG AGC GGA CTG GTA AGC ACC GGG AGG GTA GTG        165
Val Pro Glu Ala Trp Arg Ser Gly Leu Val Ser Thr Gly Arg Val Val
        5                  10                  15

GGA GTT TTG CTT CTG CTT GGT GCC TTG AAC AAG GCT TCC ACG GTC ATT        213
```

```
Gly Val Leu Leu Leu Leu Gly Ala Leu Asn Lys Ala Ser Thr Val Ile
         20                  25                  30

CAC TAT GAG ATC CCG GAG GAA AGA GAG AAG GGT TTC GCT GTG GGC AAC         261
His Tyr Glu Ile Pro Glu Glu Arg Glu Lys Gly Phe Ala Val Gly Asn
     35                  40                  45

GTG GTC GCG AAC CTT GGT TTG GAT CTC GGT AGC CTC TCA GCC CGC AGG         309
Val Val Ala Asn Leu Gly Leu Asp Leu Gly Ser Leu Ser Ala Arg Arg
 50                  55                  60                  65

TTC CCG GTG GTG TCT GGA GCT AGC CGA AGA TTC TTT GAG GTG AAC CGG         357
Phe Pro Val Val Ser Gly Ala Ser Arg Arg Phe Phe Glu Val Asn Arg
             70                  75                  80

GAG ACC GGA GAG ATG TTT GTG AAC GAC CGT CTG GAT CGA GAG GAG CTG         405
Glu Thr Gly Glu Met Phe Val Asn Asp Arg Leu Asp Arg Glu Glu Leu
                 85                  90                  95

TGT GGG ACA CTG CCC TCT TGC ACT GTA ACT CTG GAG TTG GTA GTG GAG         453
Cys Gly Thr Leu Pro Ser Cys Thr Val Thr Leu Glu Leu Val Val Glu
            100                 105                 110

AAC CCG CTG GAG CTG TTC AGC GTG GAA GTG GTG ATC CAG GAC ATC AAC         501
Asn Pro Leu Glu Leu Phe Ser Val Glu Val Val Ile Gln Asp Ile Asn
        115                 120                 125

GAC AAC AAT CCT GCT TTC CCT ACC CAG GAA ATG AAA TTG GAG ATT AGC         549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
                150                 155                 160

CCC GAT CTG GGA AGC AAC TCT TTA CAA ACC TAT GAG CTG AGC CGA AAT         645
Pro Asp Leu Gly Ser Asn Ser Leu Gln Thr Tyr Glu Leu Ser Arg Asn
            165                 170                 175

GAA TAC TTT GCG CTT CGC GTG CAG ACG CGG GAG GAC AGC ACC AAG TAC         693
Glu Tyr Phe Ala Leu Arg Val Gln Thr Arg Glu Asp Ser Thr Lys Tyr
        180                 185                 190

GCG GAG CTG GTG TTG GAG CGC GCC CTG GAC CGA GAA CGG GAG CCT AGT         741
Ala Glu Leu Val Leu Glu Arg Ala Leu Asp Arg Glu Arg Glu Pro Ser
195                 200                 205

CTC CAG TTA GTG CTG ACG GCG TTG GAC GGA GGG ACC CCA GCT CTC TCC         789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG         837
Ala Ser Leu Pro Ile His Ile Lys Val Leu Asp Ala Asn Asp Asn Ala
                230                 235                 240

CCT GTC TTC AAC CAG TCC TTG TAC CGG GCG CGC GTT CCT GGA GGA TGC         885
Pro Val Phe Asn Gln Ser Leu Tyr Arg Ala Arg Val Pro Gly Gly Cys
            245                 250                 255

ACC TCC GGC ACG CGC GTG GTA CAA GTC CTT GCA ACG GAT CTG GAT GAA         933
Thr Ser Gly Thr Arg Val Val Gln Val Leu Ala Thr Asp Leu Asp Glu
        260                 265                 270

GGC CCC AAC GGT GAA ATT ATT TAC TCC TTC GGC AGC CAC AAC CGC GCC         981
Gly Pro Asn Gly Glu Ile Ile Tyr Ser Phe Gly Ser His Asn Arg Ala
275                 280                 285

GGC GTG CGG CAA CTA TTC GCC TTA GAC CTT GTA ACC GGG ATG CTG ACA        1029
Gly Val Arg Gln Leu Phe Ala Leu Asp Leu Val Thr Gly Met Leu Thr
290                 295                 300                 305

ATC AAG GGT CGG CTG GAC TTC GAG GAC ACC AAA CTC CAT GAG ATT TAC        1077
Ile Lys Gly Arg Leu Asp Phe Glu Asp Thr Lys Leu His Glu Ile Tyr
                310                 315                 320

ATC CAG GCC AAA GAC AAG GGC GCC AAT CCC GAA GGA GCA CAT TGC AAA        1125
Ile Gln Ala Lys Asp Lys Gly Ala Asn Pro Glu Gly Ala His Cys Lys
            325                 330                 335
```

```
GTG TTG GTG GAG GTT GTG GAT GTG AAT GAC AAC GCC CCG GAG ATC ACA        1173
Val Leu Val Glu Val Val Asp Val Asn Asp Asn Ala Pro Glu Ile Thr
        340                 345                 350

GTC ACC TCC GTG TAC AGC CCA GTA CCC GAG GAT GCC TCT GGG ACT GTC        1221
Val Thr Ser Val Tyr Ser Pro Val Pro Glu Asp Ala Ser Gly Thr Val
    355                 360                 365

ATC GCT TTG CTC AGT GTG ACT GAC CTG GAT GCT GGC GAG AAC GGG CTG        1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC        1317
Val Thr Cys Glu Val Pro Pro Gly Leu Pro Phe Ser Leu Thr Ser Ser
                390                 395                 400

CTC AAG AAT TAC TTC ACT TTG AAA ACC AGT GCA GAC CTG GAT CGG GAG        1365
Leu Lys Asn Tyr Phe Thr Leu Lys Thr Ser Ala Asp Leu Asp Arg Glu
            405                 410                 415

ACT GTG CCA GAA TAC AAC CTC AGC ATC ACC GCC CGA GAC GCC GGA ACC        1413
Thr Val Pro Glu Tyr Asn Leu Ser Ile Thr Ala Arg Asp Ala Gly Thr
        420                 425                 430

CCT TCC CTC TCA GCC CTT ACA ATA GTG CGT GTT CAA GTG TCC GAC ATC        1461
Pro Ser Leu Ser Ala Leu Thr Ile Val Arg Val Gln Val Ser Asp Ile
435                 440                 445

AAT GAC AAC CCT CCA CAA TCT TCT CAA TCT TCC TAC GAC GTT TAC ATT        1509
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG        1557
Glu Glu Asn Asn Leu Pro Gly Ala Pro Ile Leu Asn Leu Ser Val Trp
                470                 475                 480

GAC CCC GAC GCC CCG CAG AAT GCT CGG CTT TCT TTC TTT CTC TTG GAG        1605
Asp Pro Asp Ala Pro Gln Asn Ala Arg Leu Ser Phe Phe Leu Leu Glu
                485                 490                 495

CAA GGA GCT GAA ACC GGG CTA GTG GGT CGC TAT TTC ACA ATA AAT CGT        1653
Gln Gly Ala Glu Thr Gly Leu Val Gly Arg Tyr Phe Thr Ile Asn Arg
            500                 505                 510

GAC AAT GGC ATA GTG TCA TCC TTA GTG CCC CTA GAC TAT GAG GAT CGG        1701
Asp Asn Gly Ile Val Ser Ser Leu Val Pro Leu Asp Tyr Glu Asp Arg
515                 520                 525

CGG GAA TTT GAA TTA ACA GCT CAT ATC AGC GAT GGG GGC ACC CCG GTC        1749
Arg Glu Phe Glu Leu Thr Ala His Ile Ser Asp Gly Gly Thr Pro Val
530                 535                 540                 545

CTA GCC ACC AAC ATC AGC GTG AAC ATA TTT GTC ACT GAT CGC AAT GAC        1797
Leu Ala Thr Asn Ile Ser Val Asn Ile Phe Val Thr Asp Arg Asn Asp
                550                 555                 560

AAT GCC CCC CAG GTC CTA TAT CCT CGG CCA GGT GGG AGC TCG GTG GAG        1845
Asn Ala Pro Gln Val Leu Tyr Pro Arg Pro Gly Gly Ser Ser Val Glu
                565                 570                 575

ATG CTG CCT CGA GGT ACC TCA GCT GGC CAC CTA GTG TCA CGG GTG GTA        1893
Met Leu Pro Arg Gly Thr Ser Ala Gly His Leu Val Ser Arg Val Val
            580                 585                 590

GGC TGG GAC GCG GAT GCA GGG CAC AAT GCC TGG CTC TCC TAC AGT CTC        1941
Gly Trp Asp Ala Asp Ala Gly His Asn Ala Trp Leu Ser Tyr Ser Leu
595                 600                 605

TTT GGA TCC CCT AAC CAG AGC CTT TTT GCC ATA GGG CTG CAC ACT GGT        1989
Phe Gly Ser Pro Asn Gln Ser Leu Phe Ala Ile Gly Leu His Thr Gly
610                 615                 620                 625

CAA ATC AGT ACT GCC CGT CCA GTC CAA GAC ACA GAT TCA CCC AGG CAG        2037
Gln Ile Ser Thr Ala Arg Pro Val Gln Asp Thr Asp Ser Pro Arg Gln
                630                 635                 640

ACT CTC ACT GTC TTG ATC AAA GAC AAT GGG GAG CCT TCG CTC TCC ACC        2085
Thr Leu Thr Val Leu Ile Lys Asp Asn Gly Glu Pro Ser Leu Ser Thr
            645                 650                 655
```

-continued

```
ACT GCT ACC CTC ACT GTG TCA GTA ACC GAG GAC TCT CCT GAA GCC CGA    2133
Thr Ala Thr Leu Thr Val Ser Val Thr Glu Asp Ser Pro Glu Ala Arg
            660                 665                 670

GCC GAG TTC CCC TCT GGC TCT GCC CCC CGG GAG CAG AAA AAA AAT CTC    2181
Ala Glu Phe Pro Ser Gly Ser Ala Pro Arg Glu Gln Lys Lys Asn Leu
        675                 680                 685

ACC TTT TAT CTA CTT CTT TCT CTA ATC CTG GTT TCT GTG GGC TTC GTG    2229
Thr Phe Tyr Leu Leu Leu Ser Leu Ile Leu Val Ser Val Gly Phe Val
690                 695                 700                 705

GTC ACA GTG TTC GGA GTA ATC ATA TTC AAA GTT TAC AAG TGG AAG CAG    2277
Val Thr Val Phe Gly Val Ile Ile Phe Lys Val Tyr Lys Trp Lys Gln
            710                 715                 720

TCT AGA GAC CTA TAC CGA GCC CCG GTG AGC TCA CTG TAC CGA ACA CCA    2325
Ser Arg Asp Leu Tyr Arg Ala Pro Val Ser Ser Leu Tyr Arg Thr Pro
        725                 730                 735

GGG CCC TCC TTG CAC GCG GAC GCC GTG CGG GGA GGC CTG ATG TCG CCG    2373
Gly Pro Ser Leu His Ala Asp Ala Val Arg Gly Gly Leu Met Ser Pro
    740                 745                 750

CAC CTT TAC CAT CAG GTG TAT CTC ACC ACG GAC TCC CGC CGC AGC GAC    2421
His Leu Tyr His Gln Val Tyr Leu Thr Thr Asp Ser Arg Arg Ser Asp
755                 760                 765

CCG CTG CTG AAG AAA CCT GGT GCA GCC AGT CCA CTG GCC AGC CGC CAG    2469
Pro Leu Leu Lys Lys Pro Gly Ala Ala Ser Pro Leu Ala Ser Arg Gln
770                 775                 780                 785

AAC ACG CTG CGG AGC TGT GAT CCG GTG TTC TAT AGG CAG GTG TTG GGT    2517
Asn Thr Leu Arg Ser Cys Asp Pro Val Phe Tyr Arg Gln Val Leu Gly
            790                 795                 800

GCA GAG AGC GCC CCT CCC GGA CAG CAA GCC CCG CCC AAC ACG GAC TGG    2565
Ala Glu Ser Ala Pro Pro Gly Gln Gln Ala Pro Pro Asn Thr Asp Trp
        805                 810                 815

CGT TTC TCT CAG GCC CAG AGA CCC GGC ACC AGC GGC TCC CAA AAT GGC    2613
Arg Phe Ser Gln Ala Gln Arg Pro Gly Thr Ser Gly Ser Gln Asn Gly
    820                 825                 830

GAT GAC ACC GGC ACC TGG CCC AAC AAC CAG TTT GAC ACA GAG ATG CTG    2661
Asp Asp Thr Gly Thr Trp Pro Asn Asn Gln Phe Asp Thr Glu Met Leu
835                 840                 845

CAA GCC ATG ATC TTG GCG TCC GCC AGT GAA GCT GCT GAT GGG AGC TCC    2709
Gln Ala Met Ile Leu Ala Ser Ala Ser Glu Ala Ala Asp Gly Ser Ser
850                 855                 860                 865

ACC CTG GGA GGG GGT GCC GGC ACC ATG GGA TTG AGC GCC CGC TAC GGA    2757
Thr Leu Gly Gly Gly Ala Gly Thr Met Gly Leu Ser Ala Arg Tyr Gly
            870                 875                 880

CCC CAG TTC ACC CTG CAG CAC GTG CCC GAC TAC CGC CAG AAT GTC TAC    2805
Pro Gln Phe Thr Leu Gln His Val Pro Asp Tyr Arg Gln Asn Val Tyr
        885                 890                 895

ATC CCA GGC AGC AAT GCA CAC T GACCAACGCA GCTGGCAAGC GGATGGCAAG     2857
Ile Pro Gly Ser Asn Ala His
    900

GCCCAGCAGG TGGCAATGGC AACAAGAAGA AGTCGGCAAG AAGGAGAAGA AGTAACATGG  2917

AGGCCAGGCC AAGAGCCACA GGGCAGCCTC TCCCCGAACC AGCCCAGCTT CTCCTTACCT  2977

GCACCCAGGC CTCAGAGTTT CAGGGCTAAC CCCCAGAATA CTGGTAGGGG CCAAGGCATC  3037

TCCCTTGGAA ACAGAAACAA GTGCCATCAC ACCATCCCTT CCCCAGGTGT AATATCCAAA  3097

GCAGTTCCGC TGGGAACCCC ATCCAATCAG TGGCTGTACC CATTTGGGTA GTGGGGTTCA  3157

TGTAGACACC AAGAACCATT TGCCACACCC CGTTTAGTTA CAGCTGAACC CTCCATCTTC  3217

CAAATCAATC AGGCCCATCC ATCCCATGCC TCCCTCCTCC CCACCCCACT CCAACAGTTC  3277
```

```
CTCTTTCCCG AGTAAGGTGG TTGGGGTGTT GAAGTACCAA GTAACCTACA AGCCTCCTAG    3337

TTCTGAAAAG TTGGAAGGGC ATCATGACCT CTTGGCCTCT CCTTTGATTC TCAATCTTCC    3397

CCCAAAGCAT GGTTTGGTGC CAGCCCCTTC ACCTCCTTCC AGAGCCCAAG ATCAATGCTC    3457

AAGTTTTGGA GGACATGATC ACCATCCCCA TGGTACTGAT GCTTGCTGGA TTTAGGGAGG    3517

GCATTTTGCT ACCAAGCCTC TTCCCAACGC CCTGGGACCA GTCTTCTGTT TTGTTTTTCA    3577

TTGTTTGAGC TTTCCACTGC ATGCCTTGAC TTCCCCCACC TCCTCCTCAA ACAAGAGACT    3637

CCACTGCATG TTCCAAGACA GTATGGGGTG GTAAGATAAG GAAGGGAAGT GTGTGGATGT    3697

GGATGGTGGG GGCATGGACA AAGCTTGACA CATCAAGTTA TCAAGGCCTT GGAGGAGGCT    3757

CTGTATGTCC TCAGGGGACT GACAACATCC TCCAGATTCC AGCCATAAAC CAATAACTAG    3817

GCTGGACCCT TCCCACTACA TAATAGGGCT CAGCCAGGCA GCCAGCTTTG GGCTGAGCTA    3877

ACAGGACCAA TGGATTAACT GGCATTTCAG TCCAAGGAAG CTCGAAGCAG GTTTAGGACC    3937

AGGTCCCCTT GAGAGGTCAG AGGGGCCTCT GTGGGTGCTG GGTACTCCAG AGGTGCCACT    3997

GGTGGAAGGG TCAGCGGAGC CCCAGCAGGA AGGGTGGGCC AGCCAGGCCA TTCTTAGTCC    4057

CTGGGTTGGG GAGGCAGGGA GCTAGGGCAG GGACCAAATG AACAGAAAGT CTCAGCCCAG    4117

GATGGGGCTT CTTCAACAGG CCCCTGCCCT CCTGAAGCCT CAGTCCTTCA CCTTGCCAGG    4177

TGCCGTTTCT CTTCCGTGAA GGCCACTGCC CAGGTCCCCA GTGCGCCCCC TAGTGGCCAT    4237

AGCCTGGTTA AAGTTCCCCA GTGCCTCCTT GTGATAGACC TTCTTCTCCC ACCCCCTTCT    4297

GCCCCTGGGT CCCCGGCCAT CCAGCGGGGC TGCCAGAGAA CCCCAGACCT GCCCTTACAG    4357

TAGTGTAGCG CCCCCTCCCT CTTTCGGCTG GTGTAGAATA GCCAGTAGTG TAGTGCGGTG    4417

TGCTTTTACG TGATGGCGGG TGGGCAGCGG GCGGCGGCGT CCGCGCAGCC GTCTGTCCTT    4477

GATCTGCCCG CGGCGGCCCG TGTTGTGTTT TGTGCTGTGT CCAGCGCTAA GGCGACCCCC    4537

TCCCCCGTAC TGACTTCTCC TATAAGCGCT TCTCTTCGCA TAGTCACGTA GCTCCCACCC    4597

CACCCTCTTC CTGTGTCTCA CGCAAGTTTT ATACTCTAAT ATTTATATGG CTTTTTTTCT    4657

TCGACAAAAA AATAATAAAA CGTTTCTTCT GAAAAAAAAA AAAAAAA              4705
```

(2) INFORMATION FOR SEQ ID NO: 97:

(i) SEQUENCE CHARACTERISTICS:
        (A) LENGTH: 904 amino acids
        (B) TYPE: amino acid
        (D) TOPOLOGY: linear (ii) MOLECULE TYPE: protein (xi) SEQUENCE DESCRIPTION: SEQ ID NO: 97:

```
Met Val Pro Glu Ala Trp Arg Ser Gly Leu Val Ser Thr Gly Arg Val
 1               5                  10                  15

Val Gly Val Leu Leu Leu Leu Gly Ala Leu Asn Lys Ala Ser Thr Val
            20                  25                  30

Ile His Tyr Glu Ile Pro Glu Glu Arg Glu Lys Gly Phe Ala Val Gly
        35                  40                  45

Asn Val Val Ala Asn Leu Gly Leu Asp Leu Gly Ser Leu Ser Ala Arg
    50                  55                  60

Arg Phe Pro Val Val Ser Gly Ala Ser Arg Arg Phe Phe Glu Val Asn
65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
```

-continued

```
                    100                 105                 110
Glu Asn Pro Leu Glu Leu Phe Ser Val Glu Val Ile Gln Asp Ile
                115                 120                 125
Asn Asp Asn Pro Ala Phe Pro Thr Gln Glu Met Lys Leu Glu Ile
130                 135                 140
Ser Glu Ala Val Ala Pro Gly Thr Arg Phe Pro Leu Glu Ser Ala His
145                 150                 155                 160
Asp Pro Asp Leu Gly Ser Asn Ser Leu Gln Thr Tyr Glu Leu Ser Arg
                165                 170                 175
Asn Glu Tyr Phe Ala Leu Arg Val Gln Thr Arg Glu Asp Ser Thr Lys
                180                 185                 190
Tyr Ala Glu Leu Val Leu Glu Arg Ala Leu Asp Arg Glu Arg Glu Pro
                195                 200                 205
Ser Leu Gln Leu Val Leu Thr Ala Leu Asp Gly Gly Thr Pro Ala Leu
                210                 215                 220
Ser Ala Ser Leu Pro Ile His Ile Lys Val Leu Asp Ala Asn Asp Asn
225                 230                 235                 240
Ala Pro Val Phe Asn Gln Ser Leu Tyr Arg Ala Arg Val Pro Gly Gly
                245                 250                 255
Cys Thr Ser Gly Thr Arg Val Val Gln Val Leu Ala Thr Asp Leu Asp
                260                 265                 270
Glu Gly Pro Asn Gly Glu Ile Ile Tyr Ser Phe Gly Ser His Asn Arg
                275                 280                 285
Ala Gly Val Arg Gln Leu Phe Ala Leu Asp Leu Val Thr Gly Met Leu
                290                 295                 300
Thr Ile Lys Gly Arg Leu Asp Phe Glu Asp Thr Lys Leu His Glu Ile
305                 310                 315                 320
Tyr Ile Gln Ala Lys Asp Lys Gly Ala Asn Pro Glu Gly Ala His Cys
                325                 330                 335
Lys Val Leu Val Glu Val Val Asp Val Asn Asp Asn Ala Pro Glu Ile
                340                 345                 350
Thr Val Thr Ser Val Tyr Ser Pro Val Pro Glu Asp Ala Ser Gly Thr
                355                 360                 365
Val Ile Ala Leu Leu Ser Val Thr Asp Leu Asp Ala Gly Glu Asn Gly
                370                 375                 380
Leu Val Thr Cys Glu Val Pro Pro Gly Leu Pro Phe Ser Leu Thr Ser
385                 390                 395                 400
Ser Leu Lys Asn Tyr Phe Thr Leu Lys Thr Ser Ala Asp Leu Asp Arg
                405                 410                 415
Glu Thr Val Pro Glu Tyr Asn Leu Ser Ile Thr Ala Arg Asp Ala Gly
                420                 425                 430
Thr Pro Ser Leu Ser Ala Leu Thr Ile Val Arg Val Gln Val Ser Asp
                435                 440                 445
Ile Asn Asp Asn Pro Pro Gln Ser Ser Gln Ser Ser Tyr Asp Val Tyr
450                 455                 460
Ile Glu Glu Asn Asn Leu Pro Gly Ala Pro Ile Leu Asn Leu Ser Val
465                 470                 475                 480
Trp Asp Pro Asp Ala Pro Gln Asn Ala Arg Leu Ser Phe Phe Leu Leu
                485                 490                 495
Glu Gln Gly Ala Glu Thr Gly Leu Val Gly Arg Tyr Phe Thr Ile Asn
                500                 505                 510
Arg Asp Asn Gly Ile Val Ser Ser Leu Val Pro Leu Asp Tyr Glu Asp
                515                 520                 525
```

-continued

```
Arg Arg Glu Phe Glu Leu Thr Ala His Ile Ser Asp Gly Gly Thr Pro
    530                 535                 540
Val Leu Ala Thr Asn Ile Ser Val Asn Ile Phe Val Thr Asp Arg Asn
545                 550                 555                 560
Asp Asn Ala Pro Gln Val Leu Tyr Pro Arg Pro Gly Gly Ser Ser Val
                565                 570                 575
Glu Met Leu Pro Arg Gly Thr Ser Ala Gly His Leu Val Ser Arg Val
                580                 585                 590
Val Gly Trp Asp Ala Asp Ala Gly His Asn Ala Trp Leu Ser Tyr Ser
            595                 600                 605
Leu Phe Gly Ser Pro Asn Gln Ser Leu Phe Ala Ile Gly Leu His Thr
        610                 615                 620
Gly Gln Ile Ser Thr Ala Arg Pro Val Gln Asp Thr Asp Ser Pro Arg
625                 630                 635                 640
Gln Thr Leu Thr Val Leu Ile Lys Asp Asn Gly Glu Pro Ser Leu Ser
                645                 650                 655
Thr Thr Ala Thr Leu Thr Val Ser Val Thr Glu Asp Ser Pro Glu Ala
                660                 665                 670
Arg Ala Glu Phe Pro Ser Gly Ser Ala Pro Arg Glu Gln Lys Lys Asn
            675                 680                 685
Leu Thr Phe Tyr Leu Leu Leu Ser Leu Ile Leu Val Ser Val Gly Phe
        690                 695                 700
Val Val Thr Val Phe Gly Val Ile Ile Phe Lys Val Tyr Lys Trp Lys
705                 710                 715                 720
Gln Ser Arg Asp Leu Tyr Arg Ala Pro Val Ser Ser Leu Tyr Arg Thr
                725                 730                 735
Pro Gly Pro Ser Leu His Ala Asp Ala Val Arg Gly Gly Leu Met Ser
            740                 745                 750
Pro His Leu Tyr His Gln Val Tyr Leu Thr Thr Asp Ser Arg Arg Ser
        755                 760                 765
Asp Pro Leu Leu Lys Lys Pro Gly Ala Ala Ser Pro Leu Ala Ser Arg
770                 775                 780
Gln Asn Thr Leu Arg Ser Cys Asp Pro Val Phe Tyr Arg Gln Val Leu
785                 790                 795                 800
Gly Ala Glu Ser Ala Pro Pro Gly Gln Gln Ala Pro Pro Asn Thr Asp
                805                 810                 815
Trp Arg Phe Ser Gln Ala Gln Arg Pro Gly Thr Ser Gly Ser Gln Asn
            820                 825                 830
Gly Asp Asp Thr Gly Thr Trp Pro Asn Asn Gln Phe Asp Thr Glu Met
        835                 840                 845
Leu Gln Ala Met Ile Leu Ala Ser Ala Ser Glu Ala Ala Asp Gly Ser
850                 855                 860
Ser Thr Leu Gly Gly Gly Ala Gly Thr Met Gly Leu Ser Ala Arg Tyr
865                 870                 875                 880
Gly Pro Gln Phe Thr Leu Gln His Val Pro Asp Tyr Arg Gln Asn Val
                885                 890                 895
Tyr Ile Pro Gly Ser Asn Ala His
            900
```

(2) INFORMATION FOR SEQ ID NO: 98:

(i) SEQUENCE CHARACTERISTICS:
        (A) LENGTH: 556 amino acids
        (B) TYPE: amino acid (D) TOPOLOGY: linear (ii) MOLECULE TYPE: protein (xi) SEQUENCE DESCRIPTION: SEQ ID NO: 98:

```
Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
                20                  25                  30

Ser Leu Arg Tyr Thr Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe Leu His Gln Val
                100                 105                 110

Trp Asn Gly Ser Val Pro Glu Gly Ser Lys Pro Gly Thr Tyr Val Met
            115                 120                 125

Thr Val Thr Ala Ile Asp Ala Asp Asp Pro Asn Ala Leu Asn Gly Met
        130                 135                 140

Leu Arg Tyr Arg Ile Leu Ser Gln Ala Pro Ser Thr Pro Ser Pro Asn
145                 150                 155                 160

Met Phe Thr Ile Asn Asn Glu Thr Gly Asp Ile Ile Thr Val Ala Ala
                165                 170                 175

Gly Leu Asp Arg Glu Lys Val Gln Gln Tyr Thr Leu Ile Ile Gln Ala
            180                 185                 190

Thr Asp Met Glu Gly Asn Pro Thr Tyr Gly Leu Ser Asn Thr Ala Thr
        195                 200                 205

Ala Val Ile Thr Val Thr Asp Val Asn Asp Asn Pro Pro Glu Phe Thr
        210                 215                 220

Ala Met Thr Phe Tyr Gly Glu Val Pro Glu Asn Arg Val Asp Ile Ile
225                 230                 235                 240

Val Ala Asn Leu Thr Val Thr Asp Lys Asp Gln Pro His Thr Pro Ala
                245                 250                 255

Trp Asn Ala Val Thr Arg Ile Ser Gly Gly Asp Pro Thr Gly Arg Phe
            260                 265                 270

Ala Ile Gln Thr Asp Pro Asn Ser Asn Asp Gly Leu Val Thr Val Val
        275                 280                 285

Lys Pro Ile Asp Phe Glu Thr Asn Arg Met Phe Val Leu Thr Val Ala
290                 295                 300

Ala Glu Asn Gln Val Pro Leu Ala Lys Gly Ile Gln His Pro Pro Gln
305                 310                 315                 320

Ser Thr Ala Thr Val Ser Val Thr Val Ile Asp Val Asn Glu Asn Pro
                325                 330                 335

Tyr Phe Ala Pro Asn Pro Lys Ile Ile Arg Gln Glu Glu Gly Leu His
            340                 345                 350

Ala Gly Thr Met Leu Thr Thr Phe Thr Ala Gly Asp Pro Asp Arg Tyr
        355                 360                 365

Met Gln Gln Asn Ile Arg Tyr Thr Lys Leu Ser Asp Pro Ala Asn Trp
370                 375                 380

Leu Lys Ile Asp Pro Val Asn Gly Gln Ile Thr Thr Ile Ala Val Leu
```

```
                385                 390                 395                 400
Asp Arg Glu Ser Pro Asn Val Lys Asn Asn Ile Tyr Asn Ala Thr Phe
                    405                 410                 415

Leu Ala Ser Asp Asn Gly Ile Pro Pro Met Ser Gly Thr Gly Thr Leu
                    420                 425                 430

Gln Ile Tyr Leu Leu Asp Ile Asn Asp Asn Ala Pro Gln Val Leu Pro
                    435                 440                 445

Gln Glu Ala Glu Thr Cys Glu Thr Pro Asp Pro Asn Ser Ile Asn Ile
                    450                 455                 460

Thr Thr Ala Leu Asp Tyr Asp Ile Asp Pro Asn Ala Gly Pro Phe Ala
465                 470                 475                 480

Tyr Asp Leu Pro Leu Ser Pro Val Thr Ile Lys Arg Asn Trp Thr Ile
                    485                 490                 495

Thr Arg Leu Asn Gly Asp Phe Ala Gln Leu Asn Leu Lys Ile Lys Phe
                    500                 505                 510

Leu Glu Ala Gly Ile Tyr Glu Val Pro Ile Ile Ile Thr Asp Ser Gly
                    515                 520                 525

Asn Pro Pro Lys Ser Asn Lys Ser Ile Leu Arg Val Arg Val Cys Gln
        530                 535                 540

Cys Asp Phe Asn Gly Asp Cys Thr Asp Val Asp Arg
545                 550                 555
```

(2) INFORMATION FOR SEQ ID NO: 99:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 99:

```
Glu Asp Thr Val Tyr Ser Phe Asp Ile Pro Glu Asn Ala Gln Arg Gly
1               5                   10                  15

Tyr Gln Val Gly Gln Ile Val Ala Arg Asp Ala Asp Leu Gly Gln Asn
            20                  25                  30

Ala Gln Leu Ser Tyr Gly Val Val Ser Asp Trp Ala Asn Asp Val Phe
        35                  40                  45

Ser Leu Asn Pro Gln Thr Gly Met Leu Thr Leu Thr Ala Arg Leu Asp
    50                  55                  60

Tyr Glu Glu Val Gln His Tyr Ile Leu Ile Val Gln Ala Gln Asp Asn
65                  70                  75                  80

Gly Gln Pro Ser Leu Ser Thr Thr Ile Thr Val Tyr Cys Asn Val Leu
                85                  90                  95

Asp Leu Asn Asp Asn Ala Pro Ile Phe
                100                 105
```

(2) INFORMATION FOR SEQ ID NO: 100:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 100:

Asp Xaa Asp Xaa Gly Xaa Asn
1               5

(2) INFORMATION FOR SEQ ID NO: 101:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 101:

Ala Xaa Asp Xaa Gly Xaa Pro
1               5

(2) INFORMATION FOR SEQ ID NO: 102:

(i) SEQUENCE CHARACTERISTICS:
        (A) LENGTH: 4650 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 495..4103

(xi) SEQUENCE DESCRIPTION: SEQ ID NO: 102:

```
CCTCTATTCG ACATTCTCTT TGGATTGTTT TGCTATAACT TGAAATTTGG GATGTCACAA        60

ACGAAACTGT CATCTGTTTC CGCCAAACTG TGGTTCTGCT AATCTCCCAG GCTGGCAGCA       120

TTGGAGACTT GCTGACTTCT TTCATCCCCC ACTCTTTTCA CCTGAAATTC CTTTCCTTGG       180

TTTTGCTCTA AGTCCTATGC TTCAGTCAGG GGCCAACCAA ATCTCACTGC CTCCTTTTTA       240

TCATGAAGCC TTTGATCACT GATAGTTCTT TTTATATCTT GAAAAATCAC CCTTCCCAGT       300

ACAGTTAATA TTTAGTATCT CTACTCATCT TGGCACTTAC TCACAGCTCC ATAATTCAGT       360

CGTTTTCGTA CCTCTTCATG GTGATGGGGA GCCCTTTGGA GGTGGTGACT GTGCTTTATA       420

CTCCTCATGA TGCTTCACAT GTGGCAGGCG TGGAGTGCCC GGAGGCGGCC CTCCTGATTC       480

TGGGGCCTCC CAGG ATG GAG CCC CTG AGG CAC AGC CCA GGC CCT GGG GGG         530
              Met Glu Pro Leu Arg His Ser Pro Gly Pro Gly Gly
                1               5                  10

CAA CGG CTA CTG CTG CCC TCC ATG CTG CTA GCA CTG CTC CTG CTG             578
Gln Arg Leu Leu Leu Pro Ser Met Leu Leu Ala Leu Leu Leu Leu
        15                  20                  25

GCT CCA TCC CCA GGC CAC GCC ACT CGG GTA GTG TAC AAG GTG CCG GAG         626
Ala Pro Ser Pro Gly His Ala Thr Arg Val Val Tyr Lys Val Pro Glu
        30                  35                  40

GAA CAG CCA CCC AAC ACC CTC ATT GGG AGC CTC GCA GCC GAC TAT GGT         674
Glu Gln Pro Pro Asn Thr Leu Ile Gly Ser Leu Ala Ala Asp Tyr Gly
 45                  50                  55                  60

TTT CCA GAT GTG GGG CAC CTG TAC AAG CTA GAG GTG GGT GCC CCG TAC         722
Phe Pro Asp Val Gly His Leu Tyr Lys Leu Glu Val Gly Ala Pro Tyr
                65                  70                  75

CTT CGC GTG GAT GGC AAG ACA GGT GAC ATT TTC ACC ACC GAG ACC TCC         770
Leu Arg Val Asp Gly Lys Thr Gly Asp Ile Phe Thr Thr Glu Thr Ser
        80                  85                  90

ATC GAC CGT GAG GGG CTC CGT GAA TGC CAG AAC CAG CTC CCT GGT GAT         818
Ile Asp Arg Glu Gly Leu Arg Glu Cys Gln Asn Gln Leu Pro Gly Asp
        95                  100                 105
```

```
CCC TGC ATC CTG GAG TTT GAG GTA TCT ATC ACA GAC CTC GTG CAG AAT      866
Pro Cys Ile Leu Glu Phe Glu Val Ser Ile Thr Asp Leu Val Gln Asn
        110                 115                 120

GCG AGC CCC CGG CTG CTA GAG GGC CAG ATA GAA GTA CAA GAC ATC AAT      914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT      962
Asp Asn Thr Pro Asn Phe Ala Ser Pro Val Ile Thr Leu Ala Ile Pro
                    145                 150                 155

GAG AAC ACC AAC ATC GGC TCA CTC TTC CCC ATC CCG CTG GCT TCA GAC     1010
Glu Asn Thr Asn Ile Gly Ser Leu Phe Pro Ile Pro Leu Ala Ser Asp
                160                 165                 170

CGT GAT GCT GGT CCC AAC GGT GTG GCA TCC TAT GAG CTG CAG GTG GCA     1058
Arg Asp Ala Gly Pro Asn Gly Val Ala Ser Tyr Glu Leu Gln Val Ala
            175                 180                 185

GAG GAC CAG GAG GAG AAG CAA CCA CAG CTC ATT GTG ATG GGC AAC CTG     1106
Glu Asp Gln Glu Glu Lys Gln Pro Gln Leu Ile Val Met Gly Asn Leu
190                 195                 200

GAC CGT GAG CGC TGG GAC TCC TAT GAC CTC ACC ATC AAG GTG CAG GAT     1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG     1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG     1250
Leu Asp Thr Asn Asp Asn Ala Pro Lys Phe Glu Arg Pro Ser Tyr Glu
                240                 245                 250

GCC GAA CTA TCT GAG AAT AGC CCC ATA GGC CAC TCG GTC ATC CAG GTG     1298
Ala Glu Leu Ser Glu Asn Ser Pro Ile Gly His Ser Val Ile Gln Val
            255                 260                 265

AAG GCC AAT GAC TCA GAC CAA GGT GCC AAT GCA GAA ATC GAA TAC ACA     1346
Lys Ala Asn Asp Ser Asp Gln Gly Ala Asn Ala Glu Ile Glu Tyr Thr
270                 275                 280

TTC CAC CAG GCG CCC GAA GTT GTG AGG CGT CTT CTT CGA CTG GAC AGG     1394
Phe His Gln Ala Pro Glu Val Val Arg Arg Leu Leu Arg Leu Asp Arg
285                 290                 295                 300

AAC ACT GGA CTT ATC ACT GTT CAG GGC CCG GTG GAC CGT GAG GAC CTA     1442
Asn Thr Gly Leu Ile Thr Val Gln Gly Pro Val Asp Arg Glu Asp Leu
                305                 310                 315

AGC ACC CTG CGC TTC TCA GTG CTT GCT AAG GAC CGA GGC ACC AAC CCC     1490
Ser Thr Leu Arg Phe Ser Val Leu Ala Lys Asp Arg Gly Thr Asn Pro
                320                 325                 330

AAG AGT GCC CGT GCC CAG GTG GTT GTG ACC GTG AAG GAC ATG AAT GAC     1538
Lys Ser Ala Arg Ala Gln Val Val Val Thr Val Lys Asp Met Asn Asp
                335                 340                 345

AAT GCC CCC ACC ATT GAG ATC CGG GGC ATA GGG CTA GTG ACT CAT CAA     1586
Asn Ala Pro Thr Ile Glu Ile Arg Gly Ile Gly Leu Val Thr His Gln
350                 355                 360

GAT GGG ATG GCT AAC ATC TCA GAG GAT GTG GCA GAG GAG ACA GCT GTG     1634
Asp Gly Met Ala Asn Ile Ser Glu Asp Val Ala Glu Glu Thr Ala Val
365                 370                 375                 380

GCC CTG GTG CAG GTG TCT GAC CGA GAT GAG GGA GAG AAT GCA GCT GTC     1682
Ala Leu Val Gln Val Ser Asp Arg Asp Glu Gly Glu Asn Ala Ala Val
                385                 390                 395

ACC TGT GTG GTG GCA GGT GAT GTG CCC TTC CAG CTG CGC CAG GCC AGT     1730
Thr Cys Val Val Ala Gly Asp Val Pro Phe Gln Leu Arg Gln Ala Ser
                400                 405                 410

GAG ACA GGC AGT GAC AGC AAG AAG AAG TAT TTC CTG CAG ACT ACC ACC     1778
Glu Thr Gly Ser Asp Ser Lys Lys Lys Tyr Phe Leu Gln Thr Thr Thr
```

```
            415                 420                 425
CCG CTA GAC TAC GAG AAG GTC AAA GAC TAC ACC ATT GAG ATT GTG GCT    1826
Pro Leu Asp Tyr Glu Lys Val Lys Asp Tyr Thr Ile Glu Ile Val Ala
    430                 435                 440

GTG GAC TCT GGC AAC CCC CCA CTC TCC AGC ACT AAC TCC CTC AAG GTG    1874
Val Asp Ser Gly Asn Pro Pro Leu Ser Ser Thr Asn Ser Leu Lys Val
445                 450                 455                 460

CAG GTG GTG GAC GTC AAT GAC AAC GCA CCT GTC TTC ACT CAG AGT GTC    1922
Gln Val Val Asp Val Asn Asp Asn Ala Pro Val Phe Thr Gln Ser Val
                465                 470                 475

ACT GAG GTC GCC TTC CCG GAA AAC AAC AAG CCT GGT GAA GTG ATT GCT    1970
Thr Glu Val Ala Phe Pro Glu Asn Asn Lys Pro Gly Glu Val Ile Ala
            480                 485                 490

GAG ATC ACT GCC AGT GAT GCT GAC TCT GGC TCT AAT GCT GAG CTG GTT    2018
Glu Ile Thr Ala Ser Asp Ala Asp Ser Gly Ser Asn Ala Glu Leu Val
        495                 500                 505

TAC TCT CTG GAG CCT GAG CCG GCT GCT AAG GGC CTC TTC ACC ATC TCA    2066
Tyr Ser Leu Glu Pro Glu Pro Ala Ala Lys Gly Leu Phe Thr Ile Ser
    510                 515                 520

CCC GAG ACT GGA GAG ATC CAG GTG AAG ACA TCT CTG GAT CGG GAA CAG    2114
Pro Glu Thr Gly Glu Ile Gln Val Lys Thr Ser Leu Asp Arg Glu Gln
525                 530                 535                 540

CGG GAG AGC TAT GAG TTG AAG GTG GTG GCA GCT GAC CGG GGC AGT CCT    2162
Arg Glu Ser Tyr Glu Leu Lys Val Val Ala Ala Asp Arg Gly Ser Pro
                545                 550                 555

AGC CTC CAG GGC ACA GCC ACT GTC CTT GTC AAT GTG CTG GAC TGC AAT    2210
Ser Leu Gln Gly Thr Ala Thr Val Leu Val Asn Val Leu Asp Cys Asn
            560                 565                 570

GAC AAT GAC CCC AAA TTT ATG CTG AGT GGC TAC AAC TTC TCA GTG ATG    2258
Asp Asn Asp Pro Lys Phe Met Leu Ser Gly Tyr Asn Phe Ser Val Met
        575                 580                 585

GAG AAC ATG CCA GCA CTG AGT CCA GTG GGC ATG GTG ACT GTC ATT GAT    2306
Glu Asn Met Pro Ala Leu Ser Pro Val Gly Met Val Thr Val Ile Asp
    590                 595                 600

GGA GAC AAG GGG GAG AAT GCC CAG GTG CAG CTC TCA GTG GAG CAG GAC    2354
Gly Asp Lys Gly Glu Asn Ala Gln Val Gln Leu Ser Val Glu Gln Asp
605                 610                 615                 620

AAC GGT GAC TTT GTT ATC CAG AAT GGC ACA GGC ACC ATC CTA TCC AGC    2402
Asn Gly Asp Phe Val Ile Gln Asn Gly Thr Gly Thr Ile Leu Ser Ser
                625                 630                 635

CTG AGC TTT GAT CGA GAG CAA CAA AGC ACC TAC ACC TTC CAG CTG AAG    2450
Leu Ser Phe Asp Arg Glu Gln Gln Ser Thr Tyr Thr Phe Gln Leu Lys
            640                 645                 650

GCA GTG GAT GGT GGC GTC CCA CCT CGC TCA GCT TAC GTT GGT GTC ACC    2498
Ala Val Asp Gly Gly Val Pro Pro Arg Ser Ala Tyr Val Gly Val Thr
        655                 660                 665

ATC AAT GTG CTG GAC GAG AAT GAC AAC GCA CCC TAT ATC ACT GCC CCT    2546
Ile Asn Val Leu Asp Glu Asn Asp Asn Ala Pro Tyr Ile Thr Ala Pro
    670                 675                 680

TCT AAC ACC TCT CAC AAG CTG CTG ACC CCC CAG ACA CGT CTT GGT GAG    2594
Ser Asn Thr Ser His Lys Leu Leu Thr Pro Gln Thr Arg Leu Gly Glu
685                 690                 695                 700

ACG GTC AGC CAG GTG GCA GCC GAG GAC TTT GAC TCT GGT GTC AAT GCC    2642
Thr Val Ser Gln Val Ala Ala Glu Asp Phe Asp Ser Gly Val Asn Ala
                705                 710                 715

GAG CTG ATC TAC AGC ATT GCA GGT GGC AAC CCT TAT GGA CTC TTC CAG    2690
Glu Leu Ile Tyr Ser Ile Ala Gly Gly Asn Pro Tyr Gly Leu Phe Gln
            720                 725                 730

ATT GGG TCA CAT TCA GGT GCC ATC ACC CTG GAG AAG GAG ATT GAG CGG    2738
```

```
Ile Gly Ser His Ser Gly Ala Ile Thr Leu Glu Lys Glu Ile Glu Arg
            735                 740                 745

CGC CAC CAT GGG CTA CAC CGC CTG GTG GTG AAG GTC AGT GAC CGC GGC      2786
Arg His His Gly Leu His Arg Leu Val Val Lys Val Ser Asp Arg Gly
        750                 755                 760

AAG CCC CCA CGC TAT GGC ACA GCC TTG GTC CAT CTT TAT GTC AAT GAG      2834
Lys Pro Pro Arg Tyr Gly Thr Ala Leu Val His Leu Tyr Val Asn Glu
765                 770                 775                 780

ACT CTG GCC AAC CGC ACG CTG CTG GAG ACC CTC CTG GGC CAC AGC CTG      2882
Thr Leu Ala Asn Arg Thr Leu Leu Glu Thr Leu Leu Gly His Ser Leu
                785                 790                 795

GAC ACG CCG CTG GAT ATT GAC ATT GCT GGG GAT CCA GAA TAT GAG CGC      2930
Asp Thr Pro Leu Asp Ile Asp Ile Ala Gly Asp Pro Glu Tyr Glu Arg
            800                 805                 810

TCC AAG CAG CGT GGC AAC ATT CTC TTT GGT GTG GTG GCT GGT GTG GTG      2978
Ser Lys Gln Arg Gly Asn Ile Leu Phe Gly Val Val Ala Gly Val Val
        815                 820                 825

GCC GTG GCC TTG CTC ATC GCC CTG GCG GTT CTT GTG CGC TAC TGC AGA      3026
Ala Val Ala Leu Leu Ile Ala Leu Ala Val Leu Val Arg Tyr Cys Arg
830                 835                 840

CAG CGG GAG GCC AAA AGT GGT TAC CAG GCT GGT AAG AAG GAG ACC AAG      3074
Gln Arg Glu Ala Lys Ser Gly Tyr Gln Ala Gly Lys Lys Glu Thr Lys
845                 850                 855                 860

GAC CTG TAT GCC CCC AAG CCC AGT GGC AAG GCC TCC AAG GGA AAC AAA      3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG      3170
Ser Lys Gly Lys Lys Ser Lys Ser Pro Lys Pro Val Lys Pro Val Glu
            880                 885                 890

GAC GAG GAT GAG GCC GGG CTG CAG AAG TCC CTC AAG TTC AAC CTG ATG      3218
Asp Glu Asp Glu Ala Gly Leu Gln Lys Ser Leu Lys Phe Asn Leu Met
        895                 900                 905

AGC GAT GCC CCT GGG GAC AGT CCC CGC ATC CAC CTG CCC CTC AAC TAC      3266
Ser Asp Ala Pro Gly Asp Ser Pro Arg Ile His Leu Pro Leu Asn Tyr
910                 915                 920

CCA CCA GGC AGC CCT GAC CTG GGC CGC CAC TAT CGC TCT AAC TCC CCA      3314
Pro Pro Gly Ser Pro Asp Leu Gly Arg His Tyr Arg Ser Asn Ser Pro
925                 930                 935                 940

CTG CCT TCC ATC CAG CTG CAG CCC CAG TCA CCC TCA GCC TCC AAG AAG      3362
Leu Pro Ser Ile Gln Leu Gln Pro Gln Ser Pro Ser Ala Ser Lys Lys
                945                 950                 955

CAC CAG GTG GTA CAG GAC CTG CCA CCT GCA AAC ACA TTC GTG GGC ACC      3410
His Gln Val Val Gln Asp Leu Pro Pro Ala Asn Thr Phe Val Gly Thr
            960                 965                 970

GGG GAC ACC ACG TCC ACG GGC TCT GAG CAG TAC TCC GAC TAC AGC TAC      3458
Gly Asp Thr Thr Ser Thr Gly Ser Glu Gln Tyr Ser Asp Tyr Ser Tyr
        975                 980                 985

CGC ACC AAC CCC CCC AAA TAC CCC AGC AAG CAG TTA CCT CAC CGC CGC      3506
Arg Thr Asn Pro Pro Lys Tyr Pro Ser Lys Gln Leu Pro His Arg Arg
990                 995                 1000

GTC ACC TTC TCG GCC ACC AGC CAG GCC CAG GAG CTG CAG GAC CCA TCC      3554
Val Thr Phe Ser Ala Thr Ser Gln Ala Gln Glu Leu Gln Asp Pro Ser
1005                1010                1015                1020

CAG CAC AGT TAC TAT GAC AGT GGC CTG GAG GAG TCT GAG ACG CCG TCC      3602
Gln His Ser Tyr Tyr Asp Ser Gly Leu Glu Glu Ser Glu Thr Pro Ser
                1025                1030                1035

AGC AAG TCA TCC TCA GGG CCT CGA CTC GGT CCC CTG GCC CTG CCT GAG      3650
Ser Lys Ser Ser Ser Gly Pro Arg Leu Gly Pro Leu Ala Leu Pro Glu
            1040                1045                1050
```

```
GAT CAC TAT GAG CGC ACC ACC CCT GAT GGC AGC ATA GGA GAG ATG GAG        3698
Asp His Tyr Glu Arg Thr Thr Pro Asp Gly Ser Ile Gly Glu Met Glu
        1055                1060                1065

CAC CCC GAG AAT GAC CTT CGC CCT TTG CCT GAT GTC GCC ATG ACA GGC        3746
His Pro Glu Asn Asp Leu Arg Pro Leu Pro Asp Val Ala Met Thr Gly
    1070                1075                1080

ACA TGT ACC CGG GAG TGC AGT GAG TTT GGC CAC TCT GAC ACA TGC TGG        3794
Thr Cys Thr Arg Glu Cys Ser Glu Phe Gly His Ser Asp Thr Cys Trp
1085                1090                1095                1100

ATG CCT GGC CAG TCA TCT CCC AGC CGC CGG ACC AAG AGC AGC GCC CTC        3842
Met Pro Gly Gln Ser Ser Pro Ser Arg Arg Thr Lys Ser Ser Ala Leu
            1105                1110                1115

AAA CTC TCC ACC TTC ATG CCT TAC CAG GAC CGA GGA GGG CAG GAG CCT        3890
Lys Leu Ser Thr Phe Met Pro Tyr Gln Asp Arg Gly Gly Gln Glu Pro
        1120                1125                1130

GCG GGC GCC GGC AGC CCC AGC CCC CCG GAA GAC CGG AAC ACC AAA ACG        3938
Ala Gly Ala Gly Ser Pro Ser Pro Pro Glu Asp Arg Asn Thr Lys Thr
    1135                1140                1145

GCC CCC GTG CGC CTC CTG CCC TCC TAC AGT GCC TTC TCC CAC AGT AGC        3986
Ala Pro Val Arg Leu Leu Pro Ser Tyr Ser Ala Phe Ser His Ser Ser
1150                1155                1160

CAT GAT TCC TGC AAG GAC TCG GCC ACC TTG GAG GAA ATC CCC CTG ACC        4034
His Asp Ser Cys Lys Asp Ser Ala Thr Leu Glu Glu Ile Pro Leu Thr
1165                1170                1175                1180

CAG ACC TCG GAC TTC CCA CCC GCA GCC ACA CCG GCA TCT GCC CAG ACG        4082
Gln Thr Ser Asp Phe Pro Pro Ala Ala Thr Pro Ala Ser Ala Gln Thr
            1185                1190                1195

GCC AAG CGC GAG ATC TAC CTG TGAGCCCCCT ACTGGCCGGC CCCCCTCCCC          4133
Ala Lys Arg Glu Ile Tyr Leu
        1200

CAGCGCCGGC CAGCTCCCAA ATGCCCATTC CAGGGCCTCA CTCTCCACCC CTTCAGCGTG      4193

GACTTCCTGC CAGGGCCCAA GTGGGGGTAT CACTGACCTC ATGACCACGC TGGCCCTTCT      4253

CCCATGCAGG GTCCAGGTCC TCTCCCCTCA TTTCCATCTC CCAGCCCAGG GGCCCCTTCC      4313

CCTTTATGGG GCTTCCCCCA GCTGATGCCC AAGAGGGCTC CTCTGCAATG ACTGGGCTCC      4373

TTCCCTTGAC TTCAGGGAG CACCCCCTCG ATTTGGGCAG ATGGTGGAGT CAAGGGTGGG      4433

CAGCGTACTT CTAACTCATT GTTTCCCTCA TGGCCGACCA GGGCGGGGAT AGCATGCCCA      4493

ATTTTAGCCC TGAAGCAGGG CTGAACTGGG GAGCCCCTTT CCCTGGGAGC TCCCAGAGGA      4553

AACTCTTGAC CACCAGTGGC TCCCTGAAGG GCTTTTGTTA CCAAAGGTGG GGTAGGGACG      4613

GGGGTGGGAG TGGAGCGGAG GCCTTGTTTT CCCGTGG                              4650

(2) INFORMATION FOR SEQ ID NO: 103:

(i) SEQUENCE CHARACTERISTICS:
        (A) LENGTH: 1203 amino acids
        (B) TYPE: amino acid
        (D) TOPOLOGY: linear (ii) MOLECULE TYPE: protein (xi) SEQUENCE DESCRIPTION: SEQ ID NO: 103:

Met Glu Pro Leu Arg His Ser Pro Gly Pro Gly Gly Gln Arg Leu Leu
 1               5                  10                  15

Leu Pro Ser Met Leu Leu Ala Leu Leu Leu Leu Ala Pro Ser Pro
            20                  25                  30

Gly His Ala Thr Arg Val Val Tyr Lys Val Pro Glu Glu Gln Pro Pro
        35                  40                  45
```

```
Asn Thr Leu Ile Gly Ser Leu Ala Ala Asp Tyr Gly Phe Pro Asp Val
     50                  55                  60

Gly His Leu Tyr Lys Leu Glu Val Gly Ala Pro Tyr Leu Arg Val Asp
 65                  70                  75                  80

Gly Lys Thr Gly Asp Ile Phe Thr Thr Glu Thr Ser Ile Asp Arg Glu
                 85                  90                  95

Gly Leu Arg Glu Cys Gln Asn Gln Leu Pro Gly Asp Pro Cys Ile Leu
            100                 105                 110

Glu Phe Glu Val Ser Ile Thr Asp Leu Val Gln Asn Ala Ser Pro Arg
        115                 120                 125

Leu Leu Glu Gly Gln Ile Glu Val Gln Asp Ile Asn Asp Asn Thr Pro
    130                 135                 140

Asn Phe Ala Ser Pro Val Ile Thr Leu Ala Ile Pro Glu Asn Thr Asn
145                 150                 155                 160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
            180                 185                 190

Glu Lys Gln Pro Gln Leu Ile Val Met Gly Asn Leu Asp Arg Glu Arg
        195                 200                 205

Trp Asp Ser Tyr Asp Leu Thr Ile Lys Val Gln Asp Gly Gly Ser Pro
    210                 215                 220

Pro Arg Ala Thr Ser Ala Leu Leu Arg Val Thr Val Leu Asp Thr Asn
225                 230                 235                 240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
            260                 265                 270

Ser Asp Gln Gly Ala Asn Ala Glu Ile Glu Tyr Thr Phe His Gln Ala
        275                 280                 285

Pro Glu Val Val Arg Arg Leu Leu Arg Leu Asp Arg Asn Thr Gly Leu
    290                 295                 300

Ile Thr Val Gln Gly Pro Val Asp Arg Glu Asp Leu Ser Thr Leu Arg
305                 310                 315                 320

Phe Ser Val Leu Ala Lys Asp Arg Gly Thr Asn Pro Lys Ser Ala Arg
                325                 330                 335

Ala Gln Val Val Val Thr Val Lys Asp Met Asn Asp Asn Ala Pro Thr
            340                 345                 350

Ile Glu Ile Arg Gly Ile Gly Leu Val Thr His Gln Asp Gly Met Ala
        355                 360                 365

Asn Ile Ser Glu Asp Val Ala Glu Thr Ala Val Ala Leu Val Gln
    370                 375                 380

Val Ser Asp Arg Asp Glu Gly Glu Asn Ala Ala Val Thr Cys Val Val
385                 390                 395                 400

Ala Gly Asp Val Pro Phe Gln Leu Arg Gln Ala Ser Glu Thr Gly Ser
                405                 410                 415

Asp Ser Lys Lys Lys Tyr Phe Leu Gln Thr Thr Pro Leu Asp Tyr
            420                 425                 430

Glu Lys Val Lys Asp Tyr Thr Ile Glu Ile Val Ala Val Asp Ser Gly
        435                 440                 445

Asn Pro Pro Leu Ser Ser Thr Asn Ser Leu Lys Val Gln Val Val Asp
450                 455                 460

Val Asn Asp Asn Ala Pro Val Phe Thr Gln Ser Val Thr Glu Val Ala
```

-continued

```
465                 470                 475                 480
Phe Pro Glu Asn Asn Lys Pro Gly Glu Val Ile Ala Glu Ile Thr Ala
                485                 490                 495
Ser Asp Ala Asp Ser Gly Ser Asn Ala Glu Leu Val Tyr Ser Leu Glu
                500                 505                 510
Pro Glu Pro Ala Ala Lys Gly Leu Phe Thr Ile Ser Pro Glu Thr Gly
                515                 520                 525
Glu Ile Gln Val Lys Thr Ser Leu Asp Arg Glu Gln Arg Glu Ser Tyr
            530                 535                 540
Glu Leu Lys Val Val Ala Ala Asp Arg Gly Ser Pro Ser Leu Gln Gly
545                 550                 555                 560
Thr Ala Thr Val Leu Val Asn Val Leu Asp Cys Asn Asp Asn Asp Pro
                565                 570                 575
Lys Phe Met Leu Ser Gly Tyr Asn Phe Ser Val Met Glu Asn Met Pro
                580                 585                 590
Ala Leu Ser Pro Val Gly Met Val Thr Val Ile Asp Gly Asp Lys Gly
                595                 600                 605
Glu Asn Ala Gln Val Gln Leu Ser Val Glu Gln Asp Asn Gly Asp Phe
            610                 615                 620
Val Ile Gln Asn Gly Thr Gly Thr Ile Leu Ser Ser Leu Ser Phe Asp
625                 630                 635                 640
Arg Glu Gln Gln Ser Thr Tyr Thr Phe Gln Leu Lys Ala Val Asp Gly
                645                 650                 655
Gly Val Pro Pro Arg Ser Ala Tyr Val Gly Val Thr Ile Asn Val Leu
                660                 665                 670
Asp Glu Asn Asp Asn Ala Pro Tyr Ile Thr Ala Pro Ser Asn Thr Ser
                675                 680                 685
His Lys Leu Leu Thr Pro Gln Thr Arg Leu Gly Glu Thr Val Ser Gln
            690                 695                 700
Val Ala Ala Glu Asp Phe Asp Ser Gly Val Asn Ala Glu Leu Ile Tyr
705                 710                 715                 720
Ser Ile Ala Gly Gly Asn Pro Tyr Gly Leu Phe Gln Ile Gly Ser His
                725                 730                 735
Ser Gly Ala Ile Thr Leu Glu Lys Glu Ile Glu Arg His His Gly
                740                 745                 750
Leu His Arg Leu Val Val Lys Val Ser Asp Arg Gly Lys Pro Pro Arg
            755                 760                 765
Tyr Gly Thr Ala Leu Val His Leu Tyr Val Asn Glu Thr Leu Ala Asn
770                 775                 780
Arg Thr Leu Leu Glu Thr Leu Leu Gly His Ser Leu Asp Thr Pro Leu
785                 790                 795                 800
Asp Ile Asp Ile Ala Gly Asp Pro Glu Tyr Glu Arg Ser Lys Gln Arg
                805                 810                 815
Gly Asn Ile Leu Phe Gly Val Ala Gly Val Val Ala Val Ala Leu
            820                 825                 830
Leu Ile Ala Leu Ala Val Leu Val Arg Tyr Cys Arg Gln Arg Glu Ala
            835                 840                 845
Lys Ser Gly Tyr Gln Ala Gly Lys Lys Glu Thr Lys Asp Leu Tyr Ala
            850                 855                 860
Pro Lys Pro Ser Gly Lys Ala Ser Lys Gly Asn Lys Ser Lys Gly Lys
865                 870                 875                 880
Lys Ser Lys Ser Pro Lys Pro Val Lys Pro Val Glu Asp Glu Asp Glu
                885                 890                 895
```

-continued

```
Ala Gly Leu Gln Lys Ser Leu Lys Phe Asn Leu Met Ser Asp Ala Pro
            900                 905                 910
Gly Asp Ser Pro Arg Ile His Leu Pro Leu Asn Tyr Pro Pro Gly Ser
            915                 920                 925
Pro Asp Leu Gly Arg His Tyr Arg Ser Asn Ser Pro Leu Pro Ser Ile
            930                 935                 940
Gln Leu Gln Pro Gln Ser Pro Ser Ala Ser Lys Lys His Gln Val Val
945                 950                 955                 960
Gln Asp Leu Pro Pro Ala Asn Thr Phe Val Gly Thr Gly Asp Thr Thr
                965                 970                 975
Ser Thr Gly Ser Glu Gln Tyr Ser Asp Tyr Ser Tyr Arg Thr Asn Pro
            980                 985                 990
Pro Lys Tyr Pro Ser Lys Gln Leu Pro His Arg Arg Val Thr Phe Ser
            995                 1000                1005
Ala Thr Ser Gln Ala Gln Glu Leu Gln Asp Pro Ser Gln His Ser Tyr
            1010                1015                1020
Tyr Asp Ser Gly Leu Glu Glu Ser Glu Thr Pro Ser Ser Lys Ser Ser
1025                1030                1035                1040
Ser Gly Pro Arg Leu Gly Pro Leu Ala Leu Pro Glu Asp His Tyr Glu
            1045                1050                1055
Arg Thr Thr Pro Asp Gly Ser Ile Gly Glu Met Glu His Pro Glu Asn
            1060                1065                1070
Asp Leu Arg Pro Leu Pro Asp Val Ala Met Thr Gly Thr Cys Thr Arg
            1075                1080                1085
Glu Cys Ser Glu Phe Gly His Ser Asp Thr Cys Trp Met Pro Gly Gln
            1090                1095                1100
Ser Ser Pro Ser Arg Arg Thr Lys Ser Ser Ala Leu Lys Leu Ser Thr
1105                1110                1115                1120
Phe Met Pro Tyr Gln Asp Arg Gly Gly Gln Glu Pro Ala Gly Ala Gly
            1125                1130                1135
Ser Pro Ser Pro Pro Glu Asp Arg Asn Thr Lys Thr Ala Pro Val Arg
            1140                1145                1150
Leu Leu Pro Ser Tyr Ser Ala Phe Ser His Ser Ser His Asp Ser Cys
            1155                1160                1165
Lys Asp Ser Ala Thr Leu Glu Glu Ile Pro Leu Thr Gln Thr Ser Asp
            1170                1175                1180
Phe Pro Pro Ala Ala Thr Pro Ala Ser Ala Gln Thr Ala Lys Arg Glu
1185                1190                1195                1200
Ile Tyr Leu (2) INFORMATION FOR SEQ ID NO: 104:

(i) SEQUENCE CHARACTERISTICS:
        (A) LENGTH: 2789 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..2622

(xi) SEQUENCE DESCRIPTION: SEQ ID NO: 104:

CGAAAGCCAT GTCGGACTCG TCGCCCAGCG CCCAAGCGCT AACCCGCTGA AAGTTTCTCA    60
```

-continued

```
GCGAAATCTC AGGGACGATC TGGACCCCGC TGAGAGGAAC TGCTTTTGAG TGAG ATG         117
                                                             Met
                                                             1

GTC CCA GAG GCC TGG AGG AGC GGA CTG GTA AGC ACC GGG AGG GTA GTG         165
Val Pro Glu Ala Trp Arg Ser Gly Leu Val Ser Thr Gly Arg Val Val
            5                   10                  15

GGA GTT TTG CTT CTG CTT GGT GCC TTG AAC AAG GCT TCC ACG GTC ATT         213
Gly Val Leu Leu Leu Leu Gly Ala Leu Asn Lys Ala Ser Thr Val Ile
        20                  25                  30

CAC TAT GAG ATC CCG GAG GAA AGA GAG AAG GGT TTC GCT GTG GGC AAC         261
His Tyr Glu Ile Pro Glu Glu Arg Glu Lys Gly Phe Ala Val Gly Asn
        35                  40                  45

GTG GTC GCG AAC CTT GGT TTG GAT CTC GGT AGC CTC TCA GCC CGC AGG         309
Val Val Ala Asn Leu Gly Leu Asp Leu Gly Ser Leu Ser Ala Arg Arg
50              55                  60                  65

TTC CCG GTG GTG TCT GGA GCT AGC CGA AGA TTC TTT GAG GTG AAC CGG         357
Phe Pro Val Val Ser Gly Ala Ser Arg Arg Phe Phe Glu Val Asn Arg
                70                  75                  80

GAG ACC GGA GAG ATG TTT GTG AAC GAC CGT CTG GAT CGA GAG GAG CTG         405
Glu Thr Gly Glu Met Phe Val Asn Asp Arg Leu Asp Arg Glu Glu Leu
                    85                  90                  95

TGT GGG ACA CTG CCC TCT TGC ACT GTA ACT CTG GAG TTG GTA GTG GAG         453
Cys Gly Thr Leu Pro Ser Cys Thr Val Thr Leu Glu Leu Val Val Glu
                100                 105                 110

AAC CCG CTG GAG CTG TTC AGC GTG GAA GTG GTG ATC CAG GAC ATC AAC         501
Asn Pro Leu Glu Leu Phe Ser Val Glu Val Val Ile Gln Asp Ile Asn
115                 120                 125

GAC AAC AAT CCT GCT TTC CCT ACC CAG GAA ATG AAA TTG GAG ATT AGC         549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
                150                 155                 160

CCC GAT CTG GGA AGC AAC TCT TTA CAA ACC TAT GAG CTG AGC CGA AAT         645
Pro Asp Leu Gly Ser Asn Ser Leu Gln Thr Tyr Glu Leu Ser Arg Asn
                165                 170                 175

GAA TAC TTT GCG CTT CGC GTG CAG ACG CGG GAG GAC AGC ACC AAG TAC         693
Glu Tyr Phe Ala Leu Arg Val Gln Thr Arg Glu Asp Ser Thr Lys Tyr
                180                 185                 190

GCG GAG CTG GTG TTG GAG CGC GCC CTG GAC CGA GAA CGG GAG CCT AGT         741
Ala Glu Leu Val Leu Glu Arg Ala Leu Asp Arg Glu Arg Glu Pro Ser
195                 200                 205

CTC CAG TTA GTG CTG ACG GCG TTG GAC GGA GGG ACC CCA GCT CTC TCC         789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG         837
Ala Ser Leu Pro Ile His Ile Lys Val Leu Asp Ala Asn Asp Asn Ala
                230                 235                 240

CCT GTC TTC AAC CAG TCC TTG TAC CGG GCG CGC GTT CCT GGA GGA TGC         885
Pro Val Phe Asn Gln Ser Leu Tyr Arg Ala Arg Val Pro Gly Gly Cys
                245                 250                 255

ACC TCC GGC ACG CGC GTG GTA CAA GTC CTT GCA ACG GAT CTG GAT GAA         933
Thr Ser Gly Thr Arg Val Val Gln Val Leu Ala Thr Asp Leu Asp Glu
                260                 265                 270

GGC CCC AAC GGT GAA ATT ATT TAC TCC TTC GGC AGC CAC AAC CGC GCC         981
Gly Pro Asn Gly Glu Ile Ile Tyr Ser Phe Gly Ser His Asn Arg Ala
            275                 280                 285

GGC GTG CGG CAA CTA TTC GCC TTA GAC CTT GTA ACC GGG ATG CTG ACA        1029
Gly Val Arg Gln Leu Phe Ala Leu Asp Leu Val Thr Gly Met Leu Thr
290                 295                 300                 305
```

```
ATC AAG GGT CGG CTG GAC TTC GAG GAC ACC AAA CTC CAT GAG ATT TAC        1077
Ile Lys Gly Arg Leu Asp Phe Glu Asp Thr Lys Leu His Glu Ile Tyr
                310                 315                 320

ATC CAG GCC AAA GAC AAG GGC GCC AAT CCC GAA GGA GCA CAT TGC AAA        1125
Ile Gln Ala Lys Asp Lys Gly Ala Asn Pro Glu Gly Ala His Cys Lys
            325                 330                 335

GTG TTG GTG GAG GTT GTG GAT GTG AAT GAC AAC GCC CCG GAG ATC ACA        1173
Val Leu Val Glu Val Val Asp Val Asn Asp Asn Ala Pro Glu Ile Thr
        340                 345                 350

GTC ACC TCC GTG TAC AGC CCA GTA CCC GAG GAT GCC TCT GGG ACT GTC        1221
Val Thr Ser Val Tyr Ser Pro Val Pro Glu Asp Ala Ser Gly Thr Val
    355                 360                 365

ATC GCT TTG CTC AGT GTG ACT GAC CTG GAT GCT GGC GAG AAC GGG CTG        1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC        1317
Val Thr Cys Glu Val Pro Pro Gly Leu Pro Phe Ser Leu Thr Ser Ser
                390                 395                 400

CTC AAG AAT TAC TTC ACT TTG AAA ACC AGT GCA GAC CTG GAT CGG GAG        1365
Leu Lys Asn Tyr Phe Thr Leu Lys Thr Ser Ala Asp Leu Asp Arg Glu
            405                 410                 415

ACT GTG CCA GAA TAC AAC CTC AGC ATC ACC GCC CGA GAC GCC GGA ACC        1413
Thr Val Pro Glu Tyr Asn Leu Ser Ile Thr Ala Arg Asp Ala Gly Thr
        420                 425                 430

CCT TCC CTC TCA GCC CTT ACA ATA GTG CGT GTT CAA GTG TCC GAC ATC        1461
Pro Ser Leu Ser Ala Leu Thr Ile Val Arg Val Gln Val Ser Asp Ile
    435                 440                 445

AAT GAC AAC CCT CCA CAA TCT TCT CAA TCT TCC TAC GAC GTT TAC ATT        1509
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG        1557
Glu Glu Asn Asn Leu Pro Gly Ala Pro Ile Leu Asn Leu Ser Val Trp
                470                 475                 480

GAC CCC GAC GCC CCG CAG AAT GCT CGG CTT TCT TTC TTT CTC TTG GAG        1605
Asp Pro Asp Ala Pro Gln Asn Ala Arg Leu Ser Phe Phe Leu Leu Glu
            485                 490                 495

CAA GGA GCT GAA ACC GGG CTA GTG GGT CGC TAT TTC ACA ATA AAT CGT        1653
Gln Gly Ala Glu Thr Gly Leu Val Gly Arg Tyr Phe Thr Ile Asn Arg
        500                 505                 510

GAC AAT GGC ATA GTG TCA TCC TTA GTG CCC CTA GAC TAT GAG GAT CGG        1701
Asp Asn Gly Ile Val Ser Ser Leu Val Pro Leu Asp Tyr Glu Asp Arg
    515                 520                 525

CGG GAA TTT GAA TTA ACA GCT CAT ATC AGC GAT GGG GGC ACC CCG GTC        1749
Arg Glu Phe Glu Leu Thr Ala His Ile Ser Asp Gly Gly Thr Pro Val
530                 535                 540                 545

CTA GCC ACC AAC ATC AGC GTG AAC ATA TTT GTC ACT GAT CGC AAT GAC        1797
Leu Ala Thr Asn Ile Ser Val Asn Ile Phe Val Thr Asp Arg Asn Asp
                550                 555                 560

AAT GCC CCC CAG GTC CTA TAT CCT CGG CCA GGT GGG AGC TCG GTG GAG        1845
Asn Ala Pro Gln Val Leu Tyr Pro Arg Pro Gly Gly Ser Ser Val Glu
            565                 570                 575

ATG CTG CCT CGA GGT ACC TCA GCT GGC CAC CTA GTG TCA CGG GTG GTA        1893
Met Leu Pro Arg Gly Thr Ser Ala Gly His Leu Val Ser Arg Val Val
        580                 585                 590

GGC TGG GAC GCG GAT GCA GGG CAC AAT GCC TGG CTC TCC TAC AGT CTC        1941
Gly Trp Asp Ala Asp Ala Gly His Asn Ala Trp Leu Ser Tyr Ser Leu
    595                 600                 605

TTT GGA TCC CCT AAC CAG AGC CTT TTT GCC ATA GGG CTG CAC ACT GGT        1989
Phe Gly Ser Pro Asn Gln Ser Leu Phe Ala Ile Gly Leu His Thr Gly
```

```
          610             615              620               625
CAA ATC AGT ACT GCC CGT CCA GTC CAA GAC ACA GAT TCA CCC AGG CAG    2037
Gln Ile Ser Thr Ala Arg Pro Val Gln Asp Thr Asp Ser Pro Arg Gln
                    630              635              640

ACT CTC ACT GTC TTG ATC AAA GAC AAT GGG GAG CCT TCG CTC TCC ACC    2085
Thr Leu Thr Val Leu Ile Lys Asp Asn Gly Glu Pro Ser Leu Ser Thr
                645              650              655

ACT GCT ACC CTC ACT GTG TCA GTA ACC GAG GAC TCT CCT GAA GCC CGA    2133
Thr Ala Thr Leu Thr Val Ser Val Thr Glu Asp Ser Pro Glu Ala Arg
                660              665              670

GCC GAG TTC CCC TCT GGC TCT GCC CCC CGG GAG CAG AAA AAA AAT CTC    2181
Ala Glu Phe Pro Ser Gly Ser Ala Pro Arg Glu Gln Lys Lys Asn Leu
            675              680              685

ACC TTT TAT CTA CTT CTT TCT CTA ATC CTG GTT TCT GTG GGC TTC GTG    2229
Thr Phe Tyr Leu Leu Leu Ser Leu Ile Leu Val Ser Val Gly Phe Val
690              695              700              705

GTC ACA GTG TTC GGA GTA ATC ATA TTC AAA GTT TAC AAG TGG AAG CAG    2277
Val Thr Val Phe Gly Val Ile Ile Phe Lys Val Tyr Lys Trp Lys Gln
                710              715              720

TCT AGA GAC CTA TAC CGA GCC CCG GTG AGC TCA CTG TAC CGA ACA CCA    2325
Ser Arg Asp Leu Tyr Arg Ala Pro Val Ser Ser Leu Tyr Arg Thr Pro
                725              730              735

GGG CCC TCC TTG CAC GCG GAC GCC GTG CGG GGA GGC CTG ATG TCG CCG    2373
Gly Pro Ser Leu His Ala Asp Ala Val Arg Gly Gly Leu Met Ser Pro
            740              745              750

CAC CTT TAC CAT CAG GTG TAT CTC ACC ACG GAC TCC CGC CGC AGC GAC    2421
His Leu Tyr His Gln Val Tyr Leu Thr Thr Asp Ser Arg Arg Ser Asp
            755              760              765

CCG CTG CTG AAG AAA CCT GGT GCA GCC AGT CCA CTG GCC AGC CGC CAG    2469
Pro Leu Leu Lys Lys Pro Gly Ala Ala Ser Pro Leu Ala Ser Arg Gln
770              775              780              785

AAC ACG CTG CGG AGC TGT GAT CCG GTG TTC TAT AGG CAG GTG TTG GGT    2517
Asn Thr Leu Arg Ser Cys Asp Pro Val Phe Tyr Arg Gln Val Leu Gly
                790              795              800

GCA GAG AGC GCC CCT CCC GGA CAG GTA AGG TTT AGC AAG TCA TGC TTG    2565
Ala Glu Ser Ala Pro Pro Gly Gln Val Arg Phe Ser Lys Ser Cys Leu
            805              810              815

ACC CTG TTA GTG CCT TTT TAT TCC TAC ATC ATA TTG AGA AGG CTG GAG    2613
Thr Leu Leu Val Pro Phe Tyr Ser Tyr Ile Ile Leu Arg Arg Leu Glu
            820              825              830

CTG TTT TTT TAGTGATGAA GATGTTTTCC TGGTGATGCA TTCACACTTT           2662
Leu Phe Phe
        835

CAACTGGCTC TTCCTAGATC AAAGTTAGTG CCTTTGTGAG ATGGTGGCCT GCCAGAGTGT  2722

GGTTTGTGGT CCCATTTCAG GGGGAAGATA CTTGACTCAT CTGTGGACCT AATTCACATC  2782

CTCAGCG                                                            2789

(2) INFORMATION FOR SEQ ID NO: 105:

(i) SEQUENCE CHARACTERISTICS:
        (A) LENGTH: 836 amino acids
        (B) TYPE: amino acid
        (D) TOPOLOGY: linear (ii) MOLECULE TYPE: protein (xi) SEQUENCE DESCRIPTION: SEQ ID NO: 105:

Met Val Pro Glu Ala Trp Arg Ser Gly Leu Val Ser Thr Gly Arg Val
 1               5                  10                  15
```

-continued

```
Val Gly Val Leu Leu Leu Gly Ala Leu Asn Lys Ala Ser Thr Val
             20                  25                  30

Ile His Tyr Glu Ile Pro Glu Arg Glu Lys Gly Phe Ala Val Gly
             35                  40                  45

Asn Val Val Ala Asn Leu Gly Leu Asp Leu Gly Ser Leu Ser Ala Arg
 50                  55                  60

Arg Phe Pro Val Val Ser Gly Ala Ser Arg Arg Phe Glu Val Asn
 65                  70                  75                  80

Arg Glu Thr Gly Glu Met Phe Val Asn Asp Arg Leu Asp Arg Glu Glu
                 85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
                115                 120                 125

Asn Asp Asn Asn Pro Ala Phe Pro Thr Gln Glu Met Lys Leu Glu Ile
130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
                180                 185                 190

Tyr Ala Glu Leu Val Leu Glu Arg Ala Leu Asp Arg Glu Arg Glu Pro
                195                 200                 205

Ser Leu Gln Leu Val Leu Thr Ala Leu Asp Gly Gly Thr Pro Ala Leu
                210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
                260                 265                 270

Glu Gly Pro Asn Gly Glu Ile Ile Tyr Ser Phe Gly Ser His Asn Arg
                275                 280                 285

Ala Gly Val Arg Gln Leu Phe Ala Leu Asp Leu Val Thr Gly Met Leu
                290                 295                 300

Thr Ile Lys Gly Arg Leu Asp Phe Glu Asp Thr Lys Leu His Glu Ile
305                 310                 315                 320

Tyr Ile Gln Ala Lys Asp Lys Gly Ala Asn Pro Glu Gly Ala His Cys
                325                 330                 335

Lys Val Leu Val Glu Val Val Asp Val Asn Asp Asn Ala Pro Glu Ile
                340                 345                 350

Thr Val Thr Ser Val Tyr Ser Pro Val Pro Glu Asp Ala Ser Gly Thr
                355                 360                 365

Val Ile Ala Leu Leu Ser Val Thr Asp Leu Asp Ala Gly Glu Asn Gly
                370                 375                 380

Leu Val Thr Cys Glu Val Pro Pro Gly Leu Pro Phe Ser Leu Thr Ser
385                 390                 395                 400

Ser Leu Lys Asn Tyr Phe Thr Leu Lys Thr Ser Ala Asp Leu Asp Arg
                405                 410                 415

Glu Thr Val Pro Glu Tyr Asn Leu Ser Ile Thr Ala Arg Asp Ala Gly
                420                 425                 430

Thr Pro Ser Leu Ser Ala Leu Thr Ile Val Arg Val Gln Val Ser Asp
```

```
                435                 440                 445
Ile Asn Asp Asn Pro Pro Gln Ser Ser Gln Ser Ser Tyr Asp Val Tyr
            450                 455                 460

Ile Glu Glu Asn Asn Leu Pro Gly Ala Pro Ile Leu Asn Leu Ser Val
465                 470                 475                 480

Trp Asp Pro Asp Ala Pro Gln Asn Ala Arg Leu Ser Phe Phe Leu Leu
                485                 490                 495

Glu Gln Gly Ala Glu Thr Gly Leu Val Gly Arg Tyr Phe Thr Ile Asn
            500                 505                 510

Arg Asp Asn Gly Ile Val Ser Leu Val Pro Leu Asp Tyr Glu Asp
            515                 520                 525

Arg Arg Glu Phe Glu Leu Thr Ala His Ile Ser Asp Gly Gly Thr Pro
530                 535                 540

Val Leu Ala Thr Asn Ile Ser Val Asn Ile Phe Val Thr Asp Arg Asn
545                 550                 555                 560

Asp Asn Ala Pro Gln Val Leu Tyr Pro Arg Pro Gly Gly Ser Ser Val
                565                 570                 575

Glu Met Leu Pro Arg Gly Thr Ser Ala Gly His Leu Val Ser Arg Val
            580                 585                 590

Val Gly Trp Asp Ala Asp Ala Gly His Asn Ala Trp Leu Ser Tyr Ser
            595                 600                 605

Leu Phe Gly Ser Pro Asn Gln Ser Leu Phe Ala Ile Gly Leu His Thr
    610                 615                 620

Gly Gln Ile Ser Thr Ala Arg Pro Val Gln Asp Thr Asp Ser Pro Arg
625                 630                 635                 640

Gln Thr Leu Thr Val Leu Ile Lys Asp Asn Gly Glu Pro Ser Leu Ser
                645                 650                 655

Thr Thr Ala Thr Leu Thr Val Ser Val Thr Glu Asp Ser Pro Glu Ala
                660                 665                 670

Arg Ala Glu Phe Pro Ser Gly Ser Ala Pro Arg Glu Gln Lys Lys Asn
            675                 680                 685

Leu Thr Phe Tyr Leu Leu Leu Ser Leu Ile Leu Val Ser Val Gly Phe
            690                 695                 700

Val Val Thr Val Phe Gly Val Ile Ile Phe Lys Val Tyr Lys Trp Lys
705                 710                 715                 720

Gln Ser Arg Asp Leu Tyr Arg Ala Pro Val Ser Ser Leu Tyr Arg Thr
                725                 730                 735

Pro Gly Pro Ser Leu His Ala Asp Ala Val Arg Gly Leu Met Ser
                740                 745                 750

Pro His Leu Tyr His Gln Val Tyr Leu Thr Thr Asp Ser Arg Arg Ser
            755                 760                 765

Asp Pro Leu Leu Lys Lys Pro Gly Ala Ala Ser Pro Leu Ala Ser Arg
770                 775                 780

Gln Asn Thr Leu Arg Ser Cys Asp Pro Val Phe Tyr Arg Gln Val Leu
785                 790                 795                 800

Gly Ala Glu Ser Ala Pro Pro Gly Gln Val Arg Phe Ser Lys Ser Cys
                805                 810                 815

Leu Thr Leu Leu Val Pro Phe Tyr Ser Tyr Ile Ile Leu Arg Arg Leu
                820                 825                 830

Glu Leu Phe Phe
            835

(2) INFORMATION FOR SEQ ID NO: 106:
```

(i) SEQUENCE CHARACTERISTICS:
  (A) LENGTH: 2751 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 115..2160

(xi) SEQUENCE DESCRIPTION: SEQ ID NO: 106:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG         117
                                                             Met
                                                              1

GTC CCA GAG GCC TGG AGG AGC GGA CTG GTA AGC ACC GGG AGG GTA GTG         165
Val Pro Glu Ala Trp Arg Ser Gly Leu Val Ser Thr Gly Arg Val Val
         5                  10                  15

GGA GTT TTG CTT CTG CTT GGT GCC TTG AAC AAG GCT TCC ACG GTC ATT         213
Gly Val Leu Leu Leu Leu Gly Ala Leu Asn Lys Ala Ser Thr Val Ile
         20                  25                  30

CAC TAT GAG ATC CCG GAG GAA AGA GAG AAG GGT TTC GCT GTG GGC AAC         261
His Tyr Glu Ile Pro Glu Glu Arg Glu Lys Gly Phe Ala Val Gly Asn
 35                  40                  45

GTG GTC GCG AAC CTT GGT TTG GAT CTC GGT AGC CTC TCA GCC CGC AGG         309
Val Val Ala Asn Leu Gly Leu Asp Leu Gly Ser Leu Ser Ala Arg Arg
 50                  55                  60                  65

TTC CCG GTG GTG TCT GGA GCT AGC CGA AGA TTC TTT GAG GTG AAC CGG         357
Phe Pro Val Val Ser Gly Ala Ser Arg Arg Phe Phe Glu Val Asn Arg
             70                  75                  80

GAG ACC GGA GAG ATG TTT GTG AAC GAC CGT CTG GAT CGA GAG GAG CTG         405
Glu Thr Gly Glu Met Phe Val Asn Asp Arg Leu Asp Arg Glu Glu Leu
                 85                  90                  95

TGT GGG ACA CTG CCC TCT TGC ACT GTA ACT CTG GAG TTG GTA GTG GAG         453
Cys Gly Thr Leu Pro Ser Cys Thr Val Thr Leu Glu Leu Val Val Glu
             100                 105                 110

AAC CCG CTG GAG CTG TTC AGC GTG GAA GTG GTG ATC CAG GAC ATC AAC         501
Asn Pro Leu Glu Leu Phe Ser Val Glu Val Val Ile Gln Asp Ile Asn
115                 120                 125

GAC AAC AAT CCT GCT TTC CCT ACC CAG GAA ATG AAA TTG GAG ATT AGC         549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
                 150                 155                 160

CCC GAT CTG GGA AGC AAC TCT TTA CAA ACC TAT GAG CTG AGC CGA AAT         645
Pro Asp Leu Gly Ser Asn Ser Leu Gln Thr Tyr Glu Leu Ser Arg Asn
             165                 170                 175

GAA TAC TTT GCG CTT CGC GTG CAG ACG CGG GAG GAC AGC ACC AAG TAC         693
Glu Tyr Phe Ala Leu Arg Val Gln Thr Arg Glu Asp Ser Thr Lys Tyr
             180                 185                 190

GCG GAG CTG GTG TTG GAG CGC GCC CTG GAC CGA GAA CGG GAG CCT AGT         741
Ala Glu Leu Val Leu Glu Arg Ala Leu Asp Arg Glu Arg Glu Pro Ser
195                 200                 205

CTC CAG TTA GTG CTG ACG GCG TTG GAC GGA GGG ACC CCA GCT CTC TCC         789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG         837
Ala Ser Leu Pro Ile His Ile Lys Val Leu Asp Ala Asn Asp Asn Ala
```

```
                      230                 235                 240
CCT GTC TTC AAC CAG TCC TTG TAC CGG GCG CGC GTT CCT GGA GGA TGC     885
Pro Val Phe Asn Gln Ser Leu Tyr Arg Ala Arg Val Pro Gly Gly Cys
            245                 250                 255

ACC TCC GGC ACG CGC GTG GTA CAA GTC CTT GCA ACG GAT CTG GAT GAA     933
Thr Ser Gly Thr Arg Val Val Gln Val Leu Ala Thr Asp Leu Asp Glu
            260                 265                 270

GGC CCC AAC GGT GAA ATT ATT TAC TCC TTC GGC AGC CAC AAC CGC GCC     981
Gly Pro Asn Gly Glu Ile Ile Tyr Ser Phe Gly Ser His Asn Arg Ala
            275                 280                 285

GGC GTG CGG CAA CTA TTC GCC TTA GAC CTT GTA ACC GGG ATG CTG ACA    1029
Gly Val Arg Gln Leu Phe Ala Leu Asp Leu Val Thr Gly Met Leu Thr
290                 295                 300                 305

ATC AAG GGT CGG CTG GAC TTC GAG GAC ACC AAA CTC CAT GAG ATT TAC    1077
Ile Lys Gly Arg Leu Asp Phe Glu Asp Thr Lys Leu His Glu Ile Tyr
            310                 315                 320

ATC CAG GCC AAA GAC AAG GGC GCC AAT CCC GAA GGA GCA CAT TGC AAA    1125
Ile Gln Ala Lys Asp Lys Gly Ala Asn Pro Glu Gly Ala His Cys Lys
            325                 330                 335

GTG TTG GTG GAG GTT GTG GAT GTG AAT GAC AAC GCC CCG GAG ATC ACA    1173
Val Leu Val Glu Val Val Asp Val Asn Asp Asn Ala Pro Glu Ile Thr
            340                 345                 350

GTC ACC TCC GTG TAC AGC CCA GTA CCC GAG GAT GCC TCT GGG ACT GTC    1221
Val Thr Ser Val Tyr Ser Pro Val Pro Glu Asp Ala Ser Gly Thr Val
            355                 360                 365

ATC GCT TTG CTC AGT GTG ACT GAC CTG GAT GCT GGC GAG AAC GGG CTG    1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC    1317
Val Thr Cys Glu Val Pro Pro Gly Leu Pro Phe Ser Leu Thr Ser Ser
            390                 395                 400

CTC AAG AAT TAC TTC ACT TTG AAA ACC AGT GCA GAC CTG GAT CGG GAG    1365
Leu Lys Asn Tyr Phe Thr Leu Lys Thr Ser Ala Asp Leu Asp Arg Glu
            405                 410                 415

ACT GTG CCA GAA TAC AAC CTC AGC ATC ACC GCC CGA GAC GCC GGA ACC    1413
Thr Val Pro Glu Tyr Asn Leu Ser Ile Thr Ala Arg Asp Ala Gly Thr
            420                 425                 430

CCT TCC CTC TCA GCC CTT ACA ATA GTG CGT GTT CAA GTG TCC GAC ATC    1461
Pro Ser Leu Ser Ala Leu Thr Ile Val Arg Val Gln Val Ser Asp Ile
            435                 440                 445

AAT GAC AAC CCT CCA CAA TCT TCT CAA TCT TCC TAC GAC GTT TAC ATT    1509
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG    1557
Glu Glu Asn Asn Leu Pro Gly Ala Pro Ile Leu Asn Leu Ser Val Trp
            470                 475                 480

GAC CCC GAC GCC CCG CAG AAT GCT CGG CTT TCT TTC TTT CTC TTG GAG    1605
Asp Pro Asp Ala Pro Gln Asn Ala Arg Leu Ser Phe Phe Leu Leu Glu
            485                 490                 495

CAA GGA GCT GAA ACC GGG CTA GTG GGT CGC TAT TTC ACA ATA AAT CGT    1653
Gln Gly Ala Glu Thr Gly Leu Val Gly Arg Tyr Phe Thr Ile Asn Arg
            500                 505                 510

GAC AAT GGC ATA GTG TCA TCC TTA GTG CCC CTA GAC TAT GAG GAT CGG    1701
Asp Asn Gly Ile Val Ser Ser Leu Val Pro Leu Asp Tyr Glu Asp Arg
            515                 520                 525

CGG GAA TTT GAA TTA ACA GCT CAT ATC AGC GAT GGG GGC ACC CCG GTC    1749
Arg Glu Phe Glu Leu Thr Ala His Ile Ser Asp Gly Gly Thr Pro Val
530                 535                 540                 545

CTA GCC ACC AAC ATC AGC GTG AAC ATA TTT GTC ACT GAT CGC AAT GAC    1797
Leu Ala Thr Asn Ile Ser Val Asn Ile Phe Val Thr Asp Arg Asn Asp
```

```
Leu Ala Thr Asn Ile Ser Val Asn Ile Phe Val Thr Asp Arg Asn Asp
            550                 555                 560

AAT GCC CCC CAG GTC CTA TAT CCT CGG CCA GGT GGG AGC TCG GTG GAG      1845
Asn Ala Pro Gln Val Leu Tyr Pro Arg Pro Gly Gly Ser Ser Val Glu
            565                 570                 575

ATG CTG CCT CGA GGT ACC TCA GCT GGC CAC CTA GTG TCA CGG GTG GTA      1893
Met Leu Pro Arg Gly Thr Ser Ala Gly His Leu Val Ser Arg Val Val
            580                 585                 590

GGC TGG GAC GCG GAT GCA GGG CAC AAT GCC TGG CTC TCC TAC AGT CTC      1941
Gly Trp Asp Ala Asp Ala Gly His Asn Ala Trp Leu Ser Tyr Ser Leu
        595                 600                 605

TTT GGA TCC CCT AAC CAG AGC CTT TTT GCC ATA GGG CTG CAC ACT GGT      1989
Phe Gly Ser Pro Asn Gln Ser Leu Phe Ala Ile Gly Leu His Thr Gly
610                 615                 620                 625

CAA ATC AGT ACT GCC CGT CCA GTC CAA GAC ACA GAT TCA CCC AGG CAG      2037
Gln Ile Ser Thr Ala Arg Pro Val Gln Asp Thr Asp Ser Pro Arg Gln
            630                 635                 640

ACT CTC ACT GTC TTG ATC AAA GAC AAT GGG GAG CCT TCG CTC TCC ACC      2085
Thr Leu Thr Val Leu Ile Lys Asp Asn Gly Glu Pro Ser Leu Ser Thr
            645                 650                 655

ACT GCT ACC CTC ACT GTG TCA GTA ACC GAG GAC TCT CCT GAA GCC CGA      2133
Thr Ala Thr Leu Thr Val Ser Val Thr Glu Asp Ser Pro Glu Ala Arg
            660                 665                 670

GCC GAG TTC CCC TCT GGC TCT GCC AGT TAAACCTTCT TTAATTATGG            2180
Ala Glu Phe Pro Ser Gly Ser Ala Ser
            675                 680

ATTAGCCATT AACATTTTTG AAACGTGGAC CATTTAACCT CGGCCTACCC CCTCCAACTG    2240

TCCTGGTGAT GAGTTCATTA GCTAAGTTAA ATTAATTGAA CTTTGATCTA AACCAAAACA    2300

AATCAGGAAA ATAAAGCTGT AAAGGAACTT ATCAAGCATT CCAAAACCAA CTAGAAATTA    2360

CTTGAAGTTT CGAGTGAGCA TTGCCTGTGC CAGTATTCTT CATTATAGGA TTATAAACTC    2420

GTTTTTTTCC CAAAGCGCAT GTCTACGCCA GGCAGAGGAG TAATTATTCA GCCAATTTCA    2480

TGGATGTAAC GATGGATATA AATAATTGAT AGCACCTAGA GGCTTCCAGT TTGGGTGGAA    2540

GGCTAAAAGT AGAGGGGAAC TCACTCACTT GAGAAATGAT ATTTAAGTGA ATAAATAGTT    2600

CTCTTCTATG AAACTATTAC TATTTAGTTC TCTGGAAAAC TTAAGTGTAT TAATGATTAG    2660

AACATCAAAT CCTAAGTAAA GAAATGACAT TTTAAATATA AAAAGCCAAA CTTTAAATAA    2720

ATCATAGAGA CCTCAGACAT AATATAGGAA A                                   2751

(2) INFORMATION FOR SEQ ID NO: 107:

(i) SEQUENCE CHARACTERISTICS:
        (A) LENGTH: 682 amino acids
        (B) TYPE: amino acid
        (D) TOPOLOGY: linear (ii) MOLECULE TYPE: protein (xi) SEQUENCE DESCRIPTION: SEQ ID NO: 107:

Met Val Pro Glu Ala Trp Arg Ser Gly Leu Val Ser Thr Gly Arg Val
 1               5                  10                  15

Val Gly Val Leu Leu Leu Leu Gly Ala Leu Asn Lys Ala Ser Thr Val
            20                  25                  30

Ile His Tyr Glu Ile Pro Glu Glu Arg Glu Lys Gly Phe Ala Val Gly
        35                  40                  45

Asn Val Val Ala Asn Leu Gly Leu Asp Leu Gly Ser Leu Ser Ala Arg
    50                  55                  60
```

```
Arg Phe Pro Val Val Ser Gly Ala Ser Arg Arg Phe Glu Val Asn
 65                  70                  75                  80

Arg Glu Thr Gly Glu Met Phe Val Asn Asp Arg Leu Asp Arg Glu Glu
                 85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
                180                 185                 190

Tyr Ala Glu Leu Val Leu Glu Arg Ala Leu Asp Arg Glu Arg Glu Pro
            195                 200                 205

Ser Leu Gln Leu Val Leu Thr Ala Leu Asp Gly Gly Thr Pro Ala Leu
    210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
                260                 265                 270

Glu Gly Pro Asn Gly Glu Ile Ile Tyr Ser Phe Gly Ser His Asn Arg
            275                 280                 285

Ala Gly Val Arg Gln Leu Phe Ala Leu Asp Leu Val Thr Gly Met Leu
    290                 295                 300

Thr Ile Lys Gly Arg Leu Asp Phe Glu Asp Thr Lys Leu His Glu Ile
305                 310                 315                 320

Tyr Ile Gln Ala Lys Asp Lys Gly Ala Asn Pro Glu Gly Ala His Cys
                325                 330                 335

Lys Val Leu Val Glu Val Val Asp Val Asn Asp Asn Ala Pro Glu Ile
                340                 345                 350

Thr Val Thr Ser Val Tyr Ser Pro Val Pro Glu Asp Ala Ser Gly Thr
            355                 360                 365

Val Ile Ala Leu Leu Ser Val Thr Asp Leu Asp Ala Gly Glu Asn Gly
    370                 375                 380

Leu Val Thr Cys Glu Val Pro Pro Gly Leu Pro Phe Ser Leu Thr Ser
385                 390                 395                 400

Ser Leu Lys Asn Tyr Phe Thr Leu Lys Thr Ser Ala Asp Leu Asp Arg
                405                 410                 415

Glu Thr Val Pro Glu Tyr Asn Leu Ser Ile Thr Ala Arg Asp Ala Gly
            420                 425                 430

Thr Pro Ser Leu Ser Ala Leu Thr Ile Val Arg Val Gln Val Ser Asp
    435                 440                 445

Ile Asn Asp Asn Pro Pro Gln Ser Ser Gln Ser Ser Tyr Asp Val Tyr
450                 455                 460

Ile Glu Glu Asn Asn Leu Pro Gly Ala Pro Ile Leu Asn Leu Ser Val
465                 470                 475                 480

Trp Asp Pro Asp Ala Pro Gln Asn Ala Arg Leu Ser Phe Phe Leu Leu
```

```
                            485                 490                 495
Glu Gln Gly Ala Glu Thr Gly Leu Val Gly Arg Tyr Phe Thr Ile Asn
                500                 505                 510
Arg Asp Asn Gly Ile Val Ser Ser Leu Val Pro Leu Asp Tyr Glu Asp
                515                 520                 525
Arg Arg Glu Phe Glu Leu Thr Ala His Ile Ser Asp Gly Gly Thr Pro
                530                 535                 540
Val Leu Ala Thr Asn Ile Ser Val Asn Ile Phe Val Thr Asp Arg Asn
545                 550                 555                 560
Asp Asn Ala Pro Gln Val Leu Tyr Pro Arg Pro Gly Gly Ser Ser Val
                565                 570                 575
Glu Met Leu Pro Arg Gly Thr Ser Ala Gly His Leu Val Ser Arg Val
                580                 585                 590
Val Gly Trp Asp Ala Asp Ala Gly His Asn Ala Trp Leu Ser Tyr Ser
595                 600                 605
Leu Phe Gly Ser Pro Asn Gln Ser Leu Phe Ala Ile Gly Leu His Thr
                610                 615                 620
Gly Gln Ile Ser Thr Ala Arg Pro Val Gln Asp Thr Asp Ser Pro Arg
625                 630                 635                 640
Gln Thr Leu Thr Val Leu Ile Lys Asp Asn Gly Glu Pro Ser Leu Ser
                645                 650                 655
Thr Thr Ala Thr Leu Thr Val Ser Val Thr Glu Asp Ser Pro Glu Ala
                660                 665                 670
Arg Ala Glu Phe Pro Ser Gly Ser Ala Ser
                675                 680
```

(2) INFORMATION FOR SEQ ID NO: 108:

(i) SEQUENCE CHARACTERISTICS:
        (A) LENGTH: 2831 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 108:

```
GAATTCGGCA CGAGGCTGAA CTGAGGGTGA CGGACATAAA CGACTATTCT CCAGTGTTCA      60
GTGAAAGAGA AATGATACTG AGGATACCAG AAAACAGTGC TCGGGGAAAT ACATTCCCTT     120
TAAACAATGC TCTGGACTCA GACGTAGATA TCAACAATAT CCAGACCTAT AGGCTCAGCT     180
CAAACTCTCA TTTCCTGGTT GTAACCCGCA ACCGCAGTGA TGGCAGGAAG TACCCAGAGC     240
TGGTGCTGGA GAAAGAACTG GATCGAGAGG AGGAACCTGA GCTGAGGTTA ACGCTGACAG     300
CTTTGGATGG TGGCTCTCCT CCCCGGTCTG GGACGACACA GGTCCTCATT GAAGTAGTGG     360
ACACCAACGA TAATGCACCC GAGTTTCAGC AGCCAACATA CCAAGTGCAA ACTCCCGAGA     420
ACAGTCCCAC CGGCTCTCTG GTACTCACAG TCTCAGCCAA TGACTTAGAC AGTGGAGACT     480
ATGGGAAAGT CTTGTACGCA CTTTCGCAAC CCTCAGAAGA TATTAGCAAA ACATTCGAGG     540
TAAACCCTGT AACCGGGGAA ATTCGCCTAC GAAAGAGGT GAATTTTGAA ACTATTCCTT      600
CGTATGAAGT GGTTATCAAG GGGACGGACG GGGAGGTCT CTCAGGAAAA TGCACTCTGT      660
TACTGCAGGT GGTGGACGTG AATGACAATG CCCCAGAAGT GATGCTATCT GCGCTAACCA     720
ACCCAGTCCC AGAAAATTCC CCCGATGAGG TAGTGGCTGT TTTCAGTGTT AGAGATCCTG     780
ACTCTGGGAA CAACGGAAAA GTGATTGCAT CCATCGAGGA AGACCTGCCC TTTCTTCTAA     840
```

```
AATCTTCAGG AAAGAACTTT TACACTTTAG TAACCAAGGG AGCACTTGAC AGGGAAGAAA    900
GAGAGCAATT GAACATCACC ATCACAGTCA CTGACCTGGG CATACCCAGG CTCACCACCC    960
AACACACCAT AACAGTGCAG GTGGCAGACA TCAACGACAA TGCCCCCTCC TTCACCCAAA    1020
CCTCCTACAC CATGTTTGTC CGCGAGAACA ACAGCCCCGC CCTGCACATA GGCACCATCA    1080
GCGCCACAGA CTCAGACTCA GGATCCAATG CCCACATCAC CTACTCGCTG CTACCGCCCC    1140
AAGACCCACA GCTGGCCCTC GACTCGCTCA TCTCCATCAA TGTAGACAAC GGGCAGCTGT    1200
TCGCGCTCAG GGCGCTAGAC TATGAGGCTC TGCAGGGCTT CGAGTTCCAT GTGGGCGCCA    1260
CAGACCAAGG CTCGCCCGCG CTCAGCAGCC AGGCTCTGGT GCACGTGGTG GTGTTGGACG    1320
ACAATGACAA TGCGCCCTTC GTGCTCTACC CGCTGCAAAA CGCCTCTGCA CCCTTCACTG    1380
AGCTGCTGCC CAGGGCGGCA GAGCCTGGAT ACCTGGTTAC CAAGGTGGTA GCTGTGGACC    1440
GCGACTCTGG CCAGAATGCC TGGCTGTCAT TCCAGCTGCT CAAGGCCACG GAGCCCGGGC    1500
TGTTCAACGT ATGGGCGCAC AATGGCGAGG TACGCACCTC CAGGCTGCTG AGCGAGCGCG    1560
ACGCACCCAA GCACAAGCTG CTGCTGTTGG TCAAGGACAA TGGAGATCCT CCACGCTCTG    1620
CCAGTGTTAC TCTGCACGTG CTAGTGGTGG ATGCCTTCTC TCAGCCCTAC CTGCCTCTGC    1680
CAGAGGTGGC GCACGACCCT GCACAAGAAG AAGATGCGCT AACACTCTAC CTGGTCATAG    1740
CTTTGGCATC TGTGTCTTCT CTCTTCCTCT TGTCTGTGCT GCTGTTCGTG GGGGTGAGGC    1800
TCTGCAGGAG GGCCAGGGCA GCCTCTCTGA GTGCCTATTC TGTGCCTGAA GGCCACTTTC    1860
CTGGCCAGCT GGTGGATGTC AGAGGTATGG GGACCCTGTC CCAGAGCTAC CAGTATGATG    1920
TATGTCTGAT GGGGGATTCT TCTGGGACCA GCGAATTTAA CTTCTTAAAG CCAGTTCTGC    1980
CTAGCTCTCT GCACCAGTGC TCTGGGAAAG AAATAGAGGA AAATTCCACA CTCCAGAATA    2040
GTTTTGGGTT TCATCATTAA TAGAAAACTA CTTTACAGAT ATTTAATTCC AAATATCATC    2100
TTGTTGATTA ACTAAAGTCT GTTCACATGT AGCTAGCTAG CAACGATTTT AATGTTCACT    2160
TTACCCATCT TTTTTCAGGG TCATGTCTAA AGCTACAAGT TTGNCTTTAC TTATACTTGT    2220
CGCACAGAAT NNNNNNNNNN TGGTGTATAA GTCACAGTCA TGGGATACTG GCACAAGATG    2280
GCAGCTTGAT TGCTCAGTTA TGGCTGCAAA GGGGNGCTTG AGTTTAGGGA ATGTGTTAGA    2340
GCTGGAATAA GTTTTCTGAG AAATGTGTAA GACAAATTTC TTTTGCACAT TCCCTGTGTT    2400
CCTGTACCCC TGTTTCCAGA ACTACGAAAT GTGTCATCAG AAGGCATGCT CACATTTTCC    2460
CCTTTGTTTG CGTGACCCGG GTGCCAGAAA TTAAATAAAA TTAGCATGGA GTTCAATGCA    2520
GCATTAAAAC AAAGTTACTT CTACAAACCT TTTATTCGAC GGTTAAAATT GTAACTTCCC    2580
CACCCATGAG GCTGGCTGTA AGAACCAGTA TGAATGGGTG TCTATCGCAA CCTTATTTTC    2640
AAAAATCAAA CAAAAGGAGA AATGAGAGAC CAAACAACAC GCTACAGGAA AGATTTCATA    2700
AGGATGTATG TATGGACACA AAAACTGGGA TACAGACATT TTAAATCTGT TGGTACCACA    2760
TGGTGGCGCT GCAGGCTAAA GAAATGCAAG GGAAATTAAA AAGAGGCTGA GCTAGAAGTC    2820
AAAAAAAAA A                                                        2831
```

(2) INFORMATION FOR SEQ ID NO: 109:

(i) SEQUENCE CHARACTERISTICS:
        (A) LENGTH: 3353 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 763..3123

(xi) SEQUENCE DESCRIPTION: SEQ ID NO: 109:

```
GTATTTTTCC ACAGTTTAAA ATTTTCATAA AATCATAACT CTCTGACTTT ATGTAGAAAG      60

GATACCACAC TGGAATTAAC GTGTAGCTTT TTCTTGATGT AATCCAACCA ATGGGAGCAC     120

AATTCTGGTA CATAGGCTGT CTAGAATTTG AAAGAAATTA AGAATTCAT TTTGTTTTGC      180

TGATAAATTT TTAAGAAATC ACGTGGCTTT ATGTTATTAT TATTACAAGA TGACTGATCA     240

CTATTATGTC TTCTTTCACT TCTCAATTTC CCTCAGAACA CTACACCCAG ACTACAGGCT     300

CTGGAGGGTG GGACCATGT CTGGGTTGTT TACTGATGTA TTTCATAATT TGGCACATAG      360

AGACCAATAA TACTCCTTTA AATGAAGAAA TTAATAATTA CCATTGCGTG ATATTGTGAT     420

TACATCATTT CCTCCCAATT TCCAAACTCC TAATAGAATA GAGAATAGAT CAATTGTAGC     480

AATTCGTTTC GAAGCAAAGA CAACGCATGG TGGCGCTGCA GGCTAAGGCT TCAAAAAAG      540

GAAAAGGAAA AAGCCCATGA AATGCTACTA GCTACTTCAG ACCTCTTTCA GCCTAAGAGG    600

AAAGCCTGTT AGCAGAGCAC GGACCAGTGT CTCCGGAGAA TGCTATTCTC CTACATTTCC   660

GAACAGGTTA TCAACGCACA GATCGATCAC TGCCTCTGTC CCATCGCTCC CTGAAGTAGC   720

TCTGACTCCG GTTCCTTGAA AGGGGCGTGT ACAGAAGTAA AG ATG GAG CCT GCA       774
                                                  Met Glu Pro Ala
                                                    1
```

```
GGG GAG CGC TTT CCC GAA CAA AGG CAA GTC CTG ATT CTC CTT CTT TTA      822
Gly Glu Arg Phe Pro Glu Gln Arg Gln Val Leu Ile Leu Leu Leu Leu
 5              10                  15                  20

CTG GAA GTG ACT CTG GCA GGC TGG GAA CCC CGT CGC TAT TCT GTG ATG      870
Leu Glu Val Thr Leu Ala Gly Trp Glu Pro Arg Arg Tyr Ser Val Met
            25                  30                  35

GAG GAA ACA GAG AGA GGT TCT TTT GTA GCC AAC CTG GCC AAT GAC CTA      918
Glu Glu Thr Glu Arg Gly Ser Phe Val Ala Asn Leu Ala Asn Asp Leu
                40                  45                  50

GGG CTG GGA GTG GGG GAG CTA GCC GAG CGG GGA GCC CGG GTA GTT TCT      966
Gly Leu Gly Val Gly Glu Leu Ala Glu Arg Gly Ala Arg Val Val Ser
        55                  60                  65

GAG GAT AAC GAA CAA GGC TTG CAG CTT GAT CTG CAG ACC GGG CAG TTG     1014
Glu Asp Asn Glu Gln Gly Leu Gln Leu Asp Leu Gln Thr Gly Gln Leu
    70                  75                  80

ATA TTA AAT GAG AAG CTG GAC CGG GAG AAG CTG TGT GGC CCT ACT GAG    1062
Ile Leu Asn Glu Lys Leu Asp Arg Glu Lys Leu Cys Gly Pro Thr Glu
85                  90                  95                 100

CCC TGT ATA ATG CAT TTC CAA GTG TTA CTG AAA AAA CCT TTG GAA GTA    1110
Pro Cys Ile Met His Phe Gln Val Leu Leu Lys Lys Pro Leu Glu Val
                105                 110                 115

TTT CGA GCT GAA CTA CTA GTG ACA GAC ATA AAC GAT CAT TCT CCT GAG    1158
Phe Arg Ala Glu Leu Leu Val Thr Asp Ile Asn Asp His Ser Pro Glu
            120                 125                 130

TTT CCT GAA AGA GAA ATG ACC CTG AAA ATC CCA GAA ACT AGC TCC CTT    1206
Phe Pro Glu Arg Glu Met Thr Leu Lys Ile Pro Glu Thr Ser Ser Leu
        135                 140                 145

GGG ACT GTG TTT CCT CTG AAA AAA GCT CGG GAC TTG GAC GTG GGC AGC    1254
Gly Thr Val Phe Pro Leu Lys Lys Ala Arg Asp Leu Asp Val Gly Ser
    150                 155                 160

AAT AAT GTT CAA AAC TAC AAT ATT TCT CCC AAT TCT CAT TTC CAT GTT    1302
Asn Asn Val Gln Asn Tyr Asn Ile Ser Pro Asn Ser His Phe His Val
165                 170                 175                 180

TCC ACT CGC ACC CGA GGG GAT GGC AGG AAA TAC CCA GAG CTG GTG CTG    1350
```

-continued

```
Ser Thr Arg Thr Arg Gly Asp Gly Arg Lys Tyr Pro Glu Leu Val Leu
            185                 190                 195

GAC ACA GAA CTG GAT CGC GAG GAG CAG GCC GAG CTC AGA TTA ACC TTG    1398
Asp Thr Glu Leu Asp Arg Glu Glu Gln Ala Glu Leu Arg Leu Thr Leu
            200                 205                 210

ACA GCG GTG GAC GGT GGC TCT CCA CCC CGA TCT GGC ACC GTC CAG ATC    1446
Thr Ala Val Asp Gly Gly Ser Pro Pro Arg Ser Gly Thr Val Gln Ile
            215                 220                 225

CTC ATC TTG GTC TTG GAC GCC AAT GAC AAT GCC CCG GAG TTT GTG CAG    1494
Leu Ile Leu Val Leu Asp Ala Asn Asp Asn Ala Pro Glu Phe Val Gln
            230                 235                 240

GCG CTC TAC GAG GTG CAG GTC CCA GAG AAC AGC CCA GTA GGC TCC CTA    1542
Ala Leu Tyr Glu Val Gln Val Pro Glu Asn Ser Pro Val Gly Ser Leu
245             250                 255                 260

GTT GTC AAG GTC TCT GCT AGG GAT TTA GAC ACT GGG ACA AAT GGA GAG    1590
Val Val Lys Val Ser Ala Arg Asp Leu Asp Thr Gly Thr Asn Gly Glu
            265                 270                 275

ATA TCA TAC TCC CTT TAT TAC AGC TCT CAG GAG ATA GAC AAA CCT TTT    1638
Ile Ser Tyr Ser Leu Tyr Tyr Ser Ser Gln Glu Ile Asp Lys Pro Phe
            280                 285                 290

GAG CTA AGC AGC CTT TCA GGA GAA ATT CGA CTA ATT AAA AAA CTA GAT    1686
Glu Leu Ser Ser Leu Ser Gly Glu Ile Arg Leu Ile Lys Lys Leu Asp
            295                 300                 305

TTT GAG ACA ATG TCT TCA TAT GAT CTA GAT ATA GAG GCA TCT GAT GGC    1734
Phe Glu Thr Met Ser Ser Tyr Asp Leu Asp Ile Glu Ala Ser Asp Gly
            310                 315                 320

GGG GGA CTT TCT GGA AAA TGC TCT GTC TCT GTT AAG GTG CTG GAT GTT    1782
Gly Gly Leu Ser Gly Lys Cys Ser Val Ser Val Lys Val Leu Asp Val
325             330                 335                 340

AAC GAT AAC TTC CCG GAA CTA AGT ATT TCA TCA CTT ACC AGC CCT ATT    1830
Asn Asp Asn Phe Pro Glu Leu Ser Ile Ser Ser Leu Thr Ser Pro Ile
            345                 350                 355

CCC GAG AAT TCT CCA GAG ACA GAA GTG GCC CTG TTT AGG ATT AGA GAC    1878
Pro Glu Asn Ser Pro Glu Thr Glu Val Ala Leu Phe Arg Ile Arg Asp
            360                 365                 370

CGA GAC TCT GGA GAA AAT GGA AAA ATG ATT TGC TCA ATT CAG GAT GAT    1926
Arg Asp Ser Gly Glu Asn Gly Lys Met Ile Cys Ser Ile Gln Asp Asp
            375                 380                 385

GTT CCT TTT AAG CTA AAA CCT TCT GTT GAG AAT TTC TAC AGG CTG GTA    1974
Val Pro Phe Lys Leu Lys Pro Ser Val Glu Asn Phe Tyr Arg Leu Val
            390                 395                 400

ACA GAA GGG GCG CTG GAC AGA GAG ACC AGA GCC GAG TAC AAC ATC ACC    2022
Thr Glu Gly Ala Leu Asp Arg Glu Thr Arg Ala Glu Tyr Asn Ile Thr
405             410                 415                 420

ATC ACC ATC ACA GAC TTG GGG ACT CCA AGG CTG AAA ACC GAG CAG AGC    2070
Ile Thr Ile Thr Asp Leu Gly Thr Pro Arg Leu Lys Thr Glu Gln Ser
            425                 430                 435

ATA ACC GTG CTG GTG TCG GAC GTC AAT GAC AAC GCC CCC GCC TTC ACC    2118
Ile Thr Val Leu Val Ser Asp Val Asn Asp Asn Ala Pro Ala Phe Thr
            440                 445                 450

CAA ACC TCC TAC ACC CTG TTC GTC CGC GAG AAC AAC AGC CCC GCC CTG    2166
Gln Thr Ser Tyr Thr Leu Phe Val Arg Glu Asn Asn Ser Pro Ala Leu
            455                 460                 465

CAC ATC GGC AGT GTC AGC GCC ACA GAC AGA GAC TCG GGC ACC AAC GCC    2214
His Ile Gly Ser Val Ser Ala Thr Asp Arg Asp Ser Gly Thr Asn Ala
            470                 475                 480

CAG GTC ACC TAC TCG CTG CTG CCG CCC CAG GAC CCG CAC CTG CCC CTA    2262
Gln Val Thr Tyr Ser Leu Leu Pro Pro Gln Asp Pro His Leu Pro Leu
485             490                 495                 500
```

-continued

```
ACC TCC CTG GTC TCC ATT AAC ACG GAC AAC GGC CAC CTG TTC GCT CTC       2310
Thr Ser Leu Val Ser Ile Asn Thr Asp Asn Gly His Leu Phe Ala Leu
            505                 510                 515

CAG TCG CTG GAC TAC GAG GCC CTG CAG GCT TTC GAG TTC CGC GTG GGC       2358
Gln Ser Leu Asp Tyr Glu Ala Leu Gln Ala Phe Glu Phe Arg Val Gly
            520                 525                 530

GCC ACA GAC CGC GGC TTC CCG GCG CTG AGC AGC GAG GCG CTG GTG CGA       2406
Ala Thr Asp Arg Gly Phe Pro Ala Leu Ser Ser Glu Ala Leu Val Arg
            535                 540                 545

GTG CTG GTG CTG GAC GCC AAC GAC AAC TCG CCC TTC GTG CTG TAC CCG       2454
Val Leu Val Leu Asp Ala Asn Asp Asn Ser Pro Phe Val Leu Tyr Pro
    550                 555                 560

CTG CAG AAC GGC TCC GCG CCC TGC ACC GAG CTG GTG CCC CGG GCG GCC       2502
Leu Gln Asn Gly Ser Ala Pro Cys Thr Glu Leu Val Pro Arg Ala Ala
565                 570                 575                 580

GAG CCG GGC TAC CTG GTG ACC AAG GTG GTG GCG GTG GAC GGC GAC TCG       2550
Glu Pro Gly Tyr Leu Val Thr Lys Val Val Ala Val Asp Gly Asp Ser
                585                 590                 595

GGC CAG AAC GCC TGG CTG TCG TAC CAG CTG CTC AAG GCC ACG GAG CCC       2598
Gly Gln Asn Ala Trp Leu Ser Tyr Gln Leu Leu Lys Ala Thr Glu Pro
            600                 605                 610

GGG CTG TTC GGC GTG TGG GCG CAC AAT GGC GAG GTG CGC ACC GCC AGG       2646
Gly Leu Phe Gly Val Trp Ala His Asn Gly Glu Val Arg Thr Ala Arg
            615                 620                 625

CTG CTG AGC GAG CGC GAC GTG GCC AAG CAC AGG CTA GTG GTG CTG GTC       2694
Leu Leu Ser Glu Arg Asp Val Ala Lys His Arg Leu Val Val Leu Val
    630                 635                 640

AAG GAC AAT GGC GAG CCT CCG CGC TCG GCC ACA GCC ACG CTG CAA GTG       2742
Lys Asp Asn Gly Glu Pro Pro Arg Ser Ala Thr Ala Thr Leu Gln Val
645                 650                 655                 660

CTC CTG GTG GAC GGC TTC TCT CAG CCC TAC CTG CCG CTC CCA GAG GCG       2790
Leu Leu Val Asp Gly Phe Ser Gln Pro Tyr Leu Pro Leu Pro Glu Ala
                665                 670                 675

GCC CCG GCC CAA GCC CAG GCC GAC TCG CTT ACC GTC TAC CTG GTG GTG       2838
Ala Pro Ala Gln Ala Gln Ala Asp Ser Leu Thr Val Tyr Leu Val Val
            680                 685                 690

GCA TTG GCC TCG GTG TCT TCG CTC TTC CTC TTC TCG GTG TTC CTG TTC       2886
Ala Leu Ala Ser Val Ser Ser Leu Phe Leu Phe Ser Val Phe Leu Phe
            695                 700                 705

GTG GCA GTG CGG CTG TGC AGG AGG AGC AGG GCG GCC TCA GTG GGT CGC       2934
Val Ala Val Arg Leu Cys Arg Arg Ser Arg Ala Ala Ser Val Gly Arg
    710                 715                 720

TGC TCG GTG CCC GAG GGC CCC TTT CCA GGG CAT CTG GTG GAC GTG AGC       2982
Cys Ser Val Pro Glu Gly Pro Phe Pro Gly His Leu Val Asp Val Ser
725                 730                 735                 740

GGC ACC GGG ACC CTT TCC CAG AGC TAC CAG TAC GAG GTG TGT CTG ACG       3030
Gly Thr Gly Thr Leu Ser Gln Ser Tyr Gln Tyr Glu Val Cys Leu Thr
                745                 750                 755

GGA GGC TCT GAA AGT AAT GAT TTC AAG TTC TTG AAG CCT ATA TTC CCA       3078
Gly Gly Ser Glu Ser Asn Asp Phe Lys Phe Leu Lys Pro Ile Phe Pro
            760                 765                 770

AAT ATT GTA AGC CAG GAC TCT AGG AGG AAA TCA GAA TTT CTA GAA           3123
Asn Ile Val Ser Gln Asp Ser Arg Arg Lys Ser Glu Phe Leu Glu
            775                 780                 785

TAATGTAGGT ATCTGTAGCT TTCCGACCGT CTGTTAATTT TGTCTTCCTC ACTTTTCACC     3183

TTAGTTTTTT TTAACCCTTT AGTAATCTTG AATTCTACTT TTTTTTAAAT TTCTACTGTT     3243

GTCTTTAGTA ATGTTACTCA TTTCCTTTGT CTGATTGTTA GTTTTCAAAT TATTGTATTA     3303

TTATAAATAT TTTATATCAG GAAAGTTCAT ATTTCTGAAT AAATTAATAG                3353
```

(2) INFORMATION FOR SEQ ID NO: 110:

(i) SEQUENCE CHARACTERISTICS:
        (A) LENGTH: 787 amino acids
        (B) TYPE: amino acid
        (D) TOPOLOGY: linear (ii) MOLECULE TYPE: protein (xi) SEQUENCE DESCRIPTION: SEQ ID NO: 110:

```
Met Glu Pro Ala Gly Glu Arg Phe Pro Glu Gln Arg Gln Val Leu Ile
 1               5                  10                  15

Leu Leu Leu Leu Leu Glu Val Thr Leu Ala Gly Trp Glu Pro Arg Arg
                20                  25                  30

Tyr Ser Val Met Glu Glu Thr Glu Arg Gly Ser Phe Val Ala Asn Leu
             35                  40                  45

Ala Asn Asp Leu Gly Leu Gly Val Gly Glu Leu Ala Glu Arg Gly Ala
         50                  55                  60

Arg Val Val Ser Glu Asp Asn Glu Gln Gly Leu Gln Leu Asp Leu Gln
 65                  70                  75                  80

Thr Gly Gln Leu Ile Leu Asn Glu Lys Leu Asp Arg Glu Lys Leu Cys
                 85                  90                  95

Gly Pro Thr Glu Pro Cys Ile Met His Phe Gln Val Leu Leu Lys Lys
            100                 105                 110

Pro Leu Glu Val Phe Arg Ala Glu Leu Leu Val Thr Asp Ile Asn Asp
            115                 120                 125

His Ser Pro Glu Phe Pro Glu Arg Glu Met Thr Leu Lys Ile Pro Glu
130                 135                 140

Thr Ser Ser Leu Gly Thr Val Phe Pro Leu Lys Lys Ala Arg Asp Leu
145                 150                 155                 160

Asp Val Gly Ser Asn Asn Val Gln Asn Tyr Asn Ile Ser Pro Asn Ser
                165                 170                 175

His Phe His Val Ser Thr Arg Thr Arg Gly Asp Gly Arg Lys Tyr Pro
                180                 185                 190

Glu Leu Val Leu Asp Thr Glu Leu Asp Arg Glu Glu Gln Ala Glu Leu
            195                 200                 205

Arg Leu Thr Leu Thr Ala Val Asp Gly Gly Ser Pro Pro Arg Ser Gly
210                 215                 220

Thr Val Gln Ile Leu Ile Leu Val Leu Asp Ala Asn Asp Asn Ala Pro
225                 230                 235                 240

Glu Phe Val Gln Ala Leu Tyr Glu Val Gln Val Pro Glu Asn Ser Pro
            245                 250                 255

Val Gly Ser Leu Val Val Lys Val Ser Ala Arg Asp Leu Asp Thr Gly
            260                 265                 270

Thr Asn Gly Glu Ile Ser Tyr Ser Leu Tyr Tyr Ser Ser Gln Glu Ile
            275                 280                 285

Asp Lys Pro Phe Glu Leu Ser Ser Leu Ser Gly Glu Ile Arg Leu Ile
            290                 295                 300

Lys Lys Leu Asp Phe Glu Thr Met Ser Ser Tyr Asp Leu Asp Ile Glu
305                 310                 315                 320

Ala Ser Asp Gly Gly Gly Leu Ser Gly Lys Cys Ser Val Ser Val Lys
                325                 330                 335

Val Leu Asp Val Asn Asp Asn Phe Pro Glu Leu Ser Ile Ser Ser Leu
            340                 345                 350
```

```
Thr Ser Pro Ile Pro Glu Asn Ser Pro Glu Thr Glu Val Ala Leu Phe
        355                 360                 365

Arg Ile Arg Asp Arg Asp Ser Gly Glu Asn Gly Lys Met Ile Cys Ser
    370                 375                 380

Ile Gln Asp Asp Val Pro Phe Lys Leu Lys Pro Ser Val Glu Asn Phe
385                 390                 395                 400

Tyr Arg Leu Val Thr Glu Gly Ala Leu Asp Arg Glu Thr Arg Ala Glu
                405                 410                 415

Tyr Asn Ile Thr Ile Thr Ile Thr Asp Leu Gly Thr Pro Arg Leu Lys
                420                 425                 430

Thr Glu Gln Ser Ile Thr Val Leu Val Ser Asp Val Asn Asp Asn Ala
                435                 440                 445

Pro Ala Phe Thr Gln Thr Ser Tyr Thr Leu Phe Val Arg Glu Asn Asn
    450                 455                 460

Ser Pro Ala Leu His Ile Gly Ser Val Ser Ala Thr Asp Arg Asp Ser
465                 470                 475                 480

Gly Thr Asn Ala Gln Val Thr Tyr Ser Leu Leu Pro Pro Gln Asp Pro
                485                 490                 495

His Leu Pro Leu Thr Ser Leu Val Ser Ile Asn Thr Asp Asn Gly His
                500                 505                 510

Leu Phe Ala Leu Gln Ser Leu Asp Tyr Glu Ala Leu Gln Ala Phe Glu
                515                 520                 525

Phe Arg Val Gly Ala Thr Asp Arg Gly Phe Pro Ala Leu Ser Ser Glu
    530                 535                 540

Ala Leu Val Arg Val Leu Val Leu Asp Ala Asn Asp Asn Ser Pro Phe
545                 550                 555                 560

Val Leu Tyr Pro Leu Gln Asn Gly Ser Ala Pro Cys Thr Glu Leu Val
                565                 570                 575

Pro Arg Ala Ala Glu Pro Gly Tyr Leu Val Thr Lys Val Val Ala Val
                580                 585                 590

Asp Gly Asp Ser Gly Gln Asn Ala Trp Leu Ser Tyr Gln Leu Leu Lys
                595                 600                 605

Ala Thr Glu Pro Gly Leu Phe Gly Val Trp Ala His Asn Gly Glu Val
    610                 615                 620

Arg Thr Ala Arg Leu Leu Ser Glu Arg Asp Val Ala Lys His Arg Leu
625                 630                 635                 640

Val Val Leu Val Lys Asp Asn Gly Glu Pro Pro Arg Ser Ala Thr Ala
                645                 650                 655

Thr Leu Gln Val Leu Leu Val Asp Gly Phe Ser Gln Pro Tyr Leu Pro
                660                 665                 670

Leu Pro Glu Ala Ala Pro Ala Gln Ala Gln Ala Asp Ser Leu Thr Val
    675                 680                 685

Tyr Leu Val Val Ala Leu Ala Ser Val Ser Ser Leu Phe Leu Phe Ser
    690                 695                 700

Val Phe Leu Phe Val Ala Val Arg Leu Cys Arg Arg Ser Arg Ala Ala
705                 710                 715                 720

Ser Val Gly Arg Cys Ser Val Pro Glu Gly Pro Phe Pro Gly His Leu
                725                 730                 735

Val Asp Val Ser Gly Thr Gly Thr Leu Ser Gln Ser Tyr Gln Tyr Glu
                740                 745                 750

Val Cys Leu Thr Gly Gly Ser Glu Ser Asn Asp Phe Lys Phe Leu Lys
                755                 760                 765

Pro Ile Phe Pro Asn Ile Val Ser Gln Asp Ser Arg Arg Lys Ser Glu
```

Phe Leu Glu
785

(2) INFORMATION FOR SEQ ID NO: 111:

(i) SEQUENCE CHARACTERISTICS:
        (A) LENGTH: 3033 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 138..2528

(xi) SEQUENCE DESCRIPTION: SEQ ID NO: 111:

```
GTGATTGGAC GTGTTTTTGT GACTATTTGG GAAGAAGACA CCTTCCTAAT CAGATTTACT      60

CCAATATCTT CCCGGACCCT CATGAGTGGA TTGCAATTGA CTTGAAGAAG CAGCACCCTC     120

AGGACTGAAT CTGAACA ATG GAG ACA GCA CTA GCA AAA ATA CCA CAG CAA        170
                Met Glu Thr Ala Leu Ala Lys Ile Pro Gln Gln
                 1               5                  10

AGG CAA GTC TTT TTT CTT ACT ATA TTG TCG TTA TTG TGG AAG TCT AGC       218
Arg Gln Val Phe Phe Leu Thr Ile Leu Ser Leu Leu Trp Lys Ser Ser
             15                  20                  25

TCT GAG GCC ATT AGA TAT TCC ATG CCA GAA GAA ACA GAG AGT GGC TAT       266
Ser Glu Ala Ile Arg Tyr Ser Met Pro Glu Glu Thr Glu Ser Gly Tyr
         30                  35                  40

ATG GTG GCT AAC CTG GCG AAA GAT CTG GGG ATC AGG GTT GGA GAA CTG       314
Met Val Ala Asn Leu Ala Lys Asp Leu Gly Ile Arg Val Gly Glu Leu
     45                  50                  55

TCC TCT AGA GGA GCT CAA ATC CAT TAC AAA GGA AAC AAA GAA CTT TTG       362
Ser Ser Arg Gly Ala Gln Ile His Tyr Lys Gly Asn Lys Glu Leu Leu
 60                  65                  70                  75

CAG CTG GAT GCA GAG ACT GGG AAT TTG TTC TTA AAG GAA AAA CTA GAC       410
Gln Leu Asp Ala Glu Thr Gly Asn Leu Phe Leu Lys Glu Lys Leu Asp
             80                  85                  90

AGA GAA CTG CTG TGT GGA GAG ACA GAA CCC TGT GTG CTG AAC TTC CAG       458
Arg Glu Leu Leu Cys Gly Glu Thr Glu Pro Cys Val Leu Asn Phe Gln
         95                 100                 105

ATC ATA CTG GAA AAC CCT ATG CAG TTC TTC CAA ACT GAA CTG CAG CTC       506
Ile Ile Leu Glu Asn Pro Met Gln Phe Phe Gln Thr Glu Leu Gln Leu
    110                 115                 120

ACA GAT ATA AAC GAC CAT TCT CCA GAG TTC CCC AAC AAG AAA ATG CTT       554
Thr Asp Ile Asn Asp His Ser Pro Glu Phe Pro Asn Lys Lys Met Leu
125                 130                 135

CTA ACA ATT CCT GAG AGT GCC CAT CCA GGG ACT GTG TTT CCT CTG AAG       602
Leu Thr Ile Pro Glu Ser Ala His Pro Gly Thr Val Phe Pro Leu Lys
140                 145                 150                 155

GCA GCT CGG GAC TCT GAC ATA GGG AGC AAC GCT GTT CAG AAC TAC ACA       650
Ala Ala Arg Asp Ser Asp Ile Gly Ser Asn Ala Val Gln Asn Tyr Thr
            160                 165                 170

GTC AAT CCC AAC CTC CAT TTC CAC GTC GTT ACT CAC AGT CGC ACA GAT       698
Val Asn Pro Asn Leu His Phe His Val Val Thr His Ser Arg Thr Asp
        175                 180                 185

GGC AGG AAA TAC CCA GAG CTG GTG CTG GAC AGA GCC CTG GAT AGG GAG       746
Gly Arg Lys Tyr Pro Glu Leu Val Leu Asp Arg Ala Leu Asp Arg Glu
    190                 195                 200

GAG CAG CCT GAG CTC ACT TTA ATC CTC ACT GCT CTG GAT GGT GGA GCT       794
```

```
                                                              -continued

Glu Gln Pro Glu Leu Thr Leu Ile Leu Thr Ala Leu Asp Gly Gly Ala
    205                 210                 215

CCT TCC AGG TCA GGA ACC ACC ACA GTT CAC ATA GAA GTT GTG GAC ATC        842
Pro Ser Arg Ser Gly Thr Thr Thr Val His Ile Glu Val Val Asp Ile
220                 225                 230                 235

AAT GAT AAC TCC CCC CAG TTT GTA CAG TCA CTC TAT AAG GTG CAA GTT        890
Asn Asp Asn Ser Pro Gln Phe Val Gln Ser Leu Tyr Lys Val Gln Val
                240                 245                 250

CCT GAG AAT AAT CCC CTC AAT GCC TTT GTT GTC ACG GTC TCT GCC ACG        938
Pro Glu Asn Asn Pro Leu Asn Ala Phe Val Val Thr Val Ser Ala Thr
            255                 260                 265

GAT TTA GAT GCT GGG GTA TAT GGC AAT GTG ACC TAT TCT CTG TTT CAA        986
Asp Leu Asp Ala Gly Val Tyr Gly Asn Val Thr Tyr Ser Leu Phe Gln
        270                 275                 280

GGG TAT GGG GTA TTT CAA CCA TTT GTA ATA GAC GAA ATC ACT GGA GAA       1034
Gly Tyr Gly Val Phe Gln Pro Phe Val Ile Asp Glu Ile Thr Gly Glu
    285                 290                 295

ATC CAT CTG AGC AAA GAG CTG GAT TTT GAG GAA ATT AGC AAT CAT AAC       1082
Ile His Leu Ser Lys Glu Leu Asp Phe Glu Glu Ile Ser Asn His Asn
300                 305                 310                 315

ATA GAA ATC GCA GCC ACA GAT GGA GGA GGC CTT TCA GGA AAA TGC ACT       1130
Ile Glu Ile Ala Ala Thr Asp Gly Gly Gly Leu Ser Gly Lys Cys Thr
                320                 325                 330

GTG GCT GTA CAG GTG TTG GAT GTG AAT GAC AAC GCC CCA GAG TTG ACA       1178
Val Ala Val Gln Val Leu Asp Val Asn Asp Asn Ala Pro Glu Leu Thr
            335                 340                 345

ATT AGG AAG CTC ACA GTC CTG GTC CCA GAA AAT TCC GCA GAG ACT GTA       1226
Ile Arg Lys Leu Thr Val Leu Val Pro Glu Asn Ser Ala Glu Thr Val
        350                 355                 360

GTT GCT GTT TTT AGT GTT TCT GAT TCT GAT TCG GGG GAC AAT GGA AGG       1274
Val Ala Val Phe Ser Val Ser Asp Ser Asp Ser Gly Asp Asn Gly Arg
    365                 370                 375

ATG GTG TGT TCT ATT CCG AAC AAT ATC CCA TTT CTC CTG AAA CCC ACA       1322
Met Val Cys Ser Ile Pro Asn Asn Ile Pro Phe Leu Leu Lys Pro Thr
380                 385                 390                 395

TTT GAG AAT TAT TAC ACG TTA GTG ACT GAG GGG CCA CTT GAT AGA GAG       1370
Phe Glu Asn Tyr Tyr Thr Leu Val Thr Glu Gly Pro Leu Asp Arg Glu
                400                 405                 410

AAC AGA GCT GAG TAC AAC ATC ACC ATC ACG GTC TCA GAT CTG GGC ACA       1418
Asn Arg Ala Glu Tyr Asn Ile Thr Ile Thr Val Ser Asp Leu Gly Thr
            415                 420                 425

CCC AGG CTC ACA ACC CAG CAC ACC ATA ACA GTG CAA GTG TCC GAC ATC       1466
Pro Arg Leu Thr Thr Gln His Thr Ile Thr Val Gln Val Ser Asp Ile
        430                 435                 440

AAC GAC AAC GCC CCT GCC TTC ACC CAA ACC TCC TAC ACC ATG TTT GTC       1514
Asn Asp Asn Ala Pro Ala Phe Thr Gln Thr Ser Tyr Thr Met Phe Val
    445                 450                 455

CAC GAG AAC AAC AGC CCC GCC CTG CAC ATA GGC ACC ATC AGT GCC ACA       1562
His Glu Asn Asn Ser Pro Ala Leu His Ile Gly Thr Ile Ser Ala Thr
460                 465                 470                 475

GAC TCA GAC TCA GGC TCC AAT GCC CAC ATC ACC TAC TCG CTG CTG CCG       1610
Asp Ser Asp Ser Gly Ser Asn Ala His Ile Thr Tyr Ser Leu Leu Pro
                480                 485                 490

CCT GAT GAC CCG CAG CTG GCC CTC GAC TCA CTC ATC TCC ATC AAT GTT       1658
Pro Asp Asp Pro Gln Leu Ala Leu Asp Ser Leu Ile Ser Ile Asn Val
            495                 500                 505

GAC AAT GGG CAG CTG TTC GCG CTC AGA GCT CTA GAC TAT GAG GCA CTG       1706
Asp Asn Gly Gln Leu Phe Ala Leu Arg Ala Leu Asp Tyr Glu Ala Leu
        510                 515                 520
```

```
CAG TCC TTC GAG TTC TAC GTG GGC GCT ACA GAT GGA GGC TCA CCC GCG      1754
Gln Ser Phe Glu Phe Tyr Val Gly Ala Thr Asp Gly Gly Ser Pro Ala
    525                 530                 535

CTC AGC AGC CAG ACT CTG GTG CGG ATG GTG GTG CTG GAT GAC AAT GAC      1802
Leu Ser Ser Gln Thr Leu Val Arg Met Val Val Leu Asp Asp Asn Asp
540                 545                 550                 555

AAT GCC CCC TTC GTG CTC TAC CCA CTG CAG AAT GCC TCA GCA CCC TGT      1850
Asn Ala Pro Phe Val Leu Tyr Pro Leu Gln Asn Ala Ser Ala Pro Cys
                560                 565                 570

ACT GAG CTA CTG CCT AGG GCA GCA GAG CCC GGC TAC CTG ATC ACC AAA      1898
Thr Glu Leu Leu Pro Arg Ala Ala Glu Pro Gly Tyr Leu Ile Thr Lys
            575                 580                 585

GTG GTG GCT GTG GAT CGC GAC TCT GGA CAG AAT GCT TGG CTG TCG TTC      1946
Val Val Ala Val Asp Arg Asp Ser Gly Gln Asn Ala Trp Leu Ser Phe
        590                 595                 600

CAG CTA CTT AAA GCT ACA GAG CCA GGG CTG TTC AGT GTA TGG GCA CAC      1994
Gln Leu Leu Lys Ala Thr Glu Pro Gly Leu Phe Ser Val Trp Ala His
    605                 610                 615

AAT GGT GAA GTG CGC ACC ACT AGG CTG CTG AGT GAG CGA GAT GCT CAG      2042
Asn Gly Glu Val Arg Thr Thr Arg Leu Leu Ser Glu Arg Asp Ala Gln
620                 625                 630                 635

AAG CAC AAG CTA CTG CTG CTG GTC AAG GAC AAT GGC GAT CCT CTG CGC      2090
Lys His Lys Leu Leu Leu Leu Val Lys Asp Asn Gly Asp Pro Leu Arg
                640                 645                 650

TCT GCC AAT GTC ACT CTT CAC GTG CTA GTG GTG GAT GGC TTC TCG CAG      2138
Ser Ala Asn Val Thr Leu His Val Leu Val Val Asp Gly Phe Ser Gln
            655                 660                 665

CCT TAC CTA CCA TTG GCT GAG GTG GCA CAG GAT TCC ATG CAA GAT AAT      2186
Pro Tyr Leu Pro Leu Ala Glu Val Ala Gln Asp Ser Met Gln Asp Asn
        670                 675                 680

TAC GAC GTT CTC ACA CTG TAC CTA GTC ATT GCC TTG GCA TCT GTA TCT      2234
Tyr Asp Val Leu Thr Leu Tyr Leu Val Ile Ala Leu Ala Ser Val Ser
    685                 690                 695

TCT CTC TTC CTC TTG TCT GTA GTG CTG TTT GTG GGG GTG AGG CTG TGC      2282
Ser Leu Phe Leu Leu Ser Val Val Leu Phe Val Gly Val Arg Leu Cys
700                 705                 710                 715

AGG AGG GCC AGG GAG GCC TCC TTG GGT GAC TAC TCT GTG CCT GAG GGA      2330
Arg Arg Ala Arg Glu Ala Ser Leu Gly Asp Tyr Ser Val Pro Glu Gly
                720                 725                 730

CAC TTT CCT AGC CAC TTG GTG GAT GTC AGC GGT GCC GGG ACC CTG TCC      2378
His Phe Pro Ser His Leu Val Asp Val Ser Gly Ala Gly Thr Leu Ser
            735                 740                 745

CAG AGT TAT CAA TAT GAG GTG TGT CTT AAT GGA GGT ACT AGA ACA AAT      2426
Gln Ser Tyr Gln Tyr Glu Val Cys Leu Asn Gly Gly Thr Arg Thr Asn
        750                 755                 760

GAG TTT AAC TTT CTT AAA CCA TTG TTT CCT ATC CTT CCG ACC CAG GCT      2474
Glu Phe Asn Phe Leu Lys Pro Leu Phe Pro Ile Leu Pro Thr Gln Ala
    765                 770                 775

GCT GCT GCT GAA GAA AGA GAA AAC GCT GTT GTG CAC AAT AGC GTT GGA      2522
Ala Ala Ala Glu Glu Arg Glu Asn Ala Val Val His Asn Ser Val Gly
780                 785                 790                 795

TTC TAT TAGAGCACTG ATTTTGAAGT GGTGGTTACC TCATTTTTCC TTAACTATCC       2578
Phe Tyr

CTGATGTAGA ATGGTGTAGT GCCGTGAATC AACTCCTGAG ATATATGTTC ATTTTATCCT    2638

TTGTTTTGAA TCAAACTATT CAGATGTGAT CCTACTCTAG AGAATTTGGT TCTACTCCAT    2698

TGTGTTTGTT TAGATTTCTA CGCCATACCA GTGCATGCTG GGTTGTTTTT TTTTTTACAA    2758

TTATTATAAC TTTGCTTTGG AGGGGAACTC ATATTCGCTG TAACGAATTG GAACCACTTT    2818
```

| CATTGTTAGA GATGCCTTGC TTTGTTGTGT TATTTCAGAC AGGGTCTTAA ATTGTAGCCC | 2878 |
| TGGGTGACCT GAAATGACTA TGTACAGACT GACTTTGAAT TTGTGGCAGT CCATCTGCCT | 2938 |
| CTGTTGTCCT ATGTTGGGAT TGTGAGCATG CATGAGTAGG CTCAGCTGTG GTGAGCGACC | 2998 |
| TTAATAAAAA TCAAATACTA AAAAAAAAAA AAAAA | 3033 |

(2) INFORMATION FOR SEQ ID NO: 112:

(i) SEQUENCE CHARACTERISTICS:
(A) LENGTH: 797 amino acids
(B) TYPE: amino acid
(D) TOPOLOGY: linear (ii) MOLECULE TYPE: protein (xi) SEQUENCE DESCRIPTION: SEQ ID NO: 112:

```
Met Glu Thr Ala Leu Ala Lys Ile Pro Gln Gln Arg Gln Val Phe Phe
 1               5                  10                  15

Leu Thr Ile Leu Ser Leu Leu Trp Lys Ser Ser Glu Ala Ile Arg
                 20                  25                  30

Tyr Ser Met Pro Glu Glu Thr Glu Ser Gly Tyr Met Val Ala Asn Leu
             35                  40                  45

Ala Lys Asp Leu Gly Ile Arg Val Gly Glu Leu Ser Ser Arg Gly Ala
         50                  55                  60

Gln Ile His Tyr Lys Gly Asn Lys Glu Leu Leu Gln Leu Asp Ala Glu
 65                  70                  75                  80

Thr Gly Asn Leu Phe Leu Lys Glu Lys Leu Asp Arg Glu Leu Leu Cys
                 85                  90                  95

Gly Glu Thr Glu Pro Cys Val Leu Asn Phe Gln Ile Ile Leu Glu Asn
            100                 105                 110

Pro Met Gln Phe Phe Gln Thr Glu Leu Gln Leu Thr Asp Ile Asn Asp
            115                 120                 125

His Ser Pro Glu Phe Pro Asn Lys Lys Met Leu Leu Thr Ile Pro Glu
        130                 135                 140

Ser Ala His Pro Gly Thr Val Phe Pro Leu Lys Ala Ala Arg Asp Ser
145                 150                 155                 160

Asp Ile Gly Ser Asn Ala Val Gln Asn Tyr Thr Val Asn Pro Asn Leu
                165                 170                 175

His Phe His Val Val Thr His Ser Arg Thr Asp Gly Arg Lys Tyr Pro
            180                 185                 190

Glu Leu Val Leu Asp Arg Ala Leu Asp Arg Glu Gln Pro Glu Leu
            195                 200                 205

Thr Leu Ile Leu Thr Ala Leu Asp Gly Gly Ala Pro Ser Arg Ser Gly
        210                 215                 220

Thr Thr Thr Val His Ile Glu Val Val Asp Ile Asn Asp Asn Ser Pro
225                 230                 235                 240

Gln Phe Val Gln Ser Leu Tyr Lys Val Gln Val Pro Glu Asn Asn Pro
                245                 250                 255

Leu Asn Ala Phe Val Val Thr Val Ser Ala Thr Asp Leu Asp Ala Gly
            260                 265                 270

Val Tyr Gly Asn Val Thr Tyr Ser Leu Phe Gln Gly Tyr Gly Val Phe
        275                 280                 285

Gln Pro Phe Val Ile Asp Glu Ile Thr Gly Glu Ile His Leu Ser Lys
    290                 295                 300

Glu Leu Asp Phe Glu Glu Ile Ser Asn His Asn Ile Glu Ile Ala Ala
305                 310                 315                 320
```

-continued

```
Thr Asp Gly Gly Gly Leu Ser Gly Lys Cys Thr Val Ala Val Gln Val
                325                 330                 335
Leu Asp Val Asn Asp Asn Ala Pro Glu Leu Thr Ile Arg Lys Leu Thr
            340                 345                 350
Val Leu Val Pro Glu Asn Ser Ala Glu Thr Val Val Ala Val Phe Ser
                355                 360                 365
Val Ser Asp Ser Asp Ser Gly Asp Asn Gly Arg Met Val Cys Ser Ile
            370                 375                 380
Pro Asn Asn Ile Pro Phe Leu Leu Lys Pro Thr Phe Glu Asn Tyr Tyr
385                 390                 395                 400
Thr Leu Val Thr Glu Gly Pro Leu Asp Arg Glu Asn Arg Ala Glu Tyr
                405                 410                 415
Asn Ile Thr Ile Thr Val Ser Asp Leu Gly Thr Pro Arg Leu Thr Thr
                420                 425                 430
Gln His Thr Ile Thr Val Gln Val Ser Asp Ile Asn Asp Asn Ala Pro
            435                 440                 445
Ala Phe Thr Gln Thr Ser Tyr Thr Met Phe Val His Glu Asn Asn Ser
            450                 455                 460
Pro Ala Leu His Ile Gly Thr Ile Ser Ala Thr Asp Ser Asp Ser Gly
465                 470                 475                 480
Ser Asn Ala His Ile Thr Tyr Ser Leu Leu Pro Pro Asp Asp Pro Gln
                485                 490                 495
Leu Ala Leu Asp Ser Leu Ile Ser Ile Asn Val Asp Asn Gly Gln Leu
            500                 505                 510
Phe Ala Leu Arg Ala Leu Asp Tyr Glu Ala Leu Gln Ser Phe Glu Phe
            515                 520                 525
Tyr Val Gly Ala Thr Asp Gly Gly Ser Pro Ala Leu Ser Ser Gln Thr
            530                 535                 540
Leu Val Arg Met Val Val Leu Asp Asp Asn Asp Ala Pro Phe Val
545                 550                 555                 560
Leu Tyr Pro Leu Gln Asn Ala Ser Ala Pro Cys Thr Glu Leu Leu Pro
                565                 570                 575
Arg Ala Ala Glu Pro Gly Tyr Leu Ile Thr Lys Val Val Ala Val Asp
            580                 585                 590
Arg Asp Ser Gly Gln Asn Ala Trp Leu Ser Phe Gln Leu Leu Lys Ala
        595                 600                 605
Thr Glu Pro Gly Leu Phe Ser Val Trp Ala His Asn Gly Glu Val Arg
        610                 615                 620
Thr Thr Arg Leu Leu Ser Glu Arg Asp Ala Gln Lys His Lys Leu Leu
625                 630                 635                 640
Leu Leu Val Lys Asp Asn Gly Asp Pro Leu Arg Ser Ala Asn Val Thr
                645                 650                 655
Leu His Val Leu Val Asp Gly Phe Ser Gln Pro Tyr Leu Pro Leu
                660                 665                 670
Ala Glu Val Ala Gln Asp Ser Met Gln Asp Asn Tyr Asp Val Leu Thr
            675                 680                 685
Leu Tyr Leu Val Ile Ala Leu Ala Ser Val Ser Ser Leu Phe Leu Leu
            690                 695                 700
Ser Val Val Leu Phe Val Gly Val Arg Leu Cys Arg Arg Ala Arg Glu
705                 710                 715                 720
Ala Ser Leu Gly Asp Tyr Ser Val Pro Glu Gly His Phe Pro Ser His
                725                 730                 735
```

-continued

```
Leu Val Asp Val Ser Gly Ala Gly Thr Leu Ser Gln Ser Tyr Gln Tyr
            740                 745                 750

Glu Val Cys Leu Asn Gly Gly Thr Arg Thr Asn Glu Phe Asn Phe Leu
            755                 760                 765

Lys Pro Leu Phe Pro Ile Leu Pro Thr Gln Ala Ala Ala Glu Glu
    770                 775                 780

Arg Glu Asn Ala Val Val His Asn Ser Val Gly Phe Tyr
785                 790                 795
```

(2) INFORMATION FOR SEQ ID NO: 113:

(i) SEQUENCE CHARACTERISTICS:
        (A) LENGTH: 2347 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 113:

```
AAAACACGGG GGAAATGACA GTAGCAAAGA ATCTGGACTA TGAAGAATGC TCATTGTATG      60

AAATGGAAAT ACAGGCTGAA GATGTGGGGG CGCTTCTGGG GAGGAGCAAA GTGGTAATTA     120

TGGTAGAAGA TGTAAATGAC AATCGGCCAG AAGTGACCAT TACATCCTTG TTTAACCCGG     180

TATTGGAAAA TTCTCTTCCC GGGACAGTAA TTGCCTTCTT GAATGTGCAT GACCGAGACT     240

CTGGAAAGAA CGGCCAAGTT GTCTGTTACA CGCATGATAA CTTACCTTTT AAATTAGAAA     300

AGTCAATAGA TAATTATTAT AGATTGGTGA CATGGAAATA TTTGGACCGA GAAAAGTCT     360

CCATCTACAA TATCACAGTG ATAGCCTCAG ATCTAGGAGC CCACTCTGTC ACTGAAACTT     420

ACATTGCCCT GATTGTGGCA GACACTAATG ACAACCCTCC TCGTTTTCCT CACACCTCCT     480

ACACAGCCTA TATTCCAGAG AACAACCTGA GGGGCGCCTC CATCTTCTCA CTGACTGCAC     540

ATGATCCTGA CAGTCAGGAA AATGCACAGG TCACTTACTC TGTGTCTGAG ACACCATAC     600

AGGGAGTGCC TTTGTCCTCT TATATCTCCA TCAACTCAGA TACTGGTGTC CTGTATGCAC     660

TGCACTCTTT TGACTTCGAG AAGATACAAG ACTTGCAGCT ACTGGTTGTT GCCACTGACA     720

GTGGAAGCCC ACCTCTCAGC AGCAATGTGT CATTGAGCTT GTTTGTGTTG GACCAGAACG     780

ACAACGCACC TGAGATTCTA TATCCTAGCT TCCCCACAGA TGGCTCCACT GGTGTGGAAC     840

TAGCACCCCG CTCTGCAGAG CCTGGATACC TAGTGACCAA AGTGGTGGCA GTGGACAAAG     900

ACTCAGGACA GAATGCTTGG CTGTCCTACC GTCTGCTGAA GGCCAGCGAA CCTGGGCTCT     960

TCTCTGTAGG ACTTCACACG GGTGAGGTGC GTACAGCGAG GGCCCTGCTG ACAGAGATG    1020

CTCTCAAACA GAATCTGGTG ATGGCCGTGC AGGACCATGG CCAACCCCCT CTCTCGGCCA    1080

CTGTAACTCT CACTGTGGCA GTGGCTAACA GCATCCCTGA GGTGTTGGCT GACTTGAGCA    1140

GCATTAGGAC CCCTGGGGTA CCAGAGGATT CTGATATCAC GCTCCACCTG GTGGTGGCAG    1200

TGGCTGTGGT CTCCTGTGTC TTCCTTGTCT TTGTCATTGT CCTCCTAGCT CTCAGGCTTC    1260

AGCGCTGGCA GAAGTCTCGC CAGCTCCAGG GCTCCAAAGG TGGATTGGCT CCTGCACCTC    1320

CATCACATTT TGTGGGCATC GACGGGGTAC AGGCTTTTCT ACAAACCTAT TCTCATGAAG    1380

TCTCGCTCAC TTCAGGCTCC CAGACAAGCC ACATTATCTT TCCTCAGCCC AACTATGCAG    1440

ACATGCTCAT TAACCAAGAA GGCTGTGAGA AAAATGATTC CTTATTAACA TCCATAGATT    1500

TTCATGAGAG TAACCGTGAA GATGCTTGCG CCCCGCAAGC CCCGCCCAAC ACTGACTGGC    1560

GTTTCTCTCA AGCCCAGAGA CCCGGCACGA GCGGATCCCA AAATGGGGAT GAAACCGGCA    1620
```

-continued

```
CCTGGCCCAA CAACCAGTTC GATACAGAGA TGCTGCAAGC CATGATCTTG GCCTCTGCCA    1680

GTGAAGCCGC TGATGGGAGC TCCACTCTGG GAGGGGGCAC TGGCACTATG GGTTTGAGCG    1740

CTCGATATGG ACCCCAGTTT ACCCTGCAGC ACGTGCCTGA CTACCGCCAG AACGTGTACA    1800

TCCCTGGCAG CAATGCCACA CTGACCAACG CAGCTGGCAA ACGAGATGGC AAGGCTCCGG    1860

CAGGCGGCAA TGGCAACAAC AACAAGTCGG GCAAGAAAGA GAAGAAGTAA TATGGAGGCC    1920

AGGCCTTGAG CCACAGGGCA GCCTCCCTCC CCAGCCAGTC CAGCTTGTCC TTACTTGTAC    1980

CCAGGCCTCA GAATTTCAGG GCTCACCCCA GGATTCTGGT AGGAGCCACA GCCAGGCCAT    2040

GCTCCCCGTT GGGAAACAGA AACAAGTGCC CAAGCCAACA CCCCCTCTTT GTACCCTAGG    2100

GGGGTTGAAT ATGCAAAGAG AGTTCTGCTG GGACCCCCTA TCCAATCAGT GATTGTACCC    2160

ACATAGGTAG CAGGGTTAGT GTGGATACAC ACACACACAC ACACACACAC ACACACACAA    2220

CCCTTGTCCT CCGCAGTGCC TGCCACTTTC TGGGACTTTC TCATCCCCCT ACGCCCTTCC    2280

TTTATCCTCT CCCACCCAGA CACAGCTGCT GGAGAATAAA TTTGGGGATG CTGATGCTAA    2340

AAAAAAA                                                              2347
```

(2) INFORMATION FOR SEQ ID NO: 114:

(i) SEQUENCE CHARACTERISTICS:
        (A) LENGTH: 2972 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1849

(xi) SEQUENCE DESCRIPTION: SEQ ID NO: 114:

```
A GAG GCT GCT CAC CAC CTG GTC CTC ACG GCC TCG GAT GGC GGC AAG          46
  Glu Ala Ala His His Leu Val Leu Thr Ala Ser Asp Gly Gly Lys
   1               5                  10                  15

CCG CCT CGC TCT AGC ACA GTG CGC ATC CAC GTG ACA GTG TTG GAT ACA        94
Pro Pro Arg Ser Ser Thr Val Arg Ile His Val Thr Val Leu Asp Thr
                 20                  25                  30

AAT GAC AAT GCC CCG GTT TTT CCT CAC CCG ATT TAC CGA GTG AAA GTC       142
Asn Asp Asn Ala Pro Val Phe Pro His Pro Ile Tyr Arg Val Lys Val
             35                  40                  45

CTT GAG AAC ATG CCC CCA GGC ACG CGG CTG CTT ACT GTA ACA GCC AGC       190
Leu Glu Asn Met Pro Pro Gly Thr Arg Leu Leu Thr Val Thr Ala Ser
         50                  55                  60

GAC CCG GAT GAG GGA ATC AAC GGA AAA GTG GCA TAC AAA TTC CGG AAA       238
Asp Pro Asp Glu Gly Ile Asn Gly Lys Val Ala Tyr Lys Phe Arg Lys
     65                  70                  75

ATT AAT GAA AAA CAA ACT CCG TTA TTC CAG CTT AAT GAA AAT ACT GGG       286
Ile Asn Glu Lys Gln Thr Pro Leu Phe Gln Leu Asn Glu Asn Thr Gly
 80                  85                  90                  95

GAA ATA TCA ATA GCA AAA AGT CTA GAT TAT GAA GAA TGT TCA TTT TAT       334
Glu Ile Ser Ile Ala Lys Ser Leu Asp Tyr Glu Glu Cys Ser Phe Tyr
                100                 105                 110

GAA ATG GAA ATA CAA GCC GAA GAT GTG GGG GCA CTT CTG GGG AGG ACC       382
Glu Met Glu Ile Gln Ala Glu Asp Val Gly Ala Leu Leu Gly Arg Thr
            115                 120                 125

AAA TTG CTC ATT TCT GTG GAA GAT GTA AAT GAC AAT AGA CCA GAA GTG       430
Lys Leu Leu Ile Ser Val Glu Asp Val Asn Asp Asn Arg Pro Glu Val
        130                 135                 140
```

```
ATC ATT ACG TCT TTG TTT AGC CCA GTG TTA GAA AAT TCT CTT CCC GGG     478
Ile Ile Thr Ser Leu Phe Ser Pro Val Leu Glu Asn Ser Leu Pro Gly
145                 150                 155

ACA GTA ATT GCC TTC TTG AGT GTG CAT GAC CAA GAC TCT GGA AAG AAT     526
Thr Val Ile Ala Phe Leu Ser Val His Asp Gln Asp Ser Gly Lys Asn
160                 165                 170                 175

GGT CAA GTT GTC TGT TAC ACA CGT GAT AAT TTA CCT TTT AAA TTA GAA     574
Gly Gln Val Val Cys Tyr Thr Arg Asp Asn Leu Pro Phe Lys Leu Glu
                180                 185                 190

AAG TCA ATA GGT AAT TAT TAT AGA TTA GTG ACA AGG AAA TAT TTG GAC     622
Lys Ser Ile Gly Asn Tyr Tyr Arg Leu Val Thr Arg Lys Tyr Leu Asp
            195                 200                 205

CGA GAA AAT GTC TCT ATC TAC AAT ATC ACA GTG ATG GCC TCA GAT CTA     670
Arg Glu Asn Val Ser Ile Tyr Asn Ile Thr Val Met Ala Ser Asp Leu
        210                 215                 220

GGA ACA CCA CCT CTG TCC ACT GAA ACT CAA ATC GCT CTG CAC GTG GCA     718
Gly Thr Pro Pro Leu Ser Thr Glu Thr Gln Ile Ala Leu His Val Ala
    225                 230                 235

GAC ATT AAC GAC AAC CCT CCT ACT TTC CCT CAT GCC TCC TAC TCA GCG     766
Asp Ile Asn Asp Asn Pro Pro Thr Phe Pro His Ala Ser Tyr Ser Ala
240                 245                 250                 255

TAT ATC CTA GAG AAC AAC CTG AGA GGA GCC TCC ATC TTT TCC TTG ACT     814
Tyr Ile Leu Glu Asn Asn Leu Arg Gly Ala Ser Ile Phe Ser Leu Thr
                260                 265                 270

GCA CAC GAC CCC GAC AGC CAG GAG AAT GCC CAG GTC ACT TAC TCT GTG     862
Ala His Asp Pro Asp Ser Gln Glu Asn Ala Gln Val Thr Tyr Ser Val
            275                 280                 285

ACC GAG GAC ACG CTG CAG GGG GCG CCC CTG TCC TCG TAT ATC TCC ATC     910
Thr Glu Asp Thr Leu Gln Gly Ala Pro Leu Ser Ser Tyr Ile Ser Ile
        290                 295                 300

AAC TCT GAC ACC GGT GTC CTG TAT GCG CTG CAA TCT TTC GAC TAT GAG     958
Asn Ser Asp Thr Gly Val Leu Tyr Ala Leu Gln Ser Phe Asp Tyr Glu
305                 310                 315

CAG ATC CGA GAC CTG CAG CTA CTG GTA ACA GCC AGC GAC AGC GGG GAC    1006
Gln Ile Arg Asp Leu Gln Leu Leu Val Thr Ala Ser Asp Ser Gly Asp
320                 325                 330                 335

CCG CCC CTC AGC AGC AAC ATG TCA CTG AGC CTG TTC GTG CTG GAC CAG    1054
Pro Pro Leu Ser Ser Asn Met Ser Leu Ser Leu Phe Val Leu Asp Gln
                340                 345                 350

AAT GAC AAC GCG CCC GAG ATC CTG TAC CCC GCC CTC CCC ACA GAC GGT    1102
Asn Asp Asn Ala Pro Glu Ile Leu Tyr Pro Ala Leu Pro Thr Asp Gly
            355                 360                 365

TCC ACT GGC GTG GAG CTG GCG CCC CGC TCC GCA GAG CGT GGC TAC CTG    1150
Ser Thr Gly Val Glu Leu Ala Pro Arg Ser Ala Glu Arg Gly Tyr Leu
        370                 375                 380

GTG ACC AAG GTG GTG GCG GTG GAC AGA GAC TCG GGC CAG AAC GCC TGG    1198
Val Thr Lys Val Val Ala Val Asp Arg Asp Ser Gly Gln Asn Ala Trp
385                 390                 395

CTG TCC TAC CGC CTG CTC AAG GCC AGC GAG CCG GGA CTC TTC TCG GTG    1246
Leu Ser Tyr Arg Leu Leu Lys Ala Ser Glu Pro Gly Leu Phe Ser Val
400                 405                 410                 415

GGT CTG CAC ACG GGC GAG GTG CGC ACG GCG CGA GCC CTG CTG GAC AGA    1294
Gly Leu His Thr Gly Glu Val Arg Thr Ala Arg Ala Leu Leu Asp Arg
                420                 425                 430

GAC GCG CTC AAG CAG AGC CTC GTG GTG GCC GTC CAG GAC CAT GGC CAG    1342
Asp Ala Leu Lys Gln Ser Leu Val Val Ala Val Gln Asp His Gly Gln
            435                 440                 445

CCC CCT CTC TCC GCC ACT GTC ACG CTC ACC GTA GCC GTG GCT GAC AGC    1390
Pro Pro Leu Ser Ala Thr Val Thr Leu Thr Val Ala Val Ala Asp Ser
        450                 455                 460
```

```
ATC CCC GAA GTC CTG ACC GAG TTG GGC AGT CTG AAG CCT TCG GTC GAC    1438
Ile Pro Glu Val Leu Thr Glu Leu Gly Ser Leu Lys Pro Ser Val Asp
    465                 470                 475

CCG AAC GAT TCG AGC CTT ACA CTC TAT CTC GTG GTG GCA GTG GCT GCC    1486
Pro Asn Asp Ser Ser Leu Thr Leu Tyr Leu Val Val Ala Val Ala Ala
480                 485                 490                 495

ATC TCC TGT GTC TTC CTC GCC TTT GTC GCT GTG CTT CTG GGG CTC AGG    1534
Ile Ser Cys Val Phe Leu Ala Phe Val Ala Val Leu Leu Gly Leu Arg
                500                 505                 510

CTG AGG CGC TGG CAC AAG TCA CGC CTG CTC CAG GAT TCC GGT GGC AGA    1582
Leu Arg Arg Trp His Lys Ser Arg Leu Leu Gln Asp Ser Gly Gly Arg
            515                 520                 525

TTG GTA GGC GTG CCT GCC TCA CAT TTT GTG GGT GTT GAG GAG GTA CAG    1630
Leu Val Gly Val Pro Ala Ser His Phe Val Gly Val Glu Glu Val Gln
        530                 535                 540

GCT TTC CTG CAG ACC TAT TCC CAG GAA GTC TCC CTC ACC GCC GAC TCG    1678
Ala Phe Leu Gln Thr Tyr Ser Gln Glu Val Ser Leu Thr Ala Asp Ser
    545                 550                 555

CGG AAG AGT CAC CTG ATC TTT CCC CAG CCC AAC TAC GCA GAC ATG CTC    1726
Arg Lys Ser His Leu Ile Phe Pro Gln Pro Asn Tyr Ala Asp Met Leu
560                 565                 570                 575

ATC AGT CAG GAG GGC TGT GAG AAA AAT GAT TCT TTG TTA ACA TCC GTA    1774
Ile Ser Gln Glu Gly Cys Glu Lys Asn Asp Ser Leu Leu Thr Ser Val
                580                 585                 590

GAT TTT CAT GAA TAT AAG AAT GAA GCT GAT CAT GGT CAG GTG AGT TTA    1822
Asp Phe His Glu Tyr Lys Asn Glu Ala Asp His Gly Gln Val Ser Leu
            595                 600                 605

GTT CTT TGC TTG CTT TTA ATT TCC AGA TGAATTTTAT TTGGCATAAA          1869
Val Leu Cys Leu Leu Leu Ile Ser Arg
        610                 615

TTATGTTTTG AAAACATTG TGAAGATAGT TGAAAATAAT TTTTAAGGTG TATCACAGAG   1929

TTTTGGGTTT ATTTTGGTGG TGTTACCAAA AAATTGAACT CTAATAGTCA TAGGTTATTG  1989

TTTCATTTGC TTTTAAACGA CTTGGAAAAG ATTGTTCCAC CATTTTAAAC CTTCCAGTAT  2049

TTTATTCCTA TTATCACTCA TTCACTTAAG AAGTAGCTAC CCGTCCATAC TGGTAATTTT  2109

GCTATTGTTT GTTTGTGTGT GTGTGTGTGT GTGTGTGTAT CCCAAACTAG             2169

AACTTCAGAA AATTATCAAG AAGTCTAAAG CCTTGTTATT AGCTTAGCAA AAGTAAAATA  2229

TATCTCAGAA TTTTTAGGGT TATGTTTAGC ATTTGAACCT GTAACTAGGC TCTTGTATAT  2289

TTCTTCACTT TAAACCTCTT TTCTGAGCCC TGTTTCTGTA CCAGTGCCCT TCAAAACTTT  2349

AATACTTCTT ACCATCCTTC AAAACATGAA CAAACTTTAA AGATGGATCT TGGTGGGAGA  2409

TGAGACTGGT TACTAAATAT TAAGTATGTG AGTCAGTGGT CACCTGGGCT CCATCCCCAT  2469

GGAGACATGA AATCTAAAGC CTAGAATGTC CATTGCTCCC CCAAACAAAA AACAAAAGCA  2529

AAAACATTAG ATCTGAATTA AAATGTAATT TTAAACTGTT GAAAGTGACT TTTGTAAAAT  2589

ATGTAAGAAC ATATTTCAAT ACAATTCCAA TTAGCTGTTT CGGTTGTGCA TTGATGTGAA  2649

GTGGTGAGAA TGTTGATATT AAGAACCAAT GTTTCAGGTA CACAAGTTCT AAATAAGCTG  2709

ATCAATTCAA TTAAAGTTAT TCAGTCTTGG CTGGACACAG TGCCTCATGT CTGAAATCCC  2769

AGCACTTTGG GAGGCTGGGG CAGGAGGACC GCTTGAGCCC CGGGGGTTTG AAACTGCAGT  2829

GAGCTATGAT CATGCCACTG CACTCCAGCC TAGGTGGCAG AACTAGACCC TGTCTCTAAA  2889

AAAACTATTA TTAGGCCGCG TGCGGTGGCT CACGCCTGTA ATCCCAGCAC TTTGGGAGAC  2949

TGAGGTGGGT GGATCACCTG AGC                                         2972
```

(2) INFORMATION FOR SEQ ID NO: 115:

(i) SEQUENCE CHARACTERISTICS:
        (A) LENGTH: 616 amino acids
        (B) TYPE: amino acid
        (D) TOPOLOGY: linear (ii) MOLECULE TYPE: protein (xi) SEQUENCE DESCRIPTION: SEQ ID NO: 115:

```
Glu Ala Ala His His Leu Val Leu Thr Ala Ser Asp Gly Gly Lys Pro
 1               5                  10                  15

Pro Arg Ser Ser Thr Val Arg Ile His Val Thr Val Leu Asp Thr Asn
                20                  25                  30

Asp Asn Ala Pro Val Phe Pro His Pro Ile Tyr Arg Val Lys Val Leu
            35                  40                  45

Glu Asn Met Pro Pro Gly Thr Arg Leu Leu Thr Val Thr Ala Ser Asp
        50                  55                  60

Pro Asp Glu Gly Ile Asn Gly Lys Val Ala Tyr Lys Phe Arg Lys Ile
65                  70                  75                  80

Asn Glu Lys Gln Thr Pro Leu Phe Gln Leu Asn Glu Asn Thr Gly Glu
                85                  90                  95

Ile Ser Ile Ala Lys Ser Leu Asp Tyr Glu Glu Cys Ser Phe Tyr Glu
            100                 105                 110

Met Glu Ile Gln Ala Glu Asp Val Gly Ala Leu Leu Gly Arg Thr Lys
        115                 120                 125

Leu Leu Ile Ser Val Glu Asp Val Asn Asp Asn Arg Pro Glu Val Ile
130                 135                 140

Ile Thr Ser Leu Phe Ser Pro Val Leu Glu Asn Ser Leu Pro Gly Thr
145                 150                 155                 160

Val Ile Ala Phe Leu Ser Val His Asp Gln Asp Ser Gly Lys Asn Gly
                165                 170                 175

Gln Val Val Cys Tyr Thr Arg Asp Asn Leu Pro Phe Lys Leu Glu Lys
            180                 185                 190

Ser Ile Gly Asn Tyr Tyr Arg Leu Val Thr Arg Lys Tyr Leu Asp Arg
        195                 200                 205

Glu Asn Val Ser Ile Tyr Asn Ile Thr Val Met Ala Ser Asp Leu Gly
210                 215                 220

Thr Pro Pro Leu Ser Thr Glu Thr Gln Ile Ala Leu His Val Ala Asp
225                 230                 235                 240

Ile Asn Asp Asn Pro Pro Thr Phe Pro His Ala Ser Tyr Ser Ala Tyr
                245                 250                 255

Ile Leu Glu Asn Asn Leu Arg Gly Ala Ser Ile Phe Ser Leu Thr Ala
            260                 265                 270

His Asp Pro Asp Ser Gln Glu Asn Ala Gln Val Thr Tyr Ser Val Thr
        275                 280                 285

Glu Asp Thr Leu Gln Gly Ala Pro Leu Ser Ser Tyr Ile Ser Ile Asn
290                 295                 300

Ser Asp Thr Gly Val Leu Tyr Ala Leu Gln Ser Phe Asp Tyr Glu Gln
305                 310                 315                 320

Ile Arg Asp Leu Gln Leu Leu Val Thr Ala Ser Asp Ser Gly Asp Pro
                325                 330                 335

Pro Leu Ser Ser Asn Met Ser Leu Ser Leu Phe Val Leu Asp Gln Asn
            340                 345                 350

Asp Asn Ala Pro Glu Ile Leu Tyr Pro Ala Leu Pro Thr Asp Gly Ser
```

```
                355                 360                 365
Thr Gly Val Glu Leu Ala Pro Arg Ser Ala Glu Arg Gly Tyr Leu Val
        370                 375                 380

Thr Lys Val Val Ala Val Asp Arg Asp Ser Gly Gln Asn Ala Trp Leu
385                 390                 395                 400

Ser Tyr Arg Leu Leu Lys Ala Ser Glu Pro Gly Leu Phe Ser Val Gly
                405                 410                 415

Leu His Thr Gly Glu Val Arg Thr Ala Arg Ala Leu Leu Asp Arg Asp
                420                 425                 430

Ala Leu Lys Gln Ser Leu Val Val Ala Val Gln Asp His Gly Gln Pro
                435                 440                 445

Pro Leu Ser Ala Thr Val Thr Leu Thr Val Ala Val Ala Asp Ser Ile
        450                 455                 460

Pro Glu Val Leu Thr Glu Leu Gly Ser Leu Lys Pro Ser Val Asp Pro
465                 470                 475                 480

Asn Asp Ser Ser Leu Thr Leu Tyr Leu Val Val Ala Val Ala Ala Ile
                485                 490                 495

Ser Cys Val Phe Leu Ala Phe Val Ala Val Leu Leu Gly Leu Arg Leu
                500                 505                 510

Arg Arg Trp His Lys Ser Arg Leu Leu Gln Asp Ser Gly Gly Arg Leu
        515                 520                 525

Val Gly Val Pro Ala Ser His Phe Val Gly Val Glu Glu Val Gln Ala
        530                 535                 540

Phe Leu Gln Thr Tyr Ser Gln Glu Val Ser Leu Thr Ala Asp Ser Arg
545                 550                 555                 560

Lys Ser His Leu Ile Phe Pro Gln Pro Asn Tyr Ala Asp Met Leu Ile
                565                 570                 575

Ser Gln Glu Gly Cys Glu Lys Asn Asp Ser Leu Leu Thr Ser Val Asp
                580                 585                 590

Phe His Glu Tyr Lys Asn Glu Ala Asp His Gly Gln Val Ser Leu Val
                595                 600                 605

Leu Cys Leu Leu Leu Ile Ser Arg
        610                 615
```